US011339392B2

(12) United States Patent
Glenn et al.

(10) Patent No.: US 11,339,392 B2
(45) Date of Patent: *May 24, 2022

(54) PAN-GENOTYPIC AGENTS AGAINST INFLUENZA VIRUS AND METHODS OF USING THE SAME

(71) Applicant: The Board of Trustees of the Leland Stanford Junior University, Stanford, CA (US)

(72) Inventors: Jeffrey S. Glenn, Palo Alto, CA (US); Rachel Hagey Saluti, Stanford, CA (US); Edward A. Pham, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/792,103

(22) Filed: Feb. 14, 2020

(65) Prior Publication Data
US 2020/0239880 A1 Jul. 30, 2020

Related U.S. Application Data

(63) Continuation-in-part of application No. 16/081,818, filed as application No. PCT/US2017/020241 on Mar. 1, 2017, now Pat. No. 10,597,658.

(60) Provisional application No. 62/302,548, filed on Mar. 2, 2016.

(51) Int. Cl.
C12N 15/11 (2006.01)
A61P 31/16 (2006.01)
C12Q 1/68 (2018.01)

(52) U.S. Cl.
CPC ............ C12N 15/11 (2013.01); A61P 31/16 (2018.01); C12N 2310/31 (2013.01); C12N 2310/322 (2013.01); C12N 2310/3231 (2013.01); C12N 2310/531 (2013.01)

(58) Field of Classification Search
None
See application file for complete search history.

(56) References Cited

U.S. PATENT DOCUMENTS

| 2004/0242518 | A1 | 12/2004 | Chen et al. |
| 2006/0148747 | A1 | 7/2006 | Stein et al. |
| 2009/0042823 | A1 | 2/2009 | Templin et al. |
| 2010/0254945 | A1 | 10/2010 | Ge et al. |
| 2012/0003156 | A1 | 1/2012 | Dang et al. |
| 2014/0303073 | A1* | 10/2014 | Iversen .................... C07K 7/08 514/3.7 |
| 2017/0191062 | A1* | 7/2017 | Dale ........................ C12Q 1/701 |

FOREIGN PATENT DOCUMENTS

| JP | 2012506698 A | 3/2012 |
| JP | 2013049714 A | 3/2013 |
| JP | 2013515504 A | 5/2013 |
| JP | 2013532965 A | 8/2013 |
| WO | WO1992003454 A1 | 3/1992 |
| WO | WO2006110688 A2 | 10/2006 |
| WO | WO2007084359 A2 | 7/2007 |
| WO | WO2008049078 A1 | 4/2008 |
| WO | WO2011060320 A1 | 5/2011 |
| WO | WO2017151795 A1 | 9/2017 |

OTHER PUBLICATIONS

Giannecchini et al., Arch Virol vol. 154:821-832, 2009.*
Vester et al., Biochemistry vol. 43(42):13233-13241, 2004.*
Akbari, Akbar et al. (2008) "Improved DNA Fragment Length Estimation in Capillary Electrophoresis," *Electrophoresis Journal* 29:1273-1285.
Cordero, Pablo et al. (2012) "An RNA Mapping DataBase for Curating RNA Structure Mapping Experiments," *Bioinformatics* 28(22):3006-3008.
Cordero, Pablo (2013) "A Mutate-and-Map Protocol for Inferring Base Pairs in Structured RNA," 22 pages.
Darty, Kévin et al. (2009) "VARNA: Interactive Drawing and Editing of the RNA Secondary Structure," *Bioinformatics* 25(15)1974-1975.
Deigan, Katherine E. et al. (2009) "Accurante SHAPE-Directed RNA Structure Determination," *PNAS* 106(1):97-102.
De Rijk, Peter et al. (2003) "RNA Viz 2: An Improved Representation of RNA Secondary Structure," Bioinformatics 19(2):299-300.
Gao, Qinshan et al. (2012) "The Influenza A Virus PB2, PA, NP, and M Segments Play a Pivotal Role during Genome Packaging," *Journal of Virology* 86(13)7043-7051.
Giannecchini et al. (2009) "Oligonucleotides Derived from the Packaging Signal at the 5' End of the Viral PB2 Segment Specifically Inhibit Influenza Virus In Vitro," *Arch Virol*. 154(5):821-32.
Gog, Julia R. et al. (2007) "Codon Conservation in the Influenza A Virus Genome Defines RNA Packaging Signals," *Nucleic Acids Research* 35(6):1897-1907.

(Continued)

*Primary Examiner* — Sean McGarry
(74) *Attorney, Agent, or Firm* — Kyle A. Gurley; Bret E. Field; Bozicevic, Field & Francis LLP

(57) ABSTRACT

Methods of inhibiting influenza A virus in a sample are provided. Aspects of the methods include contacting a sample comprising viral RNA (vRNA) having a PSL2 motif with an effective amount of an agent that specifically binds the PSL2 motif to inhibit the influenza A virus. Also provided are methods of treating or preventing influenza A virus infection in a subject. Also provided are methods for screening a candidate agent for the ability to inhibit influenza A virus in a cell, the method comprising: contacting a sample with a candidate agent; and determining whether the candidate agent specifically binds to the PSL2 motif of vRNA. Also provided are compounds and pharmaceutical compositions comprising an oligonucleotide sequence complementary to a PB2 vRNA region that find use in the subject methods.

Figure 1B:
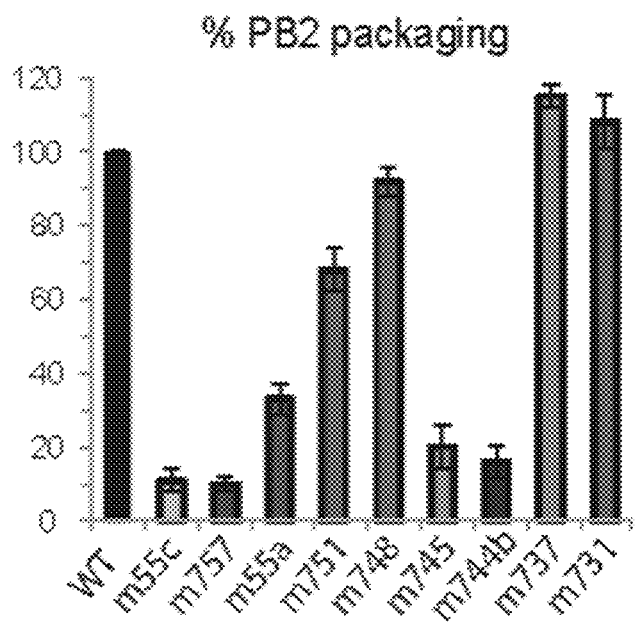

33 Claims, 30 Drawing Sheets
Specification includes a Sequence Listing.

(56) References Cited

OTHER PUBLICATIONS

Hoffmann, Erich et al. (2000) "A DNA Transfection System for Generation of Influenza A Virus from Eight Plasmids," *PNAS* 97(11):6108-6113.

Integrated DNA Technologies, (2011) "Designing Antisense Oligonucleotides," 16 pages.

Kierzek et al. (2009) "Contributions of Stacking, Preorganization, and Hydrogen Bonding to the Thermodynamic Stability of Duplexes Between RNA and 2'-O-Methyl RNA with Locked Nucleic Acids," *Biochemistry* 48(20):4377-87.

Kim, Kinkyu et al. (2009) "A Robust Peak Detection Method for RNA Structure Inference by High-Throughput Contact Mapping," *Bioinformatics* 25(9):1137-1144.

Kim, Hanjoo et al. (2013) "HiTRACE-Web: An Online Tool for Robust Analysis of High-Throughput Capillary Electrophoresis," *Nucleic Acids Research* 41:W492-W498.

Kladwang, Wipapat et al. (2010) "A Mutate-and-Map Strategy for Inferring Base Pairs in Structured Nucleic Acids: Proof of Concept on a DNAA/RNA Helix," Biochemistry 49(35):7414-7416.

Kladwang, Wipapat et al. (2011) "A Mutate-and-Map Strategy Accurately Infers the Base Pairs of a 35-Nucleotide Model RNA," RNA 17(3):1-14.

Kladwang, Wipapat et al. (2013) "A Two-Dimensional Mutate-and-Map Strategy for Non-Coding RNA Structure," *Nat Chem.* 3(12):954-962.

Kladwang, Wipapat et al. (2014) "Standardization of RNA Chemical Mapping Experiments," *Biochemistry* 53:3063-3065.

Liang, Yuhong et al. (2008) "Mutational Analyses of Packaging Signals in Influenza Virus PA, PB1, and PB2 Genomic RNA Segments," *Journal of Virology* 82(1):229-236.

Marsh, Glenn A. (2007) "Specific Residues of the Influenza A Virus Hemagglutinin Viral RNA Are Important for Efficient Packaging into Budding Virions," *Journal of Virology* 81(18):9727-9736.

Marsh, Glenn A. (2008) "Highly Conserved Regions of Influenza A Virus Polymerase Gene Segments Are Critical for Efficient Viral RNA Packaging," *Journal of Virology* 82(5):2295-2304.

Mathews, David H. et al. (2004) "Incorporating Chemical Modification Constraints into a Dynamic Programming Algorithm for Prediction of RNA Secondary Structure," *PNAS* 101(19):7287-7292.

Mortimer, Stefanie A. et al. (2007) "A Fast Acting Reagent for Accurate Analysis of RNA Secondary and Tertiary Structure by SHAPE Chemistry," *J. Am. Chem. Soc.* 129(14):4144-4145.

Mortimer, Stefanie A. et al. (2009) "Time-Resolved RNA SHAPE Chemistry: Quantitative RNA Structure Analysis in One Second Snapshots and at Single Nucleotide Resolution," *Nat Protoc.* 4(10):1413-1421.

Moss, Walter N. et al. (2011) "Identification of Potential Conserved RNA Secondary Structure Throughout Influenza A Coding Regions," *RNA* 17:6(991-1011).

Muramoto, Yukiko et al. (2006) "Hierearchy Among Viral RNA (vRNA) Segments in Their Role in vRNA Incorporation into Influenza A Virions," *Journal of Virology* 80(5):2318-2325.

Pang, Phillip S. (2011) "Simplified RNA Secondary Structure Mapping by Automation of SHAPE Data Analysis," Nucleic Acids Research 39(22):1-11.

Pang, Phillip S. (2012) "Structural Map of a MicroRNA-122:Hepatitis C Virus Complex," *Journal of Virology* 86(2):1250-1254.

International Search Report and Written Opinion of corresponding PCT Application PCT/US2017/020241 dated Aug. 11, 2017, 18 pages.

IPRP of corresponding PCT Application PCT/US2017/020241 dated Sep. 13, 2018, 9 pages.

Priore, Salvatore F. (2012) "Influenza A Virus Coding Regions Exhibit Host-Specific Glabal Ordered RNA Strcture," *PLoS One* 7(4)1-8.

Szretter, Kristy J. et al. (2006) "Influenza: Propagation, Quantification, and Storage," *Current Protocols in Microbiology* 15G.1.1-15G.1.22.

Tian, Siqi et al. (2014) "High-Throughput Mutate-Map-Rescue Evaluates SHAPE-Directed RNA Structure and Uncovders Excited States," Cold Spring Harbor Laboratory Press 20:1815-1826.

Vester Birte et al. (2004) "LNA (Locked Nucleic Acid): High-Affinity Targeting of Complementary RNA and DNA," *Biochemistry* 43(42):13233-13241.

Wilkinson, Kevin Andrew et al. (2006) "Selective 2'-Hydroxyyl Acylation Analyzed by Primer Extension (SHAPE): Quantitative RNA Structure Analysis at Single Nucleotide Resolution," *Nature Protocols* 1(3):1610-1616.

Yoon, Sungroh et al. (2011) "HiTRACE: High-Throughput Robust Analysis for Capillary Electrophoresis," *Bioinformatics* 27(13):1798-1805.

Abe, et al. "Antisense therapy of inflienza", European Journal of Pharmaceutical Sciences 13(1):61-69.

Brown, et al. "Inhibition of HIV-1 replication by oligonucleotide analogues directed to the packaging signal and trans-activating response region", Antivir Chem Chemother, 2006;17(1):1-9.

Jin, et al. "Inhibition of highly pathogenic avian H5N1 influenza virus propagation by RNA oligonucleotides targeting the PB2 gene in combination with celecoxib", J Gene 1\led 201 J.; 13: 243-249.

Takahashi, et al. "Inhibition of influenza virus infection by targeting genome conserved region with non-natural nucleic acid", Nucleic Acids Symp Ser (Oxf)., 2009;(53):285-6.

\* cited by examiner

FIG. 1A

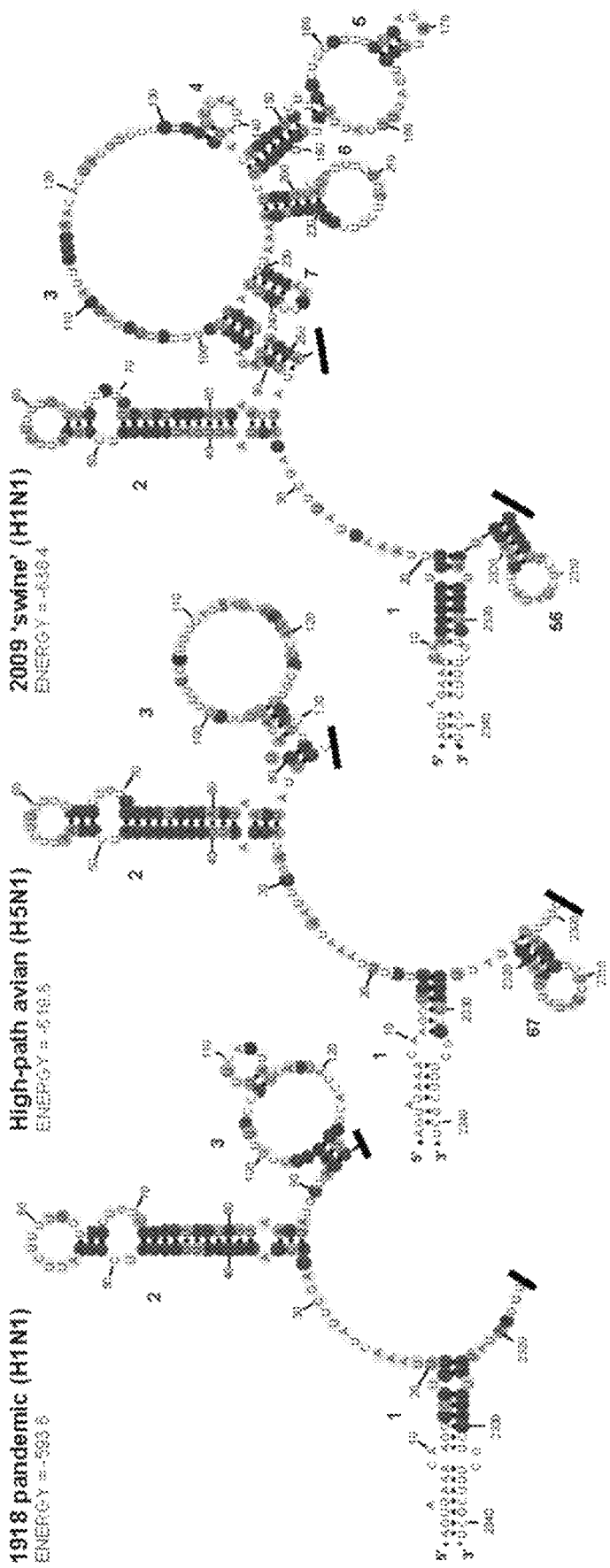

FIG. 2
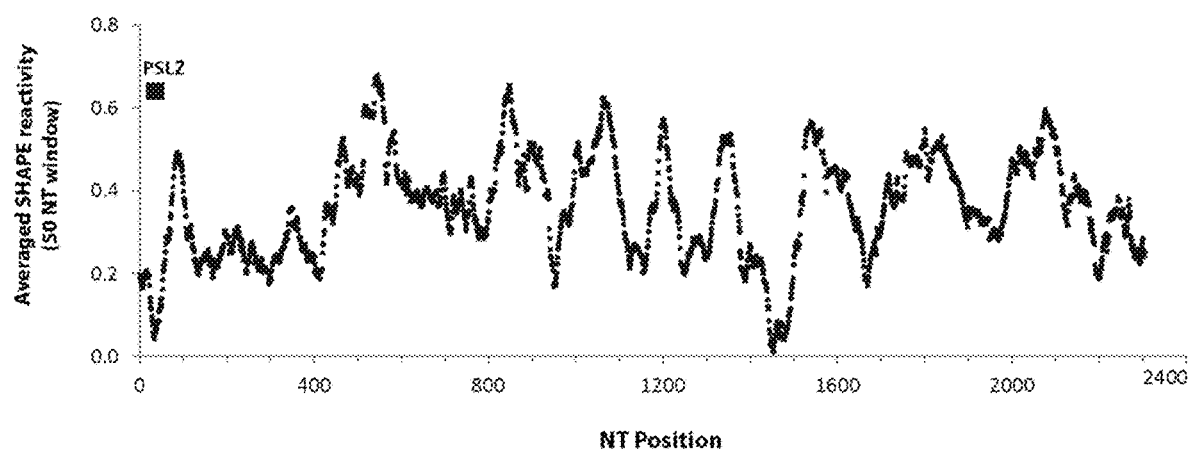
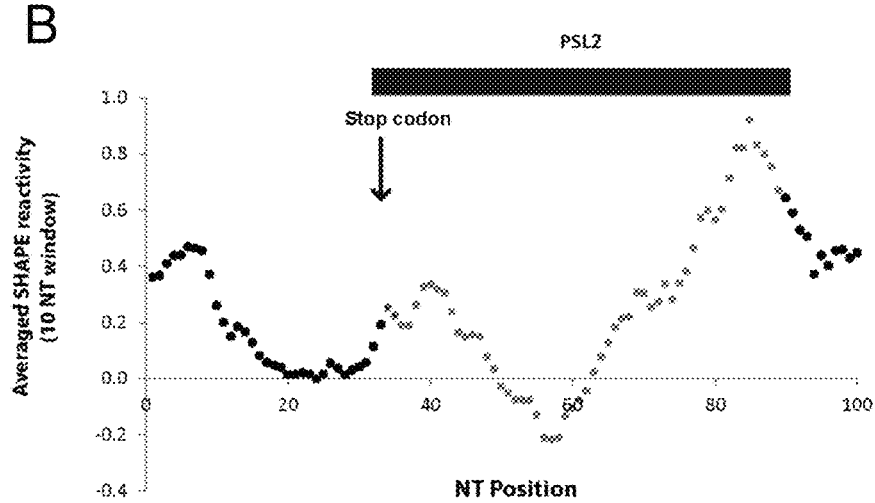

Figure 3A:
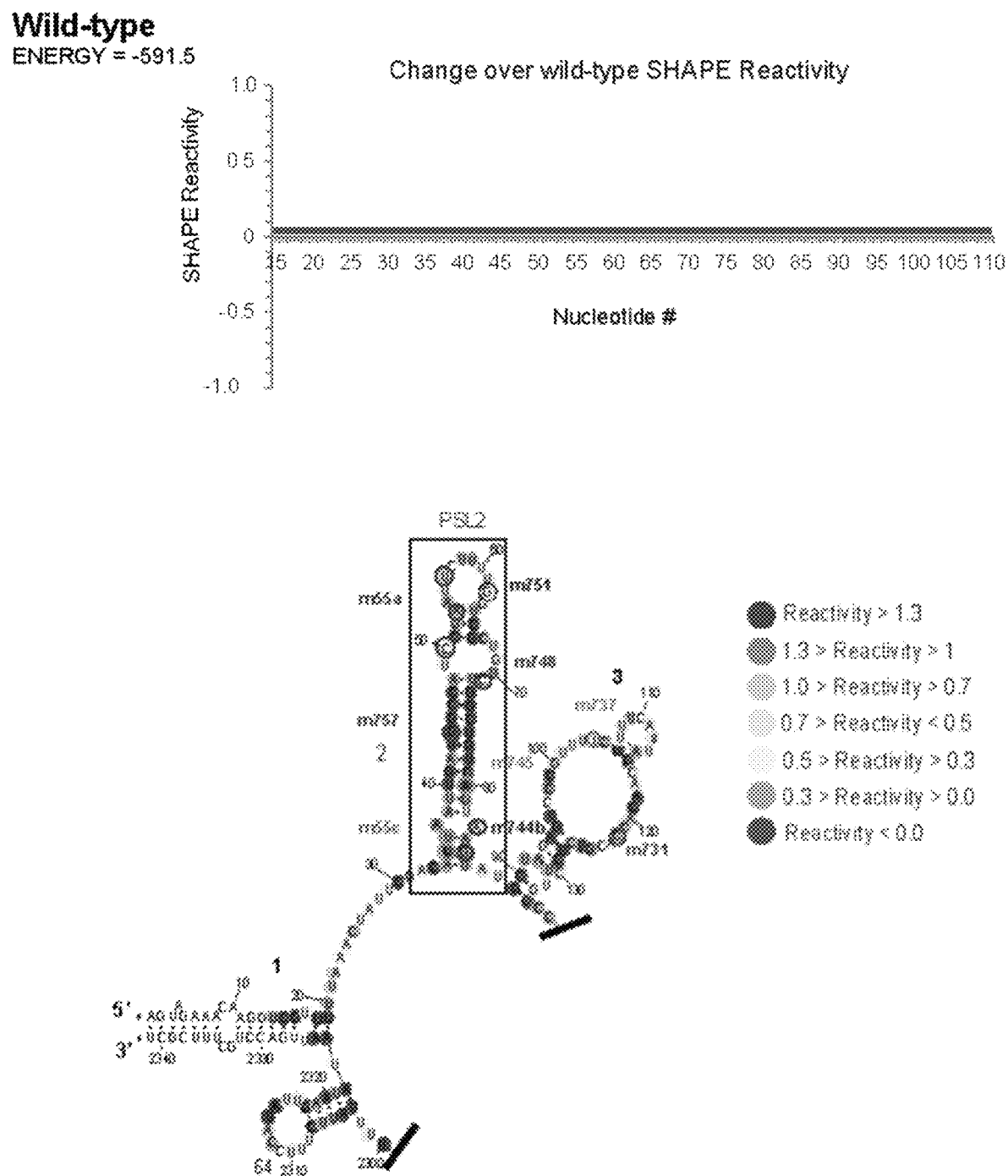

FIG. 3B
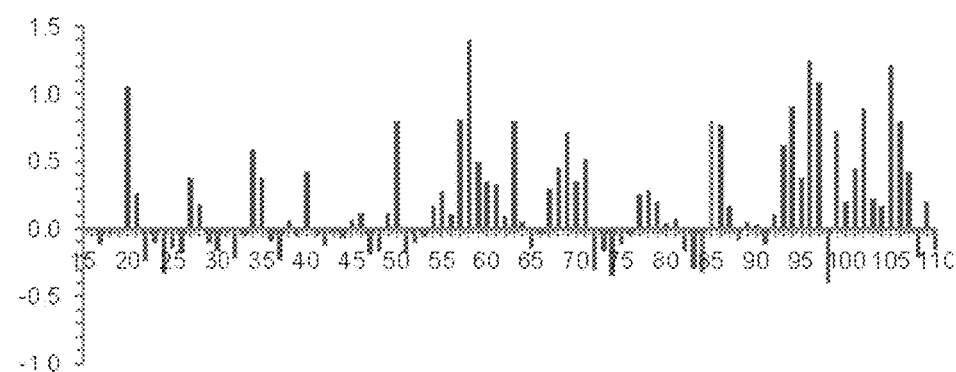
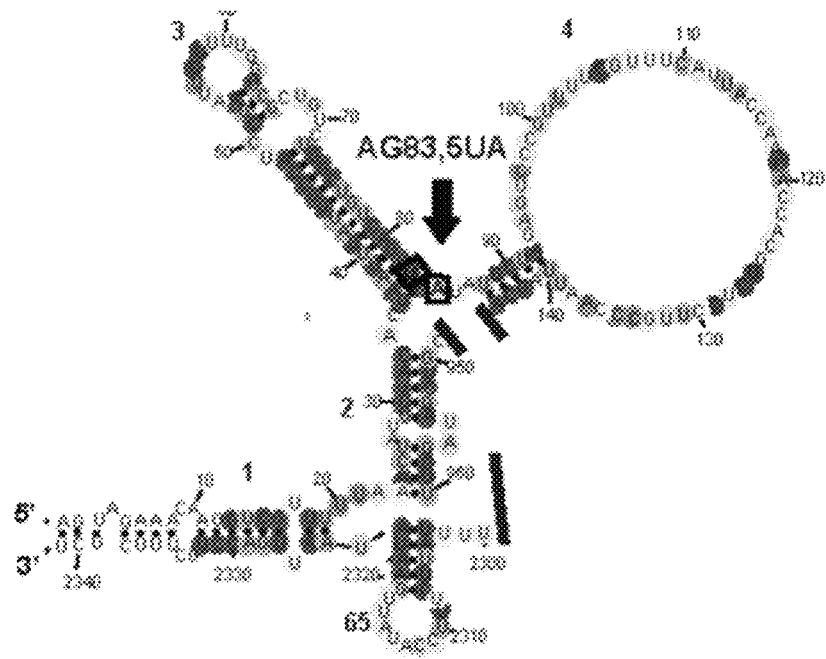

FIG. 3C
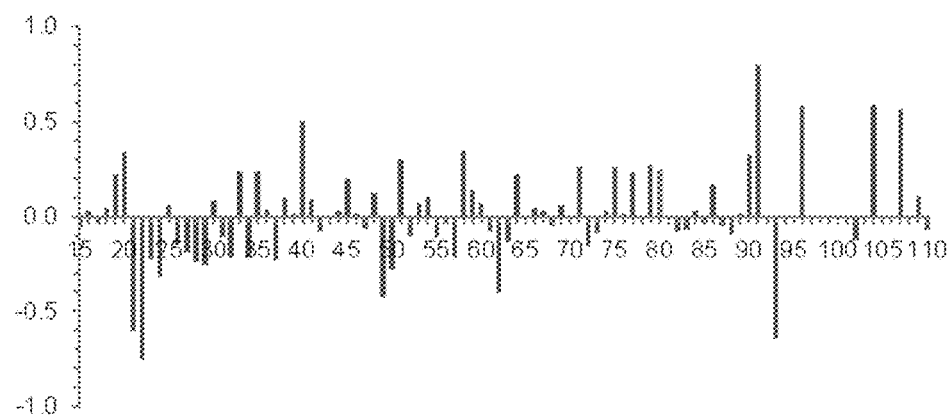
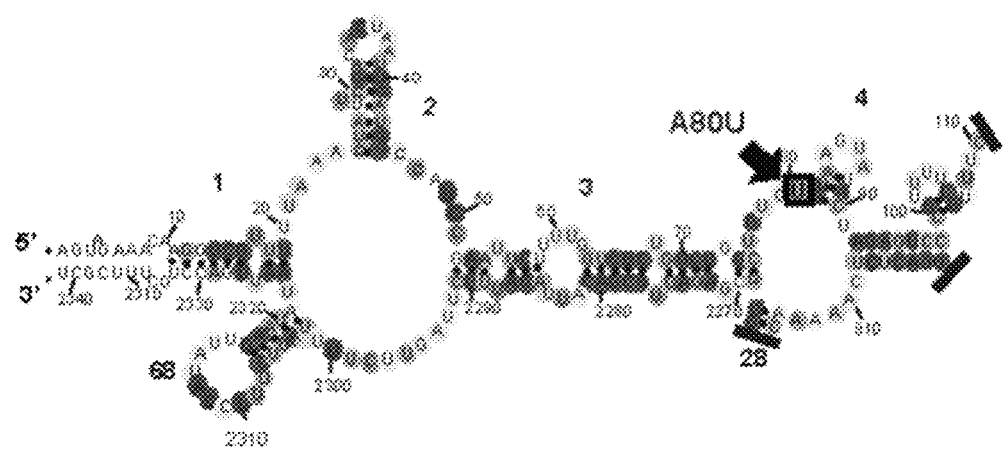

FIG. 3D
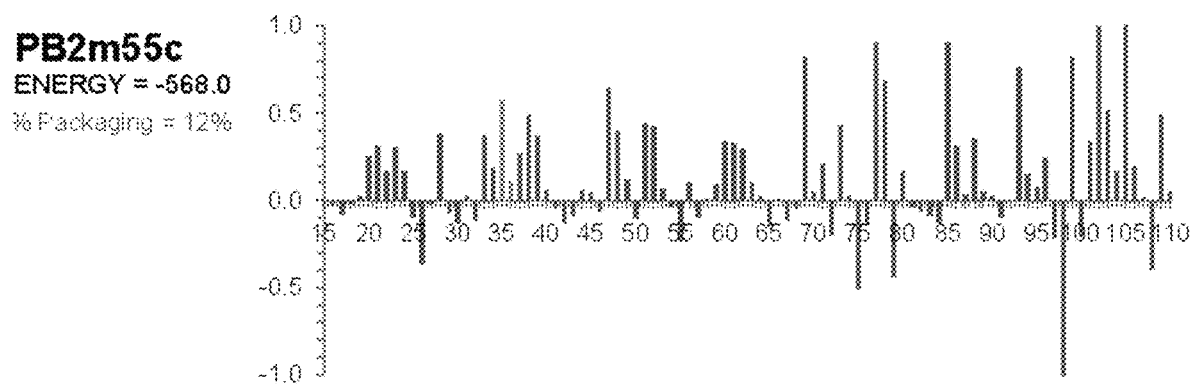
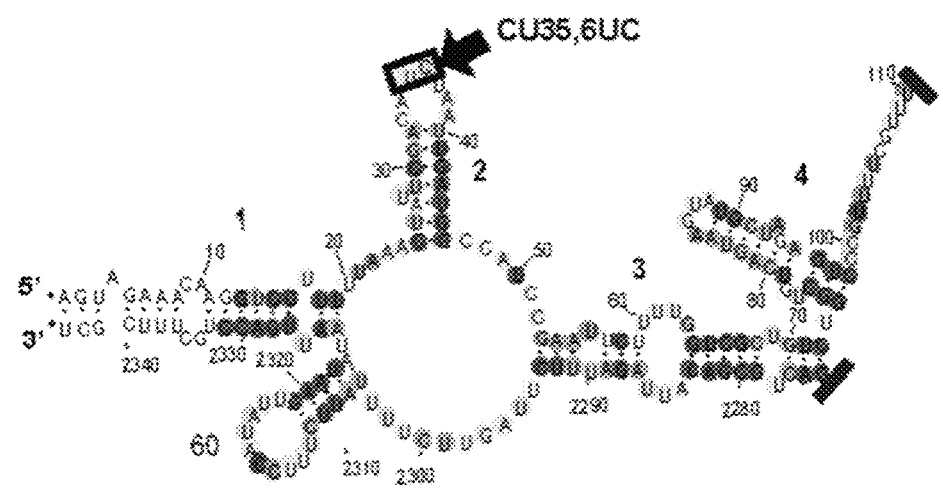

FIG. 3E
PB2m757
ENERGY = -578.0
% Packaging = 9%
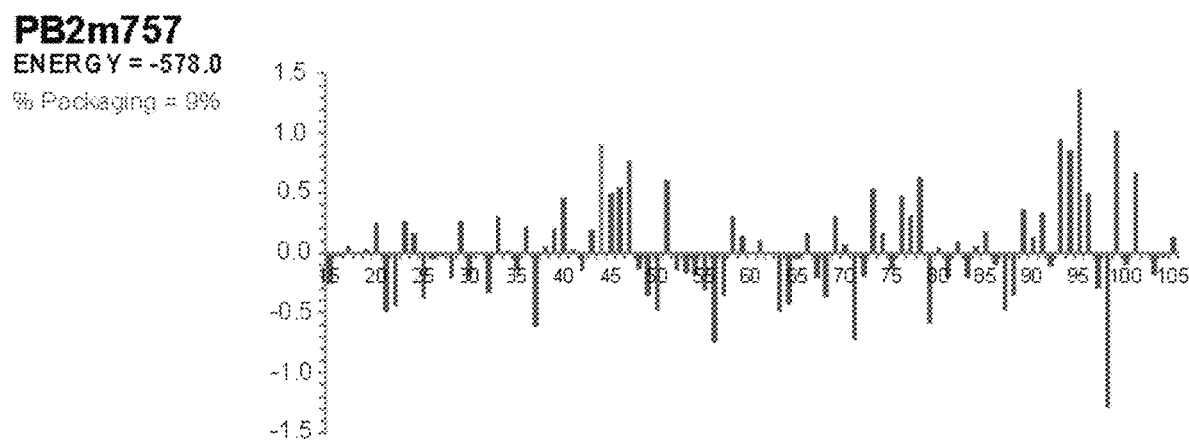
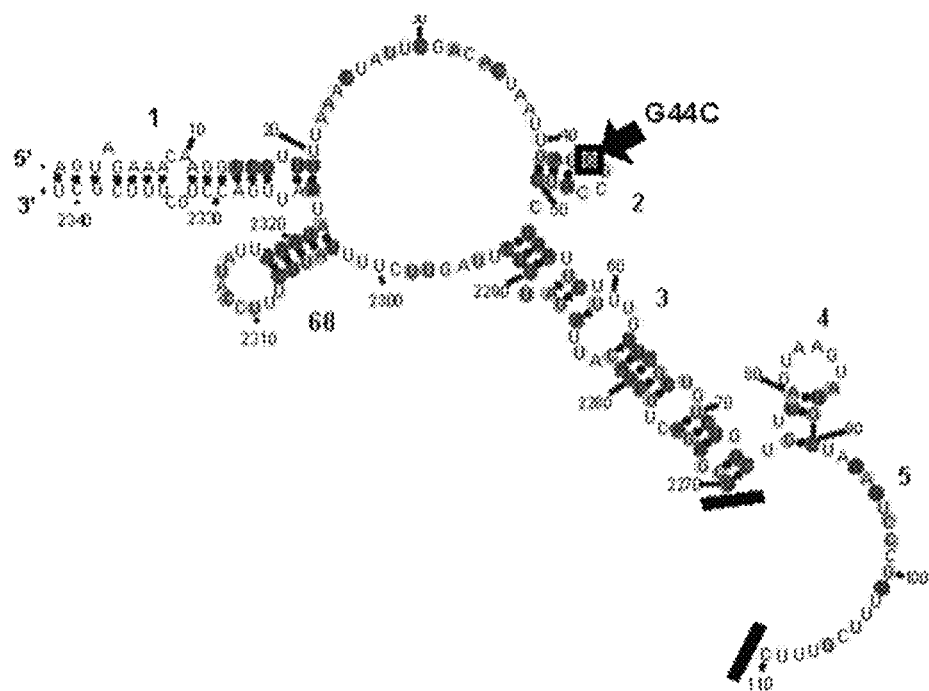

FIG. 6

B

WT     PB2m55c     PB2m55c-comp (non-synonymous)

A    A       A    A       A      A
U·A       ● x A  →   ☐G☐·☐A☐    Leu → Ser
C·G       ●·G           ●·U

WT     PB2m745     PB2m745-comp

U·A       U x U  →   ☐A☐·U    Asn → Tyr
U·G       U·G           U·G
A·U       A·U           A·U

WT     PB2m757     PB2m757-comp

C·G       C·G           C·G
G·C       G·C  →   G·C
G·U       ● x U           ●·☐G☐    Ser → Arg

A

[RNA secondary structure diagram showing stem-loop with positions 30, 40, 50, 60, 70, 80, 5', 3'; labeled mutations m55c, m745, m757 and their complements m55c-comp, m745-comp, m757-comp]

FIG. 7

A

```
    2203                    2215                  2227
    ATT GGG CAA  GGA GAC GTG GTG  TTG GTA ATG  AAA CGG

ATT GGG CAA  GGA GAC GTC GTG  TTG GTA ATG  AAA CGG
                         m731

2239                   2251                  2263
    AAA CGG AAC  TCT AGC ATA CTT  ACT GAC AGC  CAG ACA

AAA CGG AAC  TCT AGC ATA TTA  ACA GAC AGC  CAA ACA
                          m744b m745              m748

2275                   2287                  2299
    GCG ACC AAA  AGA ATT CGG ATG  GCC ATC AAT  TAG TGT

GCG ACG AAA  AGA ATT CGG ATG  GCG ATC AAT  TGA TGT
        m751                      m757              m55c
```

B

Mutate-and-Map predicted PB2 mutations (Syn.) m74-1 (C2268T)-F: TAC TTA CTG ACA GTC AGA CAG CG
(Syn.) m74-1 (C2268T)-RC: CGC TGT CTG ACT GTC AGT AAG TA (Syn.) m74-2 (AGC2266-8UCG)-F: TAC TTA CTG ACT CGC AGA CAG CG
(Syn.) m74-2 (AGC2266-8UCG)-RC: CGC TGT CTG CGA GTC AGT AAG TA (Syn.) m68-1 (A2262T)-F: TGA CAG CCA GAC TGC GAC CAA AAG AAT TCG
(Syn.) m68-1 (A2262T)-RC: CGA ATT CTT TTG GTC GCA GTC TGG CTG TCA (Syn.) m56 (A2286C)-F: AGC GAC CAA AAG CAT TCG GAT GGC
(Syn.) m56 (A2286C)-RC: GCC ATC CGA ATG CTT TGT CGC T

C

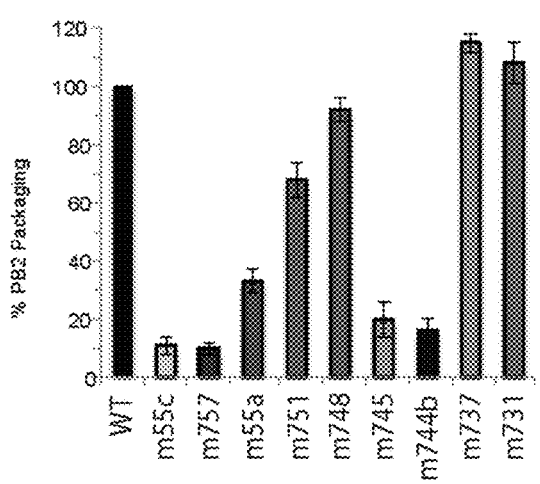

D

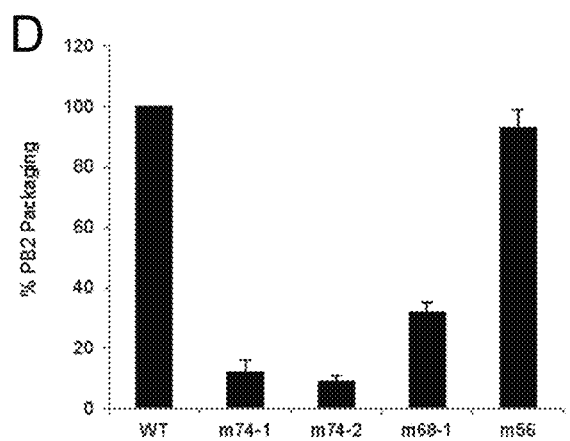

FIG. 8

Mutant Nomenclature and Mutation Sites

| | Mutant Name | Mutation Site(s) [(-)-sense orientation] | SYN or Non-SYN | Notes |
|---|---|---|---|---|
| Previously-described Mutants | m55c | CU35,36UC | SYN | |
| | m757 | G44C | SYN | |
| | m55a | CAU50,53,56 | SYN | |
| | m751 | G62C | SYN | |
| | m748 | C71U | SYN | |
| | m745 | A80U | SYN | |
| | m744b | AG83,85UA | SYN | |
| | m737 | U104 | SYN | |
| | m731 | C122G | SYN | |
| Novel PSL2-informed Mutants | m83,84 | AG83,84GA | Non-SYN | |
| | m55c-comp | CU35,36UC / AG83,84GA | Non-SYN | Dbl Mutant |
| | m76 | U76G | Non-SYN | |
| | m757-comp | G44C / U76G | Non-SYN | Dbl Mutant |
| | m40 | U40A | Non-SYN | |
| | m745-comp | A80U / U40A | Non-SYN | Dbl Mutant |
| | m74-1 | G74A | SYN | |
| | m74-2 | UCG74AGC | SYN | |
| | m68 | U68A | SYN | |
| | m56 | U56G | SYN | |
| | m41 | G41C | Non-SYN | |
| | m79 | C79G | Non-SYN | |
| | m41/79-comp | GC41,79CG | Non-SYN | Dbl Mutant |
| | m45 | G45C | Non-SYN | |
| | m75 | C75G | Non-SYN | |
| | m45/75-comp | GC45,75CG | Non-SYN | Dbl Mutant |
| | m46 | C46G | Non-SYN | |
| | m74 | G74C | Non-SYN | |
| | m46/74-comp | CG46,74GC | Non-SYN | Dbl Mutant |
| | m52 | G52U | SYN | |
| | m65 | C65A | SYN | |
| | m52/65-comp | GC52,65UA | SYN | Dbl Mutant |

SYN = Synonymous mutation, Non-SYN = non-synonymous mutation

FIG. 9A
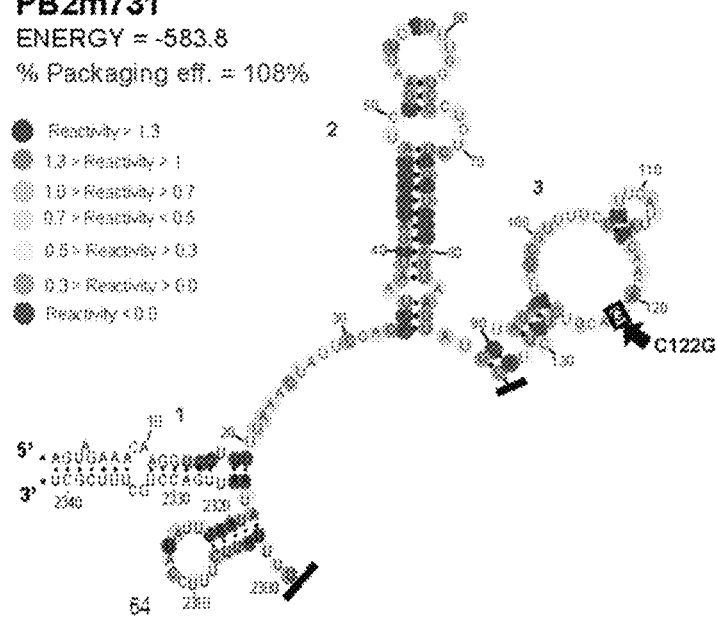
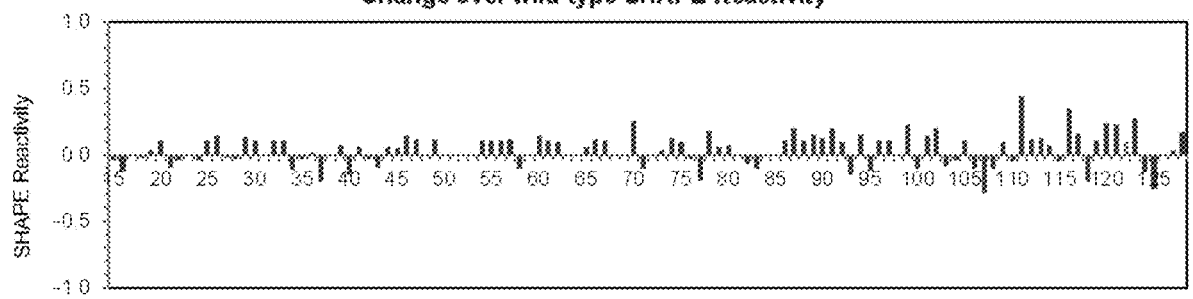

FIG. 9B
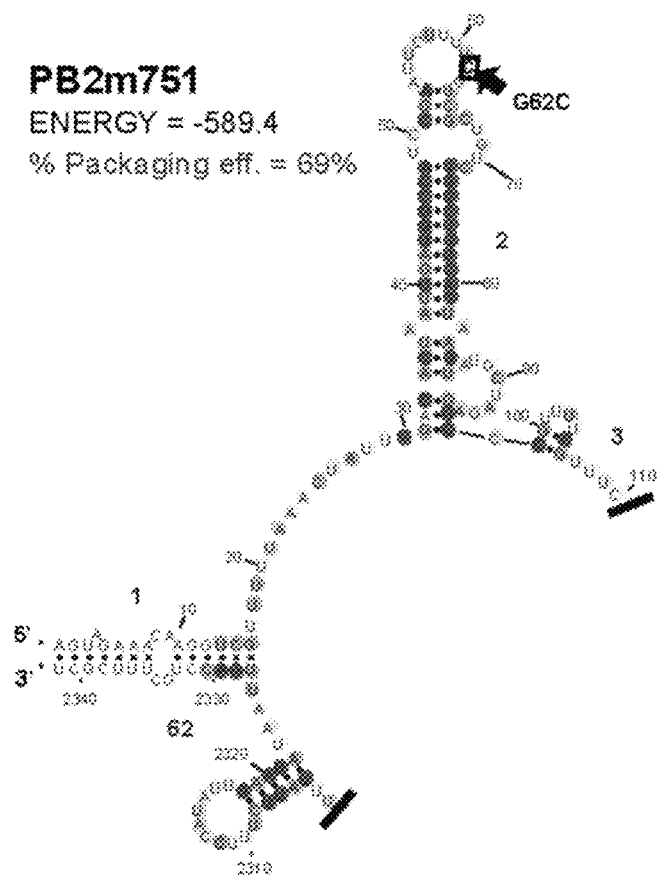
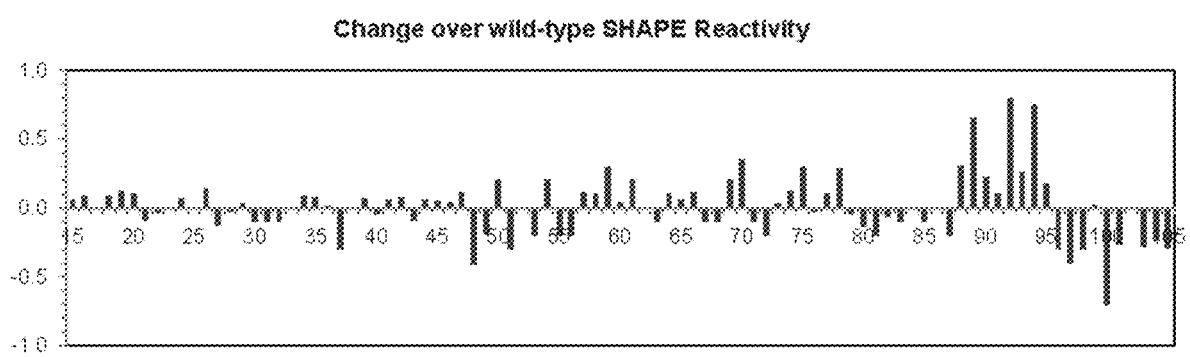

FIG. 13

(Non-syn.) m46-F (G2296C): AGA ATT CGG ATG CCC ATC AAT TAG TGT CG
(Non-syn.) m46-RC (G2296C): CGA CAC TAA TTG ATG GGC ATC CGA ATT CT
(Syn.) m46/74-comp (C2268G)-F: TAC TTA CTG ACA GGC AGA CAG CG
(Syn.) m46/74-comp (C2268G)-RC: CGC TGT CTG CCT GTC AGT AAG TA (Non-syn.) m45-F (G2297C): TTC GGA TGG GCA TCA ATT AGT GTC G
(Non-syn.) m45-RC (G2297C): CGA CAC TAA TTG ATG CCC ATC CGA A
(Non-syn) m45/75-comp (G2267C)-F: ATA CTT ACT GAC ACC CAG ACA GCG
(Non-syn) m45/75-comp (G2267C)-RC: CGC TGT CTG GGT GTC AGT AAG TAT (Non-syn.) m41-F (C2301G): TCG GAT GGC CAT GAA TTA GTG TCG
(Non-syn.) m41-RC (C2301G): CGA CAC TAA TTC ATG GCC ATC CGA
(Syn.) m41/79-comp (G2263C)-F: AGC ATA CTT ACT CAC AGC CAG ACA GC
(Syn.) m41/79-comp (G2263C)-RC: GCT GTC TGG CTG TGA GTA AGT ATG CT (Syn.) m52-F (C2290A): CCA AAA GAA TTA GGA TGG CCA TCA ATT AGT GTC G    Double synonymous mutant pair
(Syn.) m52-RC (C2290A): CGA CAC TAA TTG ATG GCC ATC CTA ATT CTT TTG G
(Syn.) m65-F (G2277T): GAC AGC CAG ACA GCT ACC AAA AGA ATT CG
(Syn.) m65-RC (G2277T): CGA ATT CTT TTG GTA GCT GTC TGG CTG TC

FIG. 17
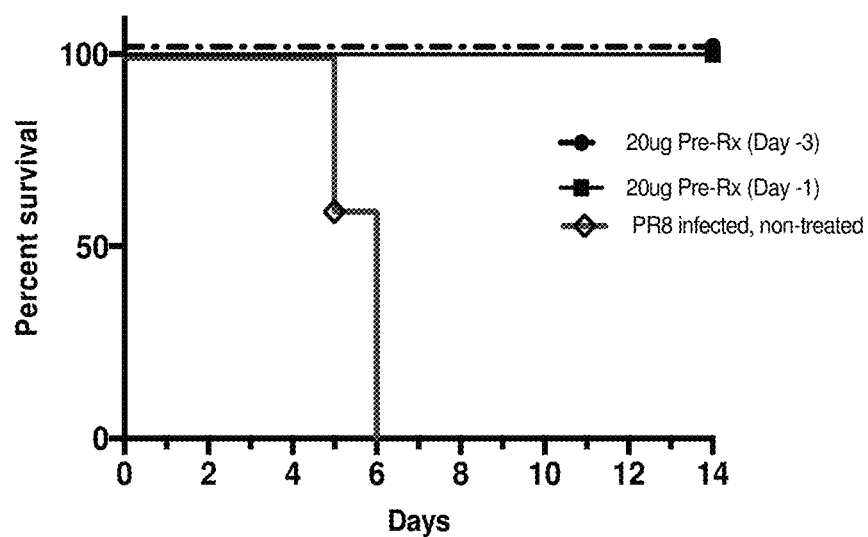
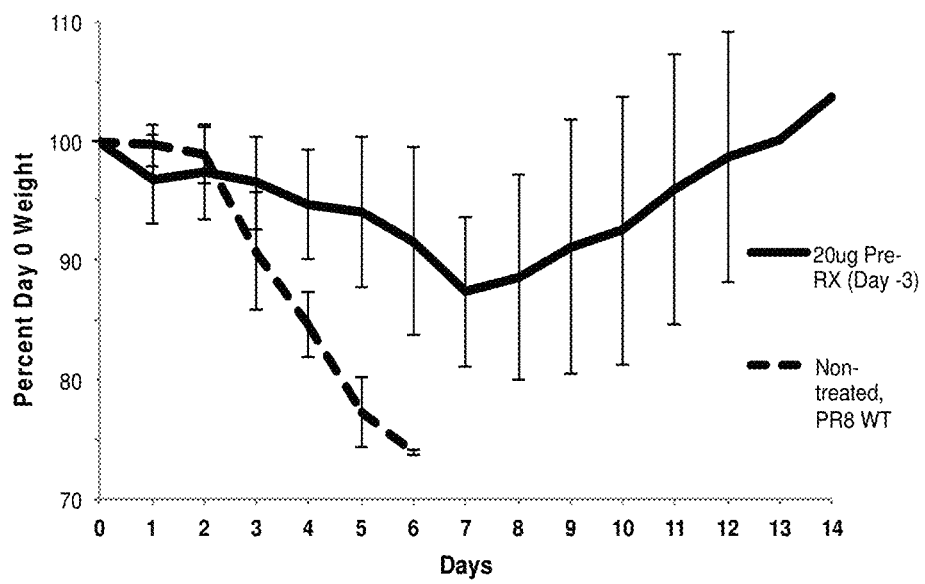

FIG. 19
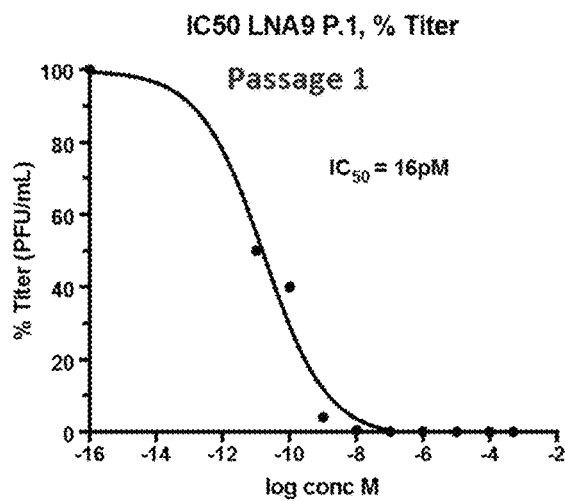
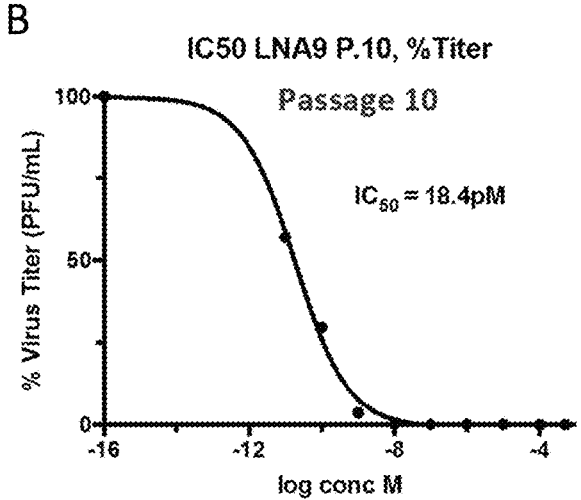
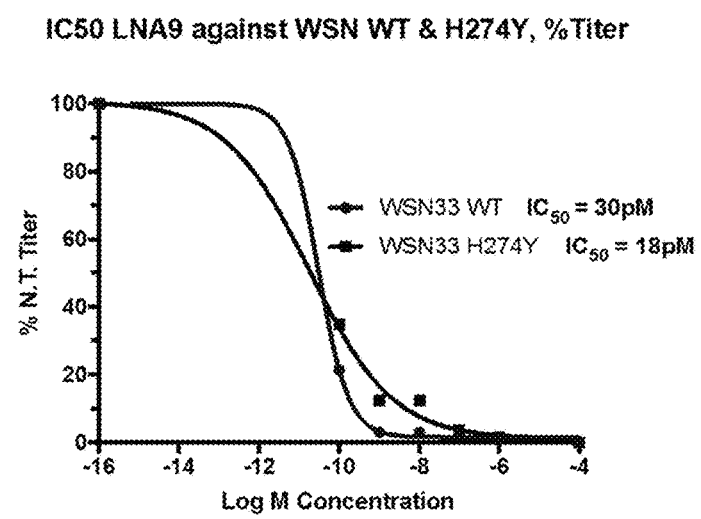

PAN-GENOTYPIC AGENTS AGAINST INFLUENZA VIRUS AND METHODS OF USING THE SAME

CROSS-REFERENCE

This application is a continuation-in-part of U.S. patent application Ser. No. 16/081,818, filed Aug. 31, 2018, which is a 371 National Phase application of PCT/US2017/20241, filed on Mar. 1, 2017 and claims the benefit of U.S. Provisional Patent Application No. 62/302,548, filed Mar. 2, 2016, all of which are incorporated herein by reference in their entirety.

GOVERNMENT RIGHTS

This invention was made with government support under grant number AI109662 awarded by the National Institutes of Health.

The government has certain rights in the invention.

INTRODUCTION

Influenza A virus (IAV) is a segmented RNA virus that causes significant morbidity and mortality worldwide. All currently approved IAV antiviral drugs are targeted against viral proteins, are subtype limited, and are challenged by rising antiviral resistance against all drug class members.

The IAV genome consists of eight single-stranded negative-sense viral RNA (vRNA) segments that encode a minimum of 14 known viral proteins. The vRNA, together with nucleoprotein (NP) and the heterotrimeric polymerase complex, comprised of PB2, PB1, and PA proteins, forms the complete viral ribonucleoprotein (vRNP). To be fully infectious, IAV virions must incorporate at least one of each segment's vRNP. Each vRNP interacts with at least one other partner to form a supramolecular complex likely maintained by intersegment RNA-RNA and/or protein-RNA interactions hypothesized to guide the packaging process.

SUMMARY

Aspects of the present disclosure provide pan-genotypic compositions designed to disrupt an RNA structural element of IAV, called Packaging Stem-Loop 2 (PSL2), within the 5' packaging signal region of genome segment PB2. Disruption of PSL2 structure dramatically inhibits IAV. PSL2 is conserved across all tested influenza A subtypes.

Methods of inhibiting influenza A virus in a sample are provided. Aspects of the methods include contacting a sample comprising viral RNA (vRNA) having a PSL2 motif with an effective amount of an agent that specifically binds the PSL2 motif to inhibit the influenza A virus. In some cases, the vRNA is isolated from a virion or a cell. In some cases, the vRNA is in a virion. In some cases, the vRNA is in an infected cell. Also provided are methods of treating or preventing influenza A virus infection in a subject. Also provided are methods for screening a candidate agent for the ability to inhibit influenza A virus in a cell, the method comprising: contacting a sample with a candidate agent; and determining whether the candidate agent specifically binds to the PSL2 motif of vRNA. Also provided are compounds and pharmaceutical compositions comprising an oligonucleotide sequence complementary to a PB2 vRNA region that find use in the subject methods.

BRIEF DESCRIPTION OF THE FIGURES

The skilled artisan will understand that the drawings, described below, are for illustration purposes only. The drawings are not intended to limit the scope of the present teachings in any way.

FIG. 1A-FIG. 1F depicts RNA secondary structures of wild-type PB2 (SEQ ID NO: 1) and packaging mutant vRNAs, PB2m757 (SEQ ID NO: 2), m745 (SEQ ID NO: 3), 1918 pandemic (H1N1) (SEQ ID NO: 4), High-path avian (H5M=N1) (SEQ ID NO: 5) and 2009 swine (H1N1) (SEQ ID NO: 6).

FIG. 2, panels A and B, depicts the reactivity of full-length PB2 vRNA.

FIG. 3A-FIG. 3E depicts the disruption of wild-type reactivity (SEQ ID NO: 7) by packaging-defective mutations, PB2m744b (SEQ ID NO: 8), PB2m745 (SEQ ID NO: 9), PB2m55c (SEQ ID NO: 10) and PB2m757 (SEQ ID NO: 11).

FIG. 4 depicts the conservancy of nucleotide sequence containing the PSL2 structure.

FIG. 5A-FIG. 5D depicts the 2-dimensional Mutate-and-Map analysis of PSL2 RNA secondary structure (FIG. 5C, SEQ ID NO: 12).

FIG. 6, panels A-B, depicts the design of compensatory mutations to previously described PR8 PB2 mutants (panel A, SEQ ID NO: 13).

FIG. 7, panels A-D, depicts synonymous mutation of single highly conserved codons of the PR8 PB2 vRNA (panel A, SEQ ID NOs: 14-15; panel B, SEQ ID NOs: 16-23 top to bottom).

FIG. 8 depicts a table showing PB2 packaging mutant nomenclature and corresponding sites of mutation.

FIG. 9A-FIG. 9C depicts the effect of synonymous mutation on PSL2 structure, PB2m731 (SEQ ID NO: 24), PB2m751 (SEQ ID NO: 25) and PB2m748 (SEQ ID NO: 26).

FIG. 10, panels A-I, depicts the effect of compensatory mutations in PR8 PB2 packaging-defective mutants on viral packaging and titer.

FIG. 11 panels A-D, depicts multidimensional chemical mapping of PB2 packaging-defective and compensatory mutant partners (panel B, SEQ ID NO: 27).

FIG. 12, panels a-t, depicts 2-dimensional Mutate-Map-Rescue analysis.

FIG. 13 depicts the design of primer sequences for 2-dimensional Mutate-Map-Rescue mutants. Sequences correspond to SEQ ID NOs: 28-43, top to bottom.

FIG. 14, panels A-B, depicts that packaging-defective viruses are attenuated in vivo.

FIG. 15, panels A-D, depicts antiviral activity of Locked Nucleic Acids targeting PSL2 RNA structure (panel A, SEQ ID NO: 44).

FIG. 16A-FIG. 16B depicts analysis on LNA-RNA binding.

FIG. 17, panels A-B shows the percent survival and weight loss of mice over time after intranasal administration of a single dose of exemplary compound LNA9.

FIG. 18, panels A-D, show the susceptibility of influenza virus to oseltamivir after serial passages under drug pressure.

FIG. 19, panels A-C, show the susceptibility of influenza virus to exemplary compound LNA9, including viruses after serial passages under drug pressure and drug resistant virus.

DEFINITIONS

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "effective amount" refers to that amount of a substance (e.g., an agent of interest) that produces some desired local or systemic effect. Effective amounts of active agents of interest vary depending on a variety of factors including, but not limited to, the weight and age of the subject, the condition being treated, the severity of the condition, the manner of administration and the like, and can readily be determined, e.g., determined empirically using data such as that data provided in the experimental section below.

The term "sample" as used herein relates to a material or mixture of materials, typically, although not necessarily, in fluid, i.e., aqueous, form, containing one or more components of interest. Samples may be derived from a variety of sources such as from a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Components in a sample are termed "analytes" herein. In many embodiments, the sample is a complex sample containing at least about $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $10^9$, $10^{10}$, $10^{11}$, $10^{12}$ or more species of analyte.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; nanobodies, and multispecific and multifunctional antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term "fusion protein" or grammatical equivalents thereof is meant a protein composed of a plurality of polypeptide components, that while typically unjoined in their native state, typically are joined by their respective amino and carboxyl termini through a linkage, e.g., a peptide linkage, to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. In addition, the term "protein" can further encompass the post-translational modification including but not limited to glycosylation, phosphorylation, methylation, and acetylation.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length.

The term "specific binding" refers to the ability of an agent to preferentially bind to a particular target (e.g., PSL2) that is present in a homogeneous mixture of different analytes. In some cases, a specific binding interaction will discriminate between desirable and undesirable analytes in a sample, typically more than about 10 to 100-fold or more (e.g., more than about 1000-fold). Specific binding can include hybridization, polypeptide-nucleic acid interactions or small molecule-nucleic acid interactions.

"Oligonucleotide" refers to ribose and/or deoxyribose nucleoside subunit polymers having between about 2 and about 200 contiguous subunits. The nucleoside subunits can be joined by a variety of intersubunit linkages, including, but not limited to, phosphodiester, phosphotriester, an alkylphosphonate, e.g., methylphosphonate, P3'→N5' phosphoramidate, N3'→P5' phosphoramidate, N3'→P5' thiophosphoramidate, phosphorodiamidate, and phosphorothioate linkages. In certain cases, intersubunit linkage has a chiral atom. Representative chiral intersubunit linkages include, but are not limited to, alkylphosphonates, phosphorodiamidates and phosphorothioates. Further, "oligonucleotides" includes chemical and biochemical modifications, such as those known to one skilled in the art, e.g., to the sugar (e.g., 2' substitutions), the base (see the definition of "nucleoside" below), and/or the 3' and 5' termini. In embodiments where the oligonucleotide moiety includes a plurality of intersubunit linkages, each linkage may be formed using the same chemistry or a mixture of linkage chemistries may be used. In embodiments where the oligonucleotide moiety includes a plurality of intersubunit linkages, one or more of the linkages may be chiral. Linkages having a chiral atom can be prepared as racemic mixtures, or as separate enantiomers. The terms "oligonucleotide", "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

A "bicyclic nucleic acid" or a "bridged nucleic acid" (BNA) refers to a modified RNA nucleotide where the ribose moiety is modified with an extra bridge connecting the 2' oxygen and 4' carbon, thereby forming a bicyclic ring system. BNA monomers can contain a five-membered, six-membered or a seven-membered bridge structure with a fixed 3'-endo conformation. Bridged nucleic acids include without limitation, locked nucleic acids (LNA), ethylene-bridged nucleic acids (ENA) and constrained ethyl (cEt).

A "bridge" refers to a chain of atoms or a valence bond connecting two bridgeheads, where a "bridgehead" is any skeletal atom of a ring system (e.g., the ribose ring system) which is bonded to three or more skeletal atoms (excluding hydrogen). In some embodiments, the bridge in a BNA has 7-12 ring members and 1-4 heteroatoms independently selected from nitrogen, oxygen, or sulfur. Unless otherwise specified, a BNA is optionally substituted with one or more substituents, e.g., including, but not limited to alkyl, substituted alkyl, alkoxy, substituted alkoxy, hydroxy, amino and halogen.

A "Locked nucleic acid" (LNA) is a modified RNA nucleotide where the ribose moiety is modified with an extra bridge connecting the 2' oxygen and 4' carbon, thereby forming a bicyclic ring system. The bridge "locks" the ribose in the 3'-endo conformation, which is often found in the A-form duplexes. Locked nucleic acids are also encompassed by the term "bicyclic nucleic acids" or "bridged nucleic acids" (BNA). LNA nucleotides can be mixed with any convenient nucleotides or nucleotide analogs, such as DNA or RNA residues in an oligonucleotide whenever desired. LNA's hybridize with DNA or RNA according to Watson-Crick base-pairing rules. Such oligomers can be synthesized chemically. In general, the locked ribose conformation enhances base stacking and backbone pre-organization to increase the hybridization properties (melting temperature) of the oligonucleotide.

An "ethylene-bridged nucleic acid" (ENA) refers to an LNA modified RNA nucleotide where the ribose moiety is modified with an extra bridge containing two carbon atoms between the 2' oxygen and the 4' carbon (see, e.g., Morita et al., Bioorganic Medicinal Chemistry, 2003, 11(10), 2211-2226). Ethylene-bridged nucleic acids are also encompassed by the term "bicyclic nucleic acids" or "bridged nucleic acids" (BNA).

A "constrained ethyl (cEt)" refers to an LNA modified RNA nucleotide where the ribose moiety is modified with an extra bridge connecting the 2' oxygen and 4' carbon, wherein the carbon atom of the bridge includes a methyl group. In some cases, the cEt is (S)-constrained ethyl. In other cases, the cEt is (R)-constrained ethyl (see, e.g., Pallan et al., Chem. Commun. (Camb)., 2012, 48(66), 8195-8197). Constrained ethyl nucleic acids are also encompassed by the term "bicyclic nucleic acids" or "bridged nucleic acids" (BNA).

As used herein, the term "2'-modified" or "2'-substituted" means a sugar comprising a substituent at the 2'-position other than H or OH. 2'-modified nucleotides, include moieties with 2' substituents selected from alkyl, allyl, amino, azido, fluoro, thio, O-alkyl, e.g., O-methyl, O-allyl, $OCF_3$, $O-(CH_2)_2-O-CH_3$ (e.g., 2'-O-methoxyethyl (MOE)), $O-(CH_2)_2SCH_3$, $-(CH_2)_2-ONR_2$, and $O-CH_2C(O)-NR_2$, where each R is independently selected from H, alkyl, and substituted alkyl.

The disclosure encompasses isolated or substantially purified nucleic acid nucleic acid molecules and compositions containing those molecules. In the context of the present disclosure, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present disclosure. By "fragment" or "portion" is meant a full length or less than full length of the nucleotide sequence. The siRNAs of the present disclosure can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

The term "lipid" is used broadly herein to encompass substances that are soluble in organic solvents, but sparingly soluble, if at all, in water. The term lipid includes, but is not limited to, hydrocarbons, oils, fats (such as fatty acids, glycerides), sterols, steroids and derivative forms of these compounds. Preferred lipids are fatty acids and their derivatives, hydrocarbons and their derivatives, and sterols, such as cholesterol. As used herein, the term lipid also includes amphipathic compounds which contain both lipid and hydrophilic moieties. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty amides produced by the conjugation reactions, e.g., with a modified terminal of an oligonucleotide.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Methods for Inhibiting Influenza a Virus

As summarized above, aspects of the present disclosure include pan-genotypic compositions designed to disrupt an RNA structural element of IAV, called Packaging Stem-Loop 2 (PSL2), within the 5' packaging signal region of genome segment PB2. By "pan-genotypic" is meant the compositions are effective across a variety of different types of IAV where the PSL2 structural element is conserved. In some cases, the subject compositions can be referred to as broad spectrum. As used herein, the term "broad spectrum" refers to the anti-viral activity of a single moiety that is active against two or more different viruses, such as three or more, four or more, five or more, six or more, eight or more, 10 or more different viruses. The two or more different viruses may be selected from different virus sub-groups (e.g., Influenza A group 1 or Influenza A group 2), or may be selected from within the same group (e.g., two or more of H1, H2, H5, H6, H8 and H9 group 1 influenza A viruses, or two or more of H3, H4, H7 and H10 Group 2 Influenza A viruses).

Figure 4:
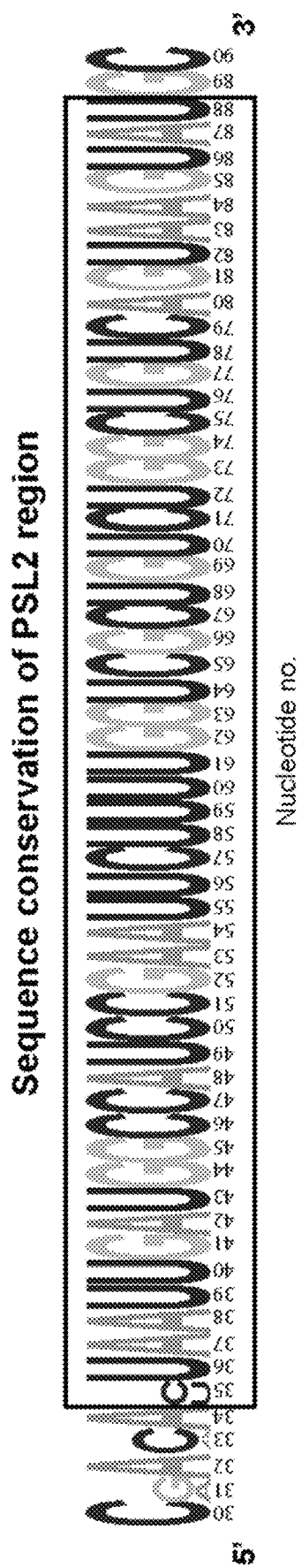

Disruption of PSL2 structure dramatically inhibits IAV. PSL2 is conserved across all tested influenza A subtypes. FIG. 1, panel a, shows an example of the PSL2 structure that can be targeted in the subject methods. FIG. 4 illustrates the conservancy of nucleotide sequences of interest containing the PSL2 structure. In some cases, the subject compositions have broad spectrum activity against IAVs, such as activity against 2 or more IAVs selected from H1N1, H3N2 and H5N.

Aspects of the present disclosure include methods for inhibiting influenza A virus (IAV) in a sample. In some embodiments, the method includes contacting a sample comprising viral RNA (vRNA) having a PSL2 motif with an effective amount of an agent that specifically binds the PSL2 motif to inhibit the influenza A virus. In some cases, the sample is in vitro. In certain cases, the sample is in vivo. The vRNA in the sample can be comprised in a virion. In some cases, the vRNA is comprised in a cell, such as a cell infected with the virus particle.

Aspects of the present disclosure include methods for inhibiting influenza A virus (IAV) in a cell. In some embodiments, the method includes contacting a cell comprising viral RNA (vRNA) having a PSL2 motif with an effective amount of an agent that specifically binds the PSL2 motif to inhibit the influenza A virus. In some cases, the cell is in vitro. In certain cases, the cell is in vivo.

Figure 14:
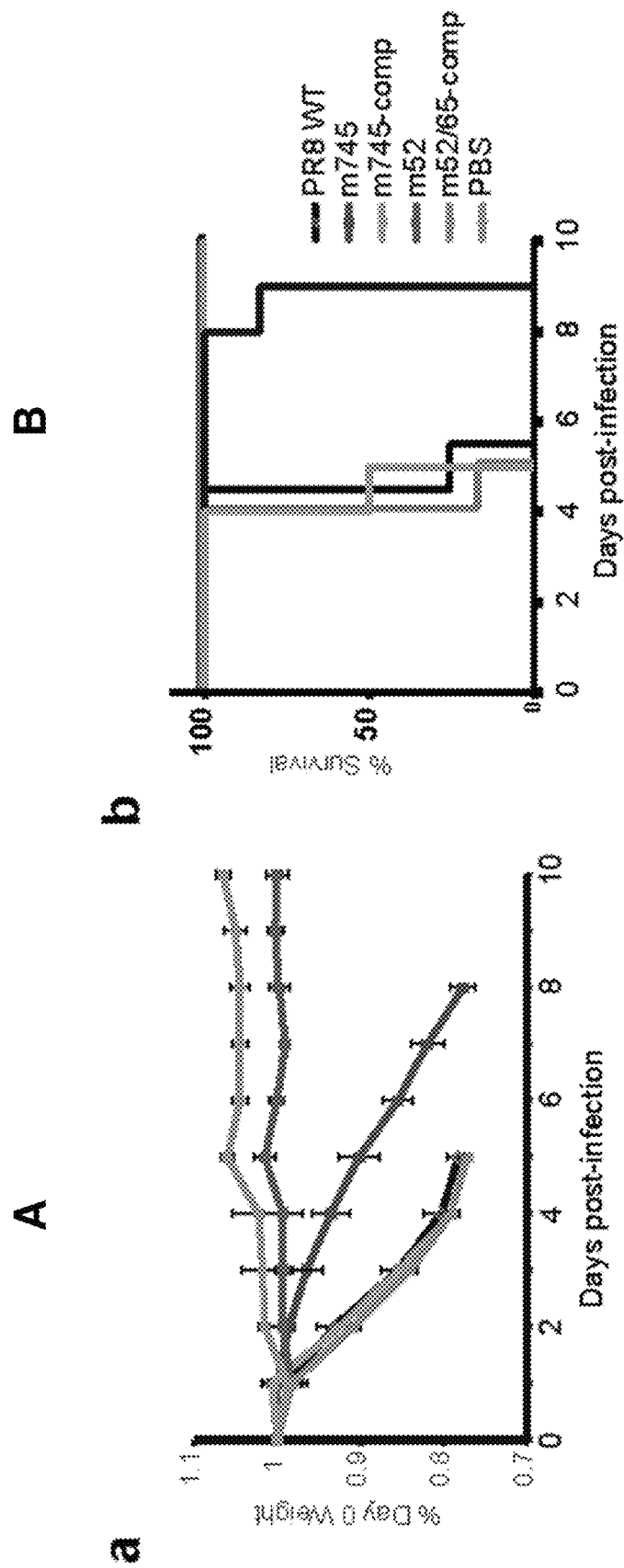

In some embodiments, the vRNA in the sample (e.g., cell) comprises PB2 vRNA. As used here, by "PB2 vRNA" is meant viral RNA (e.g., IAV RNA) that includes the conserved RNA structural element called Packaging Stem-Loop 2 (PSL2). The agent can bind to particular sites of the PSL2 motif to disrupt the overall structure of the vRNA thereby inhibiting the virus (see e.g., FIG. 14). In some cases, the agent inhibits the packaging ability of the vRNA, thereby inhibiting the virus. For example, FIG. 1 illustrates RNA secondary structures of wild-type PB2 and packaging mutant vRNAs.

In some embodiments, contacting the sample (e.g., cell) with an agent results in 1 $\log_{10}$ or more titer deficits of the virus, such as 1.5 or more, 2 or more, 2.5 or more, 3 or more, 3.5 or more, 4 or more, 5 or more, 6 or more, 7 or more, 8 or more, 9 or more, 10 $\log_{10}$ or even more titer deficits of the virus.

In some embodiments, contacting the sample (e.g., cell) with an agent results in 2 $\log_{10}$ or more titer deficits of the virus, such as 2.5 or more, 3 or more, 3.5 or more, 4 or more, 5 or more, 6 or more, 7 or more, 8 or more, 9 or more, 10 $\log_{10}$ or even more titer deficits of the virus. In some embodiments, the agent is an oligonucleotide compound (e.g., as described herein) comprising a sequence complementary to a PSL2 motif of the vRNA, or a salt thereof.

In some instances of the methods, binding (e.g., via hybridization) of the oligonucleotide compound (e.g., one of the sequences described above) to the region of PB2 vRNA disrupts the overall secondary RNA structure of the PB2 vRNA. In some cases, binding of the oligonucleotide compound inhibits the packaging ability of the PB2 vRNA, thereby inhibiting the virus. In some cases, the subject compound targets at least part of the region defined by nucleotides 34-87 in the (−)-sense notation of the 5' terminal coding region of the PB2 vRNA. In some cases, the compound targets at least part of the region defined by nucleotides 1-14 in the (−)-sense notation of the 5' terminal coding region of the PB2 vRNA. In some instances of the methods, the method further includes recruiting an RNase to the PSL2 to degrade the vRNA.

Aspects of the present disclosure include a method of treating or preventing influenza A virus infection in a subject. In some embodiments, the method comprises administering to a subject in need thereof a pharmaceutical composition comprising an effective amount of an active agent that binds to a PSL2 motif of a viral RNA (vRNA) (e.g., as described herein). As such, in some cases, the subject is one who has been infected with the virus. In certain cases, the subject is one who is at risk of being infected, or is suspected of being infected with the virus. In some embodiments, the vRNA is a PB2 vRNA.

Any convenient protocol for administering the agent to a subject may be employed. The particular protocol that is employed may vary, e.g., depending on the site of administration and whether the agents are e.g., oligonucleotides, antibodies, proteins, peptides or small molecules. For in vivo protocols, any convenient administration protocol may be employed. Depending upon the identity and binding affinity of the agent, the response desired, the manner of administration, e.g. locally or systemic, intraocular, periocular, retrobalbar, intramuscular, intravenous, intraperitoneal, subcutaneous, subconjunctival, intranasal, topical, eye drops, i.v. s.c., i.p., oral, and the like, the half-life, the number of cells or size of the graft bed or transplanted tissue, various protocols may be employed. In some cases, the agent is administered nasally. In some cases, the agent is administered as an aerosol. In certain cases, the agent is administered by a nebulizer. In certain cases, the agent is administered via the assistance of breathing-assisting devices including but not limited to non-invasive positive pressure ventilation or mechanical ventilation In certain cases, the agent is administered intravenously. In certain other cases, the agent is administered subcutaneously. In certain cases, the agent is administered by intramuscular injection.

Also provided are pharmaceutical compositions including the subject agents. Any convenient excipients, carriers, etc. can be utilized in the compositions. Pharmaceutically acceptable carriers that find use in the compositions may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. The agent composition may also be lyophilized, for subsequent reconstitution and use. The composition can also include a carrier as described here. Examples of carriers which may be used include, but are not limited to, alum, microparticles, liposomes, and nanoparticles. Any convenient additives can be included in the subject compositions to enhance the delivery of the subject active agent. Additives of interest include, cellular uptake enhancers, carrier proteins, lipids, dendrimer carriers, carbohydrates, and the like.

In some cases, the pharmaceutical composition further includes one or more additional active agents. Active agents of interest include an additional oligonucleotide compound of the present disclosure and any convenient antiviral compounds or drugs of interest. including but not limited to Amantadine, Rimantadine, Zanamivir, Oseltamivir, Peramivir and the like.

Agents

Any convenient agents may be utilized as an agent of a target of interest (e.g., PSL2) in the subject methods and compositions. Agents of interest include, but are not limited to, a ligand of PSL-2, a PSL2-binding antibody, a scaffolded protein binder of PSL2, an oligonucleotide, a small molecule, and a peptide; or a fragment, variant, or derivative thereof; or combinations of any of the foregoing.

Antibodies that may be used as agents in connection with the present disclosure can encompass, but are not limited to, monoclonal antibodies, polyclonal antibodies, bispecific antibodies, Fab antibody fragments, F(ab)$_2$ antibody fragments, Fv antibody fragments (e.g., $V_H$ or $V_L$), single chain Fv antibody fragments and dsFv antibody fragments. Furthermore, the antibody molecules may be fully human antibodies, humanized antibodies, or chimeric antibodies. The antibodies that may be used in connection with the present disclosure can include any antibody variable region, mature or unprocessed, linked to any immunoglobulin constant region. Minor variations in the amino acid sequences of antibodies or immunoglobulin molecules are encompassed by the present disclosure, providing that the variations in the amino acid sequence maintain 75% or more, e.g., 80% or more, 90% or more, 95% or more, or 99% or more of the sequence. In particular, conservative amino acid replacements are contemplated. Conservative replacements are those that take place within a family of amino acids that are related in their side chains. Whether an amino acid change results in a functional peptide can be determined by assaying the specific activity of the polypeptide derivative. In some embodiments, the agent is an antibody fragment (e.g., as described herein).

In some embodiments, the agent is a scaffolded polypeptide binder. A scaffold refers to an underlying peptidic framework (e.g., a consensus sequence or structural motif) from which a polypeptide agent arose. The underlying scaffold sequence includes those residues that are fixed and variant residues that may confer on the resulting polypeptide agents different functions, such as specific binding to a target receptor. Such structural motifs may be characterized and compared structurally as a combination of particular secondary and tertiary structural elements, or alternatively, as a comparable primary sequence of amino acid residues. Any convenient scaffolds and scaffolded polypeptides may be utilized as agents in the subject methods. In some embodiments, such agents may be identified utilizing a recombinant screening method such as phage display screening. Scaffolded polypeptide binders of interest include, but are not limited to, synthetic small proteins and recombinant small proteins such as Affibodies.

In some cases, the agent is a small molecule that binds PSL2. Small molecules of interest include, but are not limited to, small organic or inorganic compounds having a molecular weight (MW) of more than 50 and less than about 2,500 daltons (Da), such as more than 50 and less than about 1000 Da, or more than 50 and less than about 500 Da. "Small molecules" encompasses numerous biological and chemical classes, including synthetic, semi-synthetic, or naturally-occurring inorganic or organic molecules, including synthetic, recombinant or naturally-occurring polypeptides and nucleic acids. Small molecules of interest can comprise functional groups necessary for structural interaction with proteins, particularly hydrogen bonding, and can include at least an amine, carbonyl, hydroxyl or carboxyl group, and can contain at least two of the functional chemical groups. The small molecules can comprise cyclical carbon or heterocyclic structures and/or aromatic or polyaromatic structures substituted with one or more of the above functional groups. Small molecules are also found among biomolecules including peptides, saccharides, fatty acids, steroids, purines, pyrimidines, derivatives, structural analogs or combinations thereof.

Oligonucleotide Compounds

In some embodiments, the agent is an oligonucleotide or derivative thereof, or a salt thereof (e.g., a pharmaceutically acceptable salt). In some instances, the oligonucleotide in complementary to a particular segment of the PSL2 motif (e.g., as described herein). Complementary oligonucleotides that find use in the subject methods will in some cases be at least 5, such at least 6, at least 7 at least 8, at least 9, at least 10, at least 11, about 12, at least 13, at least 14, at least 15, or even more. In some cases, the complementary oligonucleotide is 75 nucleotides or less in length, such as 50 nucleotides or less in length, 45 nucleotides or less in length, 40 nucleotides or less in length, or 35 nucleotides or less in length, where the length is governed by efficiency of inhibition, specificity, including absence of cross-reactivity, and the like. In some cases, the complementary oligonucleotide is 30 nucleotides or less in length, such as 25 nucleotides or less in length, 20 nucleotides or less in length, or 15 nucleotides or less in length, where the length is governed by efficiency of inhibition, specificity, including absence of cross-reactivity, and the like. The present disclosure provides for short oligonucleotides, e.g., of from 7, 8 to 15, or 15 to 16 nucleotides in length, can be strong and selective inhibitors of PSL2 function. In some embodiments, the active agent is a compound comprising an oligonucleotide sequence comprising at least 8 nucleoside subunits complementary to the region of PB2 vRNA. In some embodiments, the active agent is a compound comprising an oligonucleotide sequence comprising at least 8 and 20 or less (e.g., 15 or less) nucleoside subunits complementary to the region of PB2 vRNA.

A specific region or regions of the endogenous strand PSL2 sequence is chosen to be complemented by the oligonucleotide agent. Selection of a specific sequence for the oligonucleotide may use an empirical method, where based on the structural analysis (e.g., as described herein) several candidate sequences are assayed for inhibition of the target IAV in an in vitro or animal model. A combination of oligonucleotides and sequences may also be used, where several regions of the target PSL2 are selected for antisense complementation.

In some embodiments, the agent is an oligonucleotide compound comprising at least 5 nucleoside subunits (e.g., at least 6, at least 7, at least 8, at least 9, at least 10, at least 12, at least 14, at least 16, at least 18, or at least 20) complementary to a PSL2 motif of a vRNA, or a salt thereof. In certain cases, the linkages of the oligonucleotides are modified phosphate groups, e.g., where one or more oxygens of phosphate has been replaced with a different substituent. Without being bound to any particular theory, such modification can increase resistance of the oligonucleotide to nucleolytic breakdown. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. In some cases, the linkages of the oligonucleotides are modified phosphate groups where one or more of the non-bridging phosphonate oxygen atoms in the linkage has been replaced by a group selected from, S, Se, $BR^a_3$, alkyl, substituted alkyl, aryl, substituted aryl, H, $NR^a_2$, or $OR^b$, where $R^a$ is H, alkyl, substituted alkyl, aryl, substituted aryl, and $R^b$ is H, alkyl, substituted alkyl, aryl or substituted aryl. In certain cases, one or more of the linkages of the oligonucleotide the phosphorous atom is chiral, e.g., a stereogenic center. The stereogenic phosphorus atom can possess either the "R" configuration (referred to herein as Rp), or the "S" configuration (referred to herein as Sp). In certain embodiments, the linkages of the oligonucleotide include one or more stereogenic phosphorus atoms with at least 1%, 5%, 10%, 20%, 30%, 40%, 50%, 60%, 70%, 80%, 90%, 95%, or more enantiomeric excess of the Sp configuration. In certain other, the linkages of the oligonucleotide include one or more stereogenic phosphorus atoms with at least 1%, 5%, 10%, 20%, 30%, 40%, 50%, 60%, 70%, 80%, 90%, 95%, or more enantiomeric excess of the Rp configuration.

In certain embodiments, one or more of the linkages of the oligonucleotide are selected from methylphosphonate, P3'→N5' phosphoramidate, N3'→P5' phosphoramidate, N3'→P5' thiophosphoramidate, phosphorodithioate and phosphorothioate linkages. In certain cases, one or more linkages of the oligonucleotide is a phosphorothioate linkage. In certain cases, the phosphorus atom in one or more of the phosphorothioate linkages is chiral. In some cases, the chiral phosphorus atom in the one or more phosphorothioate linkages has Rp configuration. In some cases, the chiral phosphorus atom in the one or more phosphorothioate linkages has Sp configuration. In certain embodiments, the linkages of the oligonucleotide include one or more phosphorothioate linkages with at least 1%, 5%, 10%, 20%, 30%, 40%, 50%, 60%, 70%, 80%, 90%, 95%, or more enantiomeric excess of the Sp configuration. In certain other embodiments, the linkages of the oligonucleotide includes one or more phosphorothioates with at least 1%, 5%, 10%, 20%, 30%, 40%, 50%, 60%, 70%, 80%, 90%, 95%, or more enantiomeric excess of the Rp configuration.

In certain instances, the oligonucleotide sequence is a bridged nucleic acid (e.g., as described herein). In certain instances, the oligonucleotide sequence includes one or more bridged nucleic acid nucleotides, such as 2 or more, 3 or more, 4 or more, 5 or more, 6 or more, 7 or more, 8 or more, 9 or more, 10 or more, or even more.

In certain instances, the oligonucleotide sequence is a locked nucleic acid. In certain instances, the oligonucleotide sequence includes one or more locked nucleic acid nucleotides, such as 2 or more, 3 or more, 4 or more, 5 or more, 6 or more, 7 or more, 8 or more, 9 or more, 10 or more, or even more.

In certain instances, the oligonucleotide sequence is an ethylene-bridged nucleic acid (ENA). In certain instances, the oligonucleotide sequence includes one or more ENA nucleotides, such as 2 or more, 3 or more, 4 or more, 5 or more, 6 or more, 7 or more, 8 or more, 9 or more, 10 or more, or even more.

In certain instances, the oligonucleotide sequence is constrained ethyl (cEt) nucleic acid. In certain instances, the oligonucleotide sequence includes one or more cEt nucleotides, such as 2 or more, 3 or more, 4 or more, 5 or more, 6 or more, 7 or more, 8 or more, 9 or more, 10 or more, or even more. In certain instances, the oligonucleotide sequence includes one or more (S)-constrained ethyl nucleic acids, such as 2 or more, 3 or more, 4 or more, 5 or more, 6 or more, 7 or more, 8 or more, 9 or more, 10 or more, or even more. In certain instances, the oligonucleotide sequence includes one or more (R)-constrained ethyl nucleic acids, such as 2 or more, 3 or more, 4 or more, 5 or more, 6 or more, 7 or more, 8 or more, 9 or more, 10 or more, or even more. In certain instances, the oligonucleotide sequence includes one or more ribose modifications. In some cases, the oligonucleotide sequence includes one or more 2'-modified ribose sugars (also referred to herein as 2'-modified nucleotides). In certain instances, the oligonucleotide sequence includes one or more 2'-modified nucleotides, such as 2 or more, 3 or more, 4 or more, 5 or more, 6 or more, 7 or more, 8 or more, 9 or more, 10 or more, or even more. 2'-modified nucleotides, include, but are not limited to moieties with 2' substituents selected from alkyl, allyl, amino, azido, fluoro, thio, O-alkyl, e.g., O-methyl, O-allyl, $OCF_3$, O—$(CH_2)_2$—O—$CH_3$ (e.g., 2'-O-methoxyethyl (MOE)), O—$(CH_2)_2SCH_3$,)—$(CH_2)_2$—$ONR_2$, and O—$CH_2C(O)$—$NR_2$, where each R is independently selected from H, alkyl, and substituted alkyl. In certain instances, the oligonucleotide sequence includes one or more 2'-O-methoxyethyl (MOE) modifications, such as 2 or more, 3 or more, 4 or more, 5 or more, 6 or more, 7 or more, 8 or more, 9 or more, 10 or more, or even more.

In some embodiments, the agent is an oligonucleotide that comprises at least 5 deoxyribonucleotide units (e.g., units complementary to a PSL2 motif) (e.g., least 6, at least 7, at least 8, at least 9, at least 10, at least 12, at least 14, at least 16, at least 18, at least 20) and is capable of recruiting an RNase. In some case, the oligonucleotide recruits an RNase to catalyze the degradation of the target vRNA into smaller components. Any convenient methods and moieties for recruiting an RNase can be incorporated into the subject agents (e.g., oligonucleotides). In some instances, the oligonucleotide agent further includes a sequence that recruits an RNase of interest. It is understood that unless indicated otherwise, an oligonucleotide sequence as depicted herein is meant to include DNA sequences, RNA sequences (e.g., where U can optionally replace T). mixed RNA/DNA sequences, and analogs thereof, including analogs where one or more nucleotides of the sequence are modified nucleotides, such as BNA analogs, LNA analogs, ENA analogs, cEt analogs, 2'-modified analogs, and/or analogs where one or more internucleoside linkages are replaced, e.g., with a non-naturally occurring linkage such as a phosphorothioate, phosphoroclithioate, phosphoramidate or thiophosphoramidate linkage. It will be understood that in embodiments where one or more of the linkages of the oligonucleotide include a chiral phosphorous atom, e.g., a stereogenic center, the stereogenic phosphorus atom can possess either the "R" configuration (referred to herein as Rp), or the "S" configuration (referred to herein as Sp).

In some embodiments, the oligonucleotide comprises a sequence selected from:

```
                           (SEQ ID NO: 45)
5' ACCAAAAGAAT 3';

(SEQ ID NO: 46)
5' TGGCCATCAAT 3';

(SEQ ID NO: 47)
5' TAGCATACTTA 3';

(SEQ ID NO: 48)
5' CCAAAAGA 3';

(SEQ ID NO: 49)
5' CATACTTA 3';

(SEQ ID NO: 50)
5' CAGACACGACCAAAA 3';

(SEQ ID NO: 51)
5' TACTTACTGACAGCC 3';

(SEQ ID NO: 52)
5' AGACACGACCAAAAG 3';

(SEQ ID NO: 53)
5' ACCAAAAGAAT 3';

(SEQ ID NO: 54)
5' TGGCCATCAAT 3';

(SEQ ID NO: 55)
5' TAGCATACTTA 3';

(SEQ ID NO: 56)
5' CGACCAAAAGAATTC 3';

(SEQ ID NO: 57)
5' CGACCAAAAGAATTC 3';

(SEQ ID NO: 58)
5' GATGGCCATCAATTA 3';

(SEQ ID NO: 59)
5' GATGGCCATCAATTA 3';

(SEQ ID NO: 60)
5' TCTAGCATACTTACT 3';

(SEQ ID NO: 61)
5' TCTAGCATACTTACT 3';

(SEQ ID NO: 62)
5' GAATTCGGATGGCCA 3';

(SEQ ID NO: 63)
5' GGCCATCAATTAGTG 3';

(SEQ ID NO: 64)
5' TTCGGATGGCCATCA 3';

(SEQ ID NO: 65)
5' AGCCAGACAGCGA 3';
and
                           (SEQ ID NO: 66)
5' GACAGCCAGACAGCA 3'.
```

In certain embodiments, the oligonucleotide comprises the sequence: 5' ACCAAAAGAAT 3' (SEQ ID NO:45). In certain embodiments, the oligonucleotide comprises the sequence: 5' TGGCCATCAAT 3' (SEQ ID NO:46). In certain embodiments, the oligonucleotide comprises the sequence: 5' TAGCATACTTA 3' (SEQ ID NO:47). In certain embodiments, the oligonucleotide comprises the sequence: 5' CCAAAAGA 3' (SEQ ID NO:48). In certain embodiments, the oligonucleotide comprises the sequence: 5' CATACTTA 3' (SEQ ID NO:49). In certain embodiments, the oligonucleotide comprises the sequence: 5' CAGACACGACCAAAA 3' (SEQ ID NO:50). In certain embodiments, the oligonucleotide comprises the sequence: 5' TACTTACTGACAGCC 3' (SEQ ID NO:51). In certain embodiments, the oligonucleotide comprises the sequence: 5' AGACACGACCAAAAG 3' (SEQ ID NO:52). In certain embodiments, the oligonucleotide comprises the sequence: 5' ACCAAAAGAAT 3' (SEQ ID NO:53). In certain embodiments, the oligonucleotide comprises the sequence: 5' TGGCCATCAAT 3' (SEQ ID NO:54). In certain embodiments, the oligonucleotide comprises the sequence: 5' TAGCATACTTA 3' (SEQ ID NO:55). In certain embodiments, the oligonucleotide comprises the sequence: 5' CGACCAAAAGAATTC 3' (SEQ ID NO:56). In certain embodiments, the oligonucleotide comprises the sequence: 5' CGACCAAAAGAATTC 3' (SEQ ID NO:57). In certain embodiments, the oligonucleotide comprises the sequence: 5' GATGGCCATCAATTA 3' (SEQ ID NO:58). In certain embodiments, the oligonucleotide comprises the sequence: 5' GATGGCCATCAATTA 3' (SEQ ID NO:59). In certain embodiments, the oligonucleotide comprises the sequence: 5' TCTAGCATACTTACT 3' (SEQ ID NO:60). In certain embodiments, the oligonucleotide comprises the sequence: 5' TCTAGCATACTTACT 3' (SEQ ID NO:61). In certain embodiments, the oligonucleotide comprises the sequence: 5' GAATTCGGATGGCCA 3' (SEQ ID NO:62). In certain embodiments, the oligonucleotide comprises the sequence: 5' GGCCATCAATTAGTG 3' (SEQ ID NO:63). In certain embodiments, the oligonucleotide comprises the sequence:5' TTCGGATGGCCATCA 3' (SEQ ID NO:64). In certain embodiments, the oligonucleotide comprises the sequence: 5' AGCCAGACAGCGA 3' (SEQ ID NO:65). In certain embodiments, the oligonucleotide comprises the sequence: 5' GACAGCCAGACAGCA 3' (SEQ ID NO:66).

In some embodiments, the oligonucleotide comprises a sequence selected from:

```
                            (SEQ ID NO: 98)
5'CGACCAAAAGAATT 3';
and
                            (SEQ ID NO: 99)
5'GACCAAAAGAATTCGG 3'.
```

In certain embodiments, the oligonucleotide comprises the sequence: 5'CGACCAAAAGAATT 3' (SEQ ID NO:98). In certain embodiments, the oligonucleotide comprises the sequence: 5'GACCAAAAGAATTCGG 3' (SEQ ID NO:99).

In some embodiments, the oligonucleotide comprises a sequence selected from:

```
                            (SEQ ID NO: 100)
5' AGCATACTTACTGACA 3';

(SEQ ID NO: 101)
5' CATACTTACTGACA 3';

(SEQ ID NO: 102)
5' ATACTTACTGACAG 3';

(SEQ ID NO: 103)
5' CATACTTACTGACAGC 3';

(SEQ ID NO: 104)
5' AGACAGCGACCAAAAG 3';
and
                            (SEQ ID NO: 105)
5' ACAGCGACCAAAAG.
```

In certain embodiments, the oligonucleotide comprises the sequence: 5' AGCATACTTACTGACA 3' (SEQ ID NO:100). In certain embodiments, the oligonucleotide comprises the sequence: 5' CATACTTACTGACA 3' (SEQ ID NO:101). In certain embodiments, the oligonucleotide comprises the sequence: 5' ATACTTACTGACAG 3' (SEQ ID NO: 102). In certain embodiments, the oligonucleotide comprises the sequence5' CATACTTACTGACAGC 3' (SEQ ID NO: 103). In certain embodiments, the oligonucleotide comprises the sequence: 5' AGACAGCGACCAAAAG 3' (SEQ ID NO: 104). In certain embodiments, the oligonucleotide comprises the sequence: 5' ACAGCGACCAAAAG (SEQ ID NO: 105).

In some embodiments, the oligonucleotide comprises a sequence selected from:

```
                            (SEQ ID NO: 106)
5'CAGCCAGACAGCGAC 3';

(SEQ ID NO: 107)
5'CAGCCAGACAGCGA 3';

(SEQ ID NO: 108)
5'ACAGCCAGACAGCGA 3';
and
                            (SEQ ID NO: 109)
5'GACAGCCAGACAGCG 3'.
```

In certain embodiments, the oligonucleotide comprises the sequence: 5'CAGCCAGACAGCGAC 3' (SEQ ID NO:106). In certain embodiments, the oligonucleotide comprises the sequence: 5'CAGCCAGACAGCGA 3' (SEQ ID NO:107). In certain embodiments, the oligonucleotide comprises the sequence: 5'ACAGCCAGACAGCGA 3' (SEQ ID NO:108). In certain embodiments, the oligonucleotide comprises the sequence: 5'GACAGCCAGACAGCG 3' (SEQ ID NO:109).

In some embodiments, the oligonucleotide comprises a sequence selected from:

```
                            (SEQ ID NO: 62)
5' GAATTCGGATGGCCA 3';

(SEQ ID NO: 65)
5' AGCCAGACAGCGA 3';

(SEQ ID NO: 110)
5' CATCAATTAGTGTCG 3';

(SEQ ID NO: 111)
5' CCATCAATTAGTGTCG 3';

(SEQ ID NO: 112)
5' GCCATCAATTAGTGTG 3';

(SEQ ID NO: 113)
5' AAGAATTCGGATGGC 3';

(SEQ ID NO: 114)
5' CAGACAGCGACCAA 3';
and
                            (SEQ ID NO: 115)
5' TGACAGCCAGACAGC 3'.
```

In certain embodiments, the oligonucleotide comprises the sequence: 5' GAATTCGGATGGCCA 3' (SEQ ID NO:62). In certain embodiments, the oligonucleotide comprises the sequence: 5' AGCCAGACAGCGA 3' (SEQ ID NO:65). In certain embodiments, the oligonucleotide comprises the sequence: 5' CATCAATTAGTGTCG 3' (SEQ ID NO:110). In certain embodiments, the oligonucleotide comprises the sequence: 5' CCATCAATTAGTGTCG 3' (SEQ ID NO:111). In certain embodiments, the oligonucleotide comprises the sequence: 5' GCCATCAATTAGTGTG 3' (SEQ ID NO:112). In certain embodiments, the oligonucleotide comprises the sequence: 5' AAGAATTCGGATGGC 3' (SEQ ID NO:113). In certain embodiments, the oligonucleotide comprises the sequence: 5' CAGACAGCGACCAA 3' (SEQ ID NO:114). In certain embodiments, the oligonucleotide comprises the sequence: 5' TGACAGCCAGACAGC 3' (SEQ ID NO:115). In some instances, binding (e.g., via hybridization) of the oligonucleotide compound (e.g., one of the sequences described above) to the region of PB2 vRNA disrupts the overall secondary RNA structure of the PB2 vRNA. In certain cases, binding of the oligonucleotide compound to the region -continued LNA 2:
(SEQ ID NO: 68)
5' TggCcATcaaT 3';

LNA 3:
(SEQ ID NO: 69)
5' TagCAtActtA 3';

LNA 4:
(SEQ ID NO: 70)
5' CCAAAAGA 3';

LNA 5:
(SEQ ID NO: 71)
5' CATACTTA 3';

LNA 6:
(SEQ ID NO: 72)
5' CagaCaCGaCCaaAA 3';

LNA 7:
(SEQ ID NO: 73)
5' TAcTtaCTgaCagCC 3';

LNA 8:
(SEQ ID NO: 74)
5' AGACacgaccaAAAG 3';

LNA 9:
(SEQ ID NO: 75)
5' TACTtactgacaGCC 3';

LNA9.2:
(SEQ ID NO: 76)
5' TACttactgacAGCC 3';

LNA10:
(SEQ ID NO: 77)
5' ACCaaaagAAT 3';

LNA11:
(SEQ ID NO: 78)
5' TGGccatcAAT 3';

LNA12:
(SEQ ID NO: 79)
5' TAGcatacTTA 3';

LNA13:
(SEQ ID NO: 80)
5' CgacCAaaAGaattC 3';

LNA14:
(SEQ ID NO: 81)
5' CGACcaaaagaATTC 3';

LNA15:
(SEQ ID NO: 82)
5' GaTGgCcATcaAttA 3';

LNA16:
(SEQ ID NO: 83)
5' GATGgccatcaATTA 3';

LNA17:
(SEQ ID NO: 84)
5' TcTAgCaTActTacT 3';

LNA18:
(SEQ ID NO: 85)
5' TCTAgcatactTACT 3';

LNA19:
(SEQ ID NO: 86)
5' GAAttcggatgGCCA 3';

LNA20:
(SEQ ID NO: 87)
5' GGCCatcaattaGTG 3';

-continued

LNA21:
(SEQ ID NO: 88)
5' TTCGgatggccaTCA 3';

LNA22:
(SEQ ID NO: 89)
5' AGCCagacagCGA 3';
and

LNA23:
(SEQ ID NO: 90)
5' GACAgccagacaGCA 3'.

It will be understood that for any of the sequences LNA1-LNA23 (SEQ ID NO: 67)-(SEQ ID NO: 90), one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain embodiments, the oligonucleotide has one of the following sequences where capitalized letters denote LNA nucleotides and lowercase letters denote DNA nucleotides (i.e., deoxyribonucleotide units):

LNA19:
(SEQ ID NO: 86)
5'GAAttcggatgGCCA 3';

LNA22:
(SEQ ID NO: 89)
5'AGCCagacagCGA 3';

LNA22.2:
(SEQ ID NO: 116)
5'CAGCcagacagCGAC 3';

LNA22.3:
(SEQ ID NO: 117)
5'CAGccagacagCGAC 3';

LNA22.5:
(SEQ ID NO: 118)
5'CAGccagacaGCGA 3';

LNA22.6:
(SEQ ID NO: 119)
5'CAGccagacagCGA 3';

LNA22.7:
(SEQ ID NO: 120)
5'CAGCcagacagCGA 3';

LNA22.8:
(SEQ ID NO: 121)
5'ACAgccagacagCGA 3';

LNA22.9:
(SEQ ID NO: 122)
5'ACAGccagacaGCGA 3';

LNA22.10:
(SEQ ID NO: 123)
5'ACAgccagacaGCGA 3';

LNA22.11:
(SEQ ID NO: 124)
5'GACAgccagacaGCG 3';

-continued

LNA22.13:
(SEQ ID NO: 125)
5'GACagccagacaGCG 3';
and

LNA22.14:
(SEQ ID NO: 126)
5'GACagccagacAGCG.

It will be understood that for any of the sequences LNA19, or LNA22-LNA22.14 ((SEQ ID NO: 86); (SEQ ID NO: 89); and (SEQ ID NO:116)-(SEQ ID NO:126)), one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain embodiments, the oligonucleotide has one of the following sequences where capitalized letters denote LNA nucleotides and lowercase letters denote DNA nucleotides (i.e., deoxyribonucleotide units):

LNA24:
(SEQ ID NO: 127)
5'CATcaattagtgTCG 3';

LNA25:
(SEQ ID NO: 128)
5'CCAtcaattagtgTCG 3';

LNA26:
(SEQ ID NO: 129)
5'GCCatcaattagtGTG 3';

LNA27:
(SEQ ID NO: 130)
5'AAGAattcggaTGGC 3';

LNA28:
(SEQ ID NO: 131)
5'CAGacagcgacCAA 3';
and

LNA29:
(SEQ ID NO: 132)
5'TGAcagccagacAGC 3'.

It will be understood that for any of the sequences LNA24, or LNA29 (SEQ ID NO: 127)-(SEQ ID NO: 132), one or more of the LNA nucleotides can be replaced with a modified nucleotide selected from BNA nucleotides, ENA nucleotides, cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain embodiments, the oligonucleotide has the sequence LNA14, or a derivative thereof, as shown in Table 1, where a "+" before the letter denotes LNA nucleotides, or other chemically modified nucleotides (e.g., as described herein), and other letters denote DNA nucleotides (i.e., deoxyribonucleotide units):

TABLE 1

LNA14 derivatives

| NAME | SEQUENCE | SEQ ID NO: |
|---|---|---|
| LNA14.1 | +G+C+G+ACCAAAAGA+A+T+T | 133 |
| LNA14.2 | +G+C+G+ACCAAAAG+A+A+T+T | 134 |
| LNA14.5 | +C+G+A+CCAAAAGA+A+T+T | 135 |
| LNA14 | +C+G+A+CCAAAAGA+A+T+T+C | 81 |
| LNA14.7 | +C+G+ACCAAAAGA+A+T+T+C | 136 |
| LNA14.8 | +C+G+A+CCAAAAGAT+T+C | 137 |
| LNA14_9 | +C+G+ACCAAAAGAA+T+T+C | 138 |
| LNA14.10 | +G+A+CCAAAAGAA+T+T+C | 139 |
| LNA14.14 | +G+C+G+ACCAAAAGA+A+T+T+C | 140 |
| LNA14.15 | +G+C+GACCAAAAGA+A+T+T+C | 141 |
| LNA14.16 | +G+C+GACCAAAAGA+T+T+C | 142 |
| LNA14.17 | +C+G+ACCAAAAGAA+T+T+C+G | 143 |
| LNA14.19 | +C+G+A+CCAAAAGAA+T+T+C+G | 144 |
| LNA14.22 | +G+A+CCAAAAGAA+T+T+C | 145 |
| LNA14.24 | +A+C+C+AAAAGAA+T+T+C | 146 |
| LNA14.27 | +C+G+ACCAAAAGAAT+T+C+G+G | 147 |
| LNA14.28 | +G+A+CCAAAAGAAT+T+C+G+G | 148 |
| LNA14.30 | +G+A+C+CAAAAGAATT+C+G+G | 149 |
| LNA14.31 | +G+A+CCAAAAGAATT+C+G+G | 150 |
| LNA14.32 | +A+C+C+AAAAGAATT+C+G+G+A | 151 |
| LNA14.36 | +C+C+A+AAAGAATT+C+G+G+A | 152 |
| LNA14.37 | +C+A+A+AAGAATTC+G+G+A | 153 |
| LNA14.39 | +C+A+AAAGAATTC+G+G+A | 154 |
| LNA14.40 | +C+C+AAAAGAATTCG+G+A+T | 155 |
| LNA14.42 | +C+C+A+AAAGAATTCG+G+A+T | 156 |
| LNA14.45 | +C+A+A+AAGAATTC+G+G+A+T | 157 |
| LNA14.47 | +C+A+AAAGAATTC+G+G+A+T | 158 |

In certain embodiments, the oligonucleotide has the sequence LNA9, or a derivative thereof, as shown in Table 2, where a "+" before the letter denotes LNA nucleotides, or other chemically modified nucleotides (e.g., as described herein), and other letters denote DNA nucleotides (i.e., deoxyribonucleotide units):

TABLE 2

LNA9 derivatives

| NAME | SEQUENCE | SEQ ID NO: |
|---|---|---|
| LNA9.1 | +A+G+C+ATACTTACT+G+A+C+A | 159 |
| LNA9.2a | +C+A+TACTTACTG+A+C+A | 160 |
| LNA9.3 | +C+A+T+ACTTACTG+A+C+A+G | 161 |

TABLE 2-continued

LNA9 derivatives

| NAME | SEQUENCE | SEQ ID NO: |
|---|---|---|
| LNA9.5 | +A+T+ACTTACTGA+C+A+G | 162 |
| LNA9.6 | +A+T+A+CTTACTG+A+C+A+G | 163 |
| LNA9.8 | +A+T+ACTTACTG+A+C+A+G | 164 |
| LNA9.9 | +C+A+T+ACTTACTGA+C+A+G+C | 165 |
| LNA9.11 | +C+A+TACTTACTGA+C+A+G+C | 166 |
| LNA9.12 | +C+A+T+ACTTACTGAC+A+G+C | 167 |
| LNA9.13 | +A+T+ACTTACTGAC+A+G+C | 168 |
| LNA9.14 | +A+T+A+CTTACTGA+C+A+G+C | 169 |
| LNA9.15 | +A+T+A+CTTACTGAC+A+G+C | 170 |
| LNA9.16 | +A+T+ACTTACTGA+C+A+G+C | 171 |
| LNA9.18 | +T+A+CTTACTGAC+A+G+C | 172 |
| LNA9.19 | +T+A+CTTACTGA+C+A+G+C | 173 |
| LNA9.20 | +T+A+C+TTACTGA+C+A+G+C | 174 |
| LNA9.22 | +A+T+ACTTACTGACA+G+C+C | 175 |
| LNA9.23 | +A+T+ACTTACTGAC+A+G+C+C | 176 |
| LNA9 | +T+A+C+TTACTGACA+G+C+C | 75 |
| LNA9.25 | +T+A+C+TTACTGAC+A+G+C+C | 177 |
| LNA9.26 | +T+A+CTTACTGACA+G+C+C | 178 |
| LNA9.28 | +T+A+C+TTACTGACA+G+C+C+A | 179 |
| LNA9.29 | +T+A+CTTACTGACA+G+C+C+A | 180 |
| LNA9.30 | +T+A+C+TTACTGACAG+C+C+A | 181 |
| LNA9.31 | +T+A+CTTACTGACAG+C+C+A | 182 |
| LNA9.32 | +A+C+TTACTGACA+G+C+C+A | 183 |
| LNA9.33 | +A+C+TTACTGACAG+C+C+A | 184 |
| LNA9.35 | +A+C+T+TACTGACA+G+C+C+A | 185 |
| LNA9.41 | +C+T+T+ACTGACAG+C+C+A+G | 186 |
| LNA9.45 | +T+T+ACTGACAGCC+A+G+A | 187 |

In certain embodiments, the oligonucleotide has the sequence LNA8a, or a derivative thereof, as shown in Table 3, where a "+" before the letter denotes LNA nucleotides, or other chemically modified nucleotides (e.g., as described herein), and other letters denote DNA nucleotides (i.e., deoxyribonucleotide units):

TABLE 3

LNA8a derivatives

| NAME | SEQUENCE | SEQ ID NO: |
|---|---|---|
| LNA8a | +A+G+ACAGCGACCAA+A+A+G | 188 |
| LNA8a_1 | +A+G+A+CAGCGACCA+A+A+A+G | 189 |

TABLE 3-continued

LNA8a derivatives

| NAME | SEQUENCE | SEQ ID NO: |
|---|---|---|
| LNA8a_2 | +A+C+A+GCGACCA+A+A+A+G | 190 |
| LNA8a_3 | +A+C+AGCGACCAA+A+A+G | 191 |

In certain embodiments, the oligonucleotide has one of the following sequences where capitalized letters denote LNA nucleotides and lowercase letters denote DNA nucleotides (i.e., deoxyribonucleotide units):

a) LNA14:
(SEQ ID NO: 81)
5' CGACcaaaagaATTC 3';

b) LNA14.5:
(SEQ ID NO: 135)
5' CGACcaaaagaATT 3';

c) LNA14.8:
(SEQ ID NO: 137)
5' CGACcaaaagaaTTC 3';

d) LNA14.28:
(SEQ ID NO: 148)
5' GACcaaaagaatTCGG 3';

e) LNA14.30:
(SEQ ID NO: 149)
5' GACCaaaagaattCGG 3';

f) LNA 9:
(SEQ ID NO: 75)
5' TACTtactgacaGCC 3';

g) LNA9.1:
(SEQ ID NO: 159)
5' AGCAtacttactGACA 3';

h) LNA9.2a:
(SEQ ID NO: 160)
5' CATacttactgACA 3';

i) LNA9.8:
(SEQ ID NO: 164)
5' ATActtactgACAG;

j) LNA9.12:
(SEQ ID NO: 167)
5' CATActtactgacAGC;

k) LNA8a:
(SEQ ID NO: 188)
5' AGAcagcgaccaaAAG;

l) LNA8a.1:
(SEQ ID NO: 189)
5' AGACagcgaccaAAAG;
and m) LNA8a.2:
(SEQ ID NO: 190)
5' ACAGcgaccaAAAG.

In certain embodiments, the oligonucleotide has a sequence selected from (a)-(e). In certain cases, the oligonucleotide has a sequence selected from (f)-(j). In certain other cases, the oligonucleotide has a sequence selected from (k)-(m).

It will be understood that for any of the sequences (a)-(m), or a sequence selected from any one of Tables 1-3, one or more of the LNA nucleotides can be replaced with a modified nucleotide selected from BNA nucleotides, ENA nucleotides. cEt nucleotides, and 2'-modified nucleotides. In certain cases, 1, 2, 3, 4, or more of the LNA nucleotides can be replaced with a BNA nucleotide. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

It will also be understood that for any of the oligonucleotide sequences described above, one or more of the DNA nucleotides can be modified to provide a corresponding BNA, LNA, ENA, cEt, or 2'-modified nucleotide. In certain cases, 1, 2, 3, 4, or more of the DNA nucleotides can be replaced with a BNA nucleotide. In certain cases, 1, 2, 3, 4, or more of the DNA nucleotides can be modified to provide the corresponding LNA nucleotides. In certain cases, 1, 2, 3, 4, or more of the DNA nucleotides can be modified to provide the corresponding ENA nucleotides. In certain cases, 1, 2, 3, 4, or more of the DNA nucleotides can be modified to provide the corresponding cEt nucleotides. In certain cases, 1, 2, 3, 4, or more of the DNA nucleotides can be modified to provide a corresponding 2'-modified nucleotides (e.g., as described herein).

Sequence mutants of the oligonucleotide sequences described above are also encompassed by the present disclosure. It is understood that in any of the sequences described herein that 1, 2, 3, 4 or more of the nucleotide may be mutated to provide for a desirable property, such as enhanced inhibition activity, conjugation to a modifying agent, etc.

In some cases, any one of the sequences described herein (e.g., one of SEQ ID NO: 45-191) is comprised in a longer sequence, e.g., includes additional 5' and/or 3' nucleotides. In certain instances, the subject oligonucleotide is 75 nucleotides or less in length, such as 50 or less, 40 or less, or 35 nucleotides or less in length. In certain instances, the subject oligonucleotide is 30 nucleotides or less in length, such as 25 or less, 20 or less, 19 or less, 18 or less, 17 or less, 16 or less, 15 or less, 14 or less, 13 or less, 12 or less, 11 or less, or 10 nucleotides or less in length.

In some cases, the subject oligonucleotide compound comprises a sequence having a deletion relative to one of the sequences described herein (e.g., one of SEQ ID NO: 45-191). For example, a sequence where 1, 2 or 3 nucleotides are deleted from the 5' and/or 3' terminal of the sequence, e.g., one of SEQ ID NOs: 45-96. In some cases, the deletion sequence has one nucleotide missing from the 5' terminal of one of SEQ ID NOs: 45-191. In some cases, the deletion sequence has one nucleotide missing from the 3' terminal of one of SEQ ID NOs: 45-191. In some cases, the deletion sequence has two nucleotides missing from the 5' terminal of one of SEQ ID NOs: 45-191. In some cases, the deletion sequence has two nucleotides missing from the 3' terminal of one of SEQ ID NOs: 45-191.

In certain instances, the oligonucleotide comprises a sequence with at least 70% homology to any one of sequences (SEQ ID NO: 45)-(SEQ ID NO: 191) (e.g., as defined herein). In certain instances, the oligonucleotide comprises a sequence with 70% or more homology to any one of sequences (SEQ ID NO: 45)-(SEQ ID NO: 191), such as 75% or more, 80% or more, 85% or more, 90% or more or even more. In certain cases, the oligonucleotide comprises a sequence with from 70 to 80% homology to any one of the sequences (SEQ ID NO: 45)-(SEQ ID NO: 191). In certain cases, the oligonucleotide comprises a sequence with from 80% to 90% homology to any one of sequences (SEQ ID NO: 45)-(SEQ ID NO: 191). In certain cases, the oligonucleotide comprises a sequence with from 90% to 99% homology to any one of sequences (SEQ ID NO: 45)-(SEQ ID NO: 191).

In certain cases, the oligonucleotide sequence can include a mutation designed to cover single-nucleotide polymorphisms (SNPs) in a target PSL2 sequence. In some cases, the oligonucleotide is a modified version of LNA9 with single mutation sites that protect against PLS2 target sequences containing a nucleotide change with the LNA9 target sequence. It is understood that SNP mutations of interest can be applied to any of the sequences described herein. Mutated sequences of interest include, but are not limited to the following:

```
                                        (SEQ ID NO: 91)
        5' TACTTACTGACAGTC 3';

(SEQ ID NO: 92)
        5' TACTTACCGACAGCC 3';
        and (SEQ ID NO: 93)
        5' GGATTTCGGATGGCCA 3'.
```

In certain embodiments, the oligonucleotide has one of the following sequences where capitalized letters denote LNA nucleotides and lowercase letters denote DNA nucleotides:

```
        LNA9.G74C:
                                        (SEQ ID NO: 94)
        5' TACTtactgacaGTC 3';

LNA9.T80C:
                                        (SEQ ID NO: 95)
        5' TACTtaccgacaGCC 3';
        and LNA19.U56C:
                                        (SEQ ID NO:96)
        5' GGATttcggatggCCA 3'.
```

It will be understood that for any of the sequences (SEQ ID NO:94)-(SEQ ID NO:96), or one or more of the LNA nucleotides can be replaced with a modified nucleotide selected from ENA nucleotides, cEt nucleotides, and 2'-modified nucleotides. In certain cases, 1, 2, 3, 4, or more of the LNA nucleotides can be replaced with an ENA nucleotide. In certain cases, 1, 2, 3, 4, or more of the LNA nucleotides can be replaced with a cEt nucleotide. In certain cases, 1, 2, 3, 4, or more of the LNA nucleotides can be replaced with a 2'-modified nucleotide (e.g., substituted with MOE and other substituents as described herein).

In certain instances, the oligonucleotide has a maximum length that corresponds to the particular region of the PSL2 structure (e.g., a sub-region corresponding to nucleotides 34-87). In certain instances, the oligonucleotide length is 20 nucleotides or less, such as 15 nucleotides or less, 14 nucleotides or less, 13 nucleotides or less, 12 nucleotides or less, 11 nucleotides or less, 10 nucleotides or less, 9 nucleotides or less, 8 nucleotides or less, 7 nucleotides or less, or even less.

Oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate, 3'-NH-5'-O-phosphoroamidate, and thiophosphoramidates. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. In certain cases, the 2'-OH of the ribose sugar may be altered, e.g., as described herein. The 2'-OH of the ribose sugar may be altered to form 2'-O-methyl or 2'-O-allyl sugars, which provides resistance to degradation without comprising affinity. In certain cases, modification of the 2'-OH of the ribose sugar can improve toxicity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The oligonucleotide agents may be derivatized with any convenient modifying agent, e.g., by conjugation of the modifying agent to the 5'- and/or 3'terminal of the oligonucleotide sequence. In some cases, the modifying agent is a moiety that enhances cellular uptake (e.g., a lipid). Any convenient lipids may be conjugated to the subject oligonucleotides. In some instances, the modifying agent is a fatty acid, connected to the 5' or 3' terminal via an optional linker. The lipid group can be an aliphatic hydrocarbon or fatty acid, including but not limited to, derivatives of hydrocarbons and fatty acids, with examples being saturated straight chain compounds having 14-20 carbons, such as myristic (tetradecanoic) acid, palmitic (hexadecanoic) acid, and stearic (octadeacanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group includes derivatives such as amine, amide, ester and carbamate derivatives.

In some cases, the modifying agent is a further nucleic acid sequence having a desirable activity (e.g., recruitment of an RNase, as described herein). In certain instances, the modifying agent has a specific binding activity that provides for delivery of the oligonucleotide to a particular target, such as a cell-specific protein. In some cases, the modifying agent is an antibody of interest that specifically binds a cell-specific target of interest. In certain instances, the antibody modifying agent is specifically binds a hemagglutinin (HA) target.

The oligonucleotide active agent can be utilized in any convenient form. In some instances, the oligonucleotide active agent is single stranded. In some instances, the oligonucleotide active agent is double stranded. In some instances, the oligonucleotide active agent is an siRNA. In some instances, the oligonucleotide active agent is an shRNA. In some instances, the oligonucleotide active agent is a ssRNA. In some instances, one or more nucleotides of the ssRNA can be replaced with LNA nucleotides. In some instances, the oligonucleotide active agent is a ssDNA. In some instances, one or more nucleotides of the ssDNA can be replaced with LNA nucleotides.

Methods of Treatment

Aspects of the present disclosure include methods of treating or preventing influenza A virus infection in a subject. The subject oligonucleotide compounds find use as a new class of antiviral therapeutics that can efficiently disrupt packaging and completely prevent otherwise lethal disease in vivo. As demonstrated in the examples section, in vivo, intranasal dosing of exemplary oligonucleotide compounds resulted in potent antiviral efficacy and prevented lethal IAV infection in mice.

Aspects of the method include administering to a subject in need thereof a therapeutically effective amount of a subject compound to treat the subject for an infection or prevent infection in the subject. By "a therapeutically effective amount" is meant the concentration of a compound that is sufficient to elicit the desired biological effect (e.g., treatment or prevent of the condition or disease, influenza A virus infection). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease (e.g., infection); and/or (iii) relief, that is, causing the regression of clinical symptoms. In the context of influenza A virus infection, the term "treating" includes any or all of: reducing the number of viral cells in patient samples, inhibiting replication of viral cells, and ameliorating one or more symptoms associated with an infection.

The subject to be treated can be one that is in need of therapy, where the host to be treated is one amenable to treatment using the subject compound. In some embodiments, the subject is one that is suspected of having an influenza A virus infection. In certain embodiments, the subject is diagnosed as having an influenza A virus infection. As such, in some cases, the subject is one who has been infected with the virus.

In certain cases, the subject is one who is at risk of being infected, or is suspected of being infected with the virus. In some embodiments, the vRNA is a PB2 vRNA. The subject methods can be used to prevent infection of the subject with an influenza A virus. By "prevention" is meant that the subject at risk of influenza A virus infection is not infected despite exposure to the virus under conditions that would normally lead to infection. In some cases, the administering of the subject active agent (e.g., oligonucleotide compound) protects the subject against infection for 1 week or more, such as 2 weeks or more, 3 weeks or more, 1 month or more, 2 months or more, 3 months or more, etc. Multiple doses of the subject compound can be administered according to the subject methods to provide for protection of the subject form infection for an extended period of time. The timing and dosage amounts can be readily determined using conventional methods.

In some cases, the subject methods of treatment include a step of determining or diagnosing whether the subject has an influenza A virus infection. The determining step can be performed using any convenient methods. In some cases, the determining step includes obtaining a biological sample from the subject and assaying the sample for the presence of viral cells. The sample can be a cellular sample. The determining step can include identification of viral cells including a particular mutation.

Accordingly, a variety of subjects may be amenable to treatment using the subject compounds and pharmaceutical compositions disclosed herein. As used herein, the terms "subject" and "host" are used interchangeably. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of the subject compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective dosage of the subject compound is an effective volume in a mass concentration that ranges from about 50 ng/ml to about 50 µg/ml (e.g., from about 50 ng/ml to about 40m/ml, from about 30 ng/ml to about 20 µg/ml, from about 50 ng/ml to about 10 µm/ml, from about 50 ng/ml to about 1 µm/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the subject compound can be administered twice daily (qid), daily (qd), every other day (qod), every third day, three times per week (tiw), or twice per week (biw) over a period of time. For example, a compound can be administered qid, qd, qod, tiw, or biw over a period of from one day to about 2 years or more. For example, a compound can be administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of viral cells. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of viral cells or components thereof that are associated with the disease or condition of interest (e.g., as described herein). The sample can be a cellular sample. The assessment step(s) of the subject method can be performed at one or more times before, during and/or after administration of the subject compounds, using any convenient methods. In certain cases, the assessment step includes identification and/or quantitation of viral cells. In certain instances, assessing the subject include diagnosing whether the subject has a viral infection or symptoms thereof.

Screening Methods

Aspects of the present disclosure also include screening assays configured to identify agents that find use in methods of the invention, e.g., as reviewed above. Aspects of the present disclosure include methods for screening a candidate agent for the ability to inhibit influenza A virus in a cell. In some instances, the method comprises: contacting a sample comprising viral RNA (vRNA) comprising a PSL2 motif with a candidate agent; and determining whether the candidate agent specifically binds to the PSL2 motif. In some cases, an agent that specifically binds to the PSL2 motif will treat the subject having the influenza A virus infection. By assessing or determining is meant at least predicting that a given test compound will have a desirable activity, such that further testing of the compound in additional assays, such as animal model and/or clinical assays, is desired.

The candidate agent is selected from: a small molecule, an oligonucleotide, an antibody and a polypeptide. In some instances, the determining step comprises detecting a cellular parameter, wherein a change in the parameter in the cell as compared to in a cell not contacted with candidate agent indicates that the candidate agent specifically binds the PSL2 motif. In some cases, the subject screening method is a method of RNA structure mapping, such as SHAPE analysis (Selective 2'-hydroxyl acylation analyzed by primer extension). In certain instances, the candidate agent is an oligonucleotide.

Drug screening may be performed using an in vitro model, a genetically altered cell or animal, or purified PSL2 protein. One can identify ligands that compete with, modulate or mimic the action of a lead agent. Drug screening identifies agents that bind to particular sites of PSL2 motif. A wide variety of assays may be used for this purpose, including labeled in vitro binding assays, electrophoretic mobility shift assays, immunoassays for protein binding, and the like. Knowledge of the 3-dimensional structure of PSL2, derived from the structural studies described herein, can also lead to the rational design of small drugs that specifically inhibit IAV activity.

The term "agent" as used herein describes any molecule, e.g., oligonucleotide, protein or pharmaceutical, with the capability of binding PSL2 to inhibit IAV. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, such as oligonucleotides, antibodies, polypeptides, and organic molecules, e.g., small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Of interest in certain embodiments are compounds that pass the blood-brain barrier.

Where the screening assay is a binding assay, one or more of the molecules may be joined to a member of a signal producing system, e.g., a label, where the label can directly or indirectly provide a detectable signal. Various labels include, but are not limited to: radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

Cells and viruses: HEK 293T and MDCK cells were obtained from American Type Culture Collection (Manasass, Va.) and were maintained in Dulbecco's modified Eagle's medium with 10% fetal bovine serum and penicillin-streptomycin (Gibco). Influenza A/PR/8/34 (PR8) H1N1 virus was generated using an eight-plasmid reverse genetic system. Tissue-cultured adapted influenza A/Hong Kong/8/68 (HK68) H3N2 virus was obtained from ATCC (ATCC-VR-1679). Viruses were grown and amplified in 10-day-old specific-pathogen-free chicken embryos at 35° C. (Charles River Laboratories; SPAEAS).

Plasmid constructs and cloning: Plasmids were used containing the wild-type PB2 segments from influenza viruses A/PuertoRico/8/34 (H1N1) [PR8], A/New York/470/2004 (H3N2) [NY470], A/New York/312/2001 (H1N1) [NY312], A/Brevig Mission/1/1918 (H1N1) [1918], A/California/04/2009 (H1N1) [CA09], A/Vietnam/03/2004 (H5N1) [VN1203], and A/Anhui/1/2013 (H7N9). For the generation of PR8 packaging mutant vRNA, we utilized a Stratagene QuickChange XL site-directed mutagenesis kit (Stratagene) for mutagenesis of a pDZ plasmid containing the PB2 gene of PR8. Sequences of each mutated construct were confirmed by automated sequencing.

Reverse genetics and virus titrations: Influenza A/Puerto Rico/8/34 (PR8) virus was generated using an eight-plasmid reverse genetic system (Hoffman et al., 2000). Briefly, to produce recombinant PR8 viruses, $10^6$ cells of a 293T/MDCK co-culture were Lipofectamine 3000 (Invitrogen) transfected with 1 ug of one of each of the eight segments contained within plasmids that utilize a bidirectional dual Pol I/II promoter system for the simultaneous synthesis of genomic vRNA and mRNA. Cells were collected 24 hours post-transfection and inoculated into the allantoic cavities of 10-day-old chicken embryos (Charles River, research grade specific-pathogen-free eggs). Rescue of recombinant viruses was assessed by hemagglutination activity. Each newly rescued virus was further plaque titered and mutations were confirmed by sequencing of mutated genes. Plaque assays were carried out on confluent MDCK cells as described previously (Szretter et al., 2006). Hemagglutination (HA) assays were carried out in 96-well round-bottomed plates at room-temperature, using 50 ul of virus dilution and 50 ul of a 0.5% suspensions of turkey red blood cells in phosphate-buffered saline (PBS).

Viral growth kinetics: Growth kinetics for PR8 viruses was determined by inoculation of 10-day-old chicken eggs with 100 plaque-forming units (PFU) of virus. At 72 h post-inoculation, the virus titer in the allantoic fluid was determined by titration of plaques on MDCK cells.

Isolation of packaged vRNAs: To analyze packaged vRNA for PR8 mutated viruses, 10-day-old eggs were inoculated with approximately 1000 PFU of recombinant virus and incubated for 72 h. Allantoic fluid was harvested, and supernatant was clarified by low-speed centrifugation. Clarified supernatant was then layered on a 30% sucrose cushion and ultra-centrifuged at 30,000 RPM for 2.5 h (Beckman Rotor SW41). Pelleted virus was resuspended in PBS and TRIzol (Invitrogen) extracted. Precipitated vRNA was resuspended in a final volume of 20 ul of 10 mM Tris-HCl (pH 8.0) and stored at −80° C.

qPCR analysis of packaged vRNAs: Approximately 200 ng of extracted vRNAs were reverse transcribed using a universal 3' primer (5'-AGGGCTCTTCGGCCAGCRAAAGCAGG) (SEQ ID NO:97) and Superscript III reverse transcriptase (RT) (Invitrogen). The RT product was diluted 10,000-fold and used as a template for quantitative PCR (qPCR). Separate PCRs were then carried out as previously described (Marsh et al., 2007) with segment-specific primers. The 10 ul reaction mixture contained 1 ul of diluted RT product, a 0.5 uM primer concentration, and SYBR Select Master Mix (Applied Biosystems) that included SYBR GreenER dye, 200 uM deoxynucleoside triphosphates, heat-labile UDG, optimized SYBR Green Select Buffer, and AmpliTaq DNA polymerase UP enzyme. Relative vRNA concentrations were determined by analysis of cycle threshold values, total vRNA amount was normalized by equalization of the level of HA vRNA, and then percentages of incorporation were calculated relative to the levels of wt vRNA packaging. Viral packaging results represent the averaged levels of vRNA incorporation±standard deviations derived from two independent virus purifications, with vRNA levels quantified in triplicate, n=6.

Mouse infections: Groups of 6-8 week old female BALB/C mice (Jackson Laboratory) were lightly anesthetized with isoflurane and intranasally infected with 50 ul of 1000 PFU of wild type mouse-adapted PR8 (H1N1) virus (ATCC), PB2 mutated PR8 recombinant viruses, or sterile PBS. Weights were measured daily, and animals were humanely sacrificed by day 10 or when weight loss exceeded 20%. All animal care and experimental procedures are in accordance with the National Institutes of Health Guidelines for the Care and Use of Laboratory Animals and approved by the Stanford University Administrative Panel on Laboratory Animal Care.

Locked nucleic acid (LNA) design and preparation: Oligonucleotides containing locked nucleic acids (LNA) were custom synthesized from Exiqon. Capitalized letters denote LNA. Lowercase letters denote typical (non-locked) DNA nucleotides. All oligonucleotides contained phosphorothioate internucleoside linkages. The LNAs were designed to be complementary to different sequences contained in the PSL2 structure of segment PB2. LNA 8a and 9 are designed to contain a stretch of 6-8 DNA nucleotides for RNAse-H recruitment. Sequences of all LNAs are shown below.

LNA 1:
(SEQ ID NO: 67)
5' AccAaaAGaaT 3'

LNA 2:
(SEQ ID NO: 68)
5' TggCcATcaaT 3'

LNA 3:
(SEQ ID NO: 69)
5' TagCAtActtA 3'

LNA 4:
(SEQ ID NO: 70)
5' CCAAAAGA 3'

LNA 5:
(SEQ ID NO: 71)
5' CATACTTA 3'

LNA 6:
(SEQ ID NO: 72)
5' CagaCaCGaCCaaAA 3'

LNA 7:
(SEQ ID NO: 73)
5' TAcTtaCTgaCagCC 3'

LNA 8a:
(SEQ ID NO: 188)
5' AGAcagcgaccaaAAG 3'-with RNase-H activity

LNA 9:
(SEQ ID NO: 75)
5' TACTtactgacaGCC 3'-with RNase-H activity

LNA9.2:
(SEQ ID NO: 76)
5' TACttactgacAGCC 3'

LNA10:
(SEQ ID NO: 77)
5'ACCaaaagAAT 3'

LNA11:
(SEQ ID NO: 78)
5' TGGccatcAAT 3'

LNA12:
(SEQ ID NO: 79)
5'TAGcatacTTA 3'

LNA13:
(SEQ ID NO: 80)
5'CgacCAaaAGaattC 3'

LNA14:
(SEQ ID NO: 81)
5'CGACcaaaagaATTC 3'

LNA15:
(SEQ ID NO: 82)
5'GaTGgCcATcaAttA 3'

LNA16:
(SEQ ID NO: 83)
5'GATGgccatcaATTA 3'

LNA17:
(SEQ ID NO: 84)
5'TcTAgCaTActTacT 3V

-continued

LNA18:
5'TCTAgcatactTACT 3' (SEQ ID NO: 85)

LNA19:
5'GAAttcggatgGCCA 3' (SEQ ID NO: 86)

LNA20:
5'GGCCatcaattaGTG 3' (SEQ ID NO: 87)

LNA21:
5'TTCGgatggccaTCA 3' (SEQ ID NO: 88)

LNA22:
5'AGCCagacagCGA 3' (SEQ ID NO: 89)

LNA23:
5'GACAgccagacaGCA 3' (SEQ ID NO: 90)

The following oligonucleotides were designed to cover single-nucleotide polymorphisms (SNPs) in PSL2 sequence. The following exemplary sequences are modified versions of LNA9 with single mutation sites that would protect against a few avian and bat strains whose PLS2 sequence contains a nucleotide change with the LNA9 target sequence. It is understood that similar design can be applied to any of the sequences described herein.

LNA9.G74C:
5' TACTtactgacaGTC 3' (SEQ ID NO: 94)

LNA9.T80C:
5' TACTtaccgacaGCC 3' (SEQ ID NO: 95)

LNA19.U56C:
5' GGATttcggatggCCA 3' (SEQ ID NO: 96)

Antiviral assays: LNAs were reconstituted in RNAse free water at 100 µM, aliquoted and stored at −20° C. prior to single use. Lipofectamine 3000 (Life Technology) was used to transfect LNA into cells at a final concentrations of 1 µM, 100 nM, 10 nM, and 1 nM per manufacturer's protocol. For prophylactic antiviral assays, $10^6$ MDCK cells were plated in 6-well plates 24 h prior to being transfected with the indicated LNA. Cells were then infected at 4 h, 2 h, or 1 h post-transfection with 0.01 MOI of PR8 (H1N1) or HK68 (H3N2) virus. For post-infection, therapeutic antiviral assessment, MDCK cells were infected with PR8 or HK68 as described. LNAs were then transfected at 4 h, 2 h, or 1 h post-infection. After 48 h post-infection, supernatant was collected, and viral titer was determined by plaque assay. In vitro transcription of vRNA: For each wild-type isolate (PR8, 1918, VN1203, NY470, NY312, CA09, and A/Anhui/1/2013 H7N9) and PR8 packaging mutant clones, PB2 cDNA was amplified from plasmid using segment-specific primers under a T7 promoter. Amplified cDNA was gel-purified using an Invitrogen DNA gel kit. vRNAs were then produced by in vitro transcription, using T7-MEGAscript. vRNAs for SHAPE were purified by MEGAclear (Thermofisher, cat. no. AM1908) with purity and length verified by capillary electrophoresis.

sf-SHAPE analysis of vRNA: PB2 vRNA was folded (100 mM NaCl; 2.5 mM MgCl; 65° C. for 1 min, 5 min cooling at room temperature, 37° C. for 20-30 min) in 100 mM HEPES, pH=8. 2 min acylation with NMIA (Wilkinson et al., 2006) and reverse transcription (RT) primer extension were performed at 45° C. for 1 min, 52° C. for 25 min, 65° C. for 5 min, as previously described (Mortimer and Weeks, 2009). 6FAM was used for all labeled primers. Exceptions to these protocols were as follows: (i) RNA purification after acylation was performed using RNA C&C columns (Zymo Research), rather than ethanol precipitation; (ii) before and after SHAPE primer buffer was added, the mixture was placed at room temperature for 2-5 min, which enhanced RT transcription yields significantly; (iii) DNA purification was performed using Sephadex G-50 size exclusion resin in 96-well format then concentrated by vacuum centrifugation, resulting in a more significant removal of primer; and (iv) 2 pmol RNA was used in ddGTP RNA sequencing reactions.

The ABI 3100 Genetic Analyzer (50 cm capillaries filled with POP6 matrix) was set to the following parameters: voltage 15 kV, T=60° C., injection time=15 s. The GeneScan program was used to acquire the data for each sample, which consisted of purified DNA resuspended in 9.75 ul of Hi-Di formamide, to which 0.25 ul of ROX 500 internal size standard (ABI Cat. 602912) was added. PeakScanner parameters were set to the following parameters: smoothing=none; window size=25; size calling=local southern; baseline window=51; peak threshold=15. Fragments 250 and 340 were computationally excluded from the ROX500 standard (Akbari et al., 2008). The data from PeakScanner were then processed into SHAPE data by using FAST (fast analysis of SHAPE traces), a custom program (Pang et al., 2011). FAST automatically corrects for signal differences due to handling errors, adjusts for signal decay, and converts fragment length to nucleotide position, using a ddGTP ladder as an external sizing standard and the local Southern method (Pang et al., 2011 and Pang et al., 2012).

RNAstructure parameters: slope and intercept parameters of 2.6 and −0.8 kcal/mol, were initially tried, as suggested (Deigan et al., 2009); smaller intercepts closer to 0.0 kcal/mol (e.g. ~−0.3) were found to produce fewer less optimal structures (within a maximum energy difference of 10%). This minor parameter difference may be due to the precise fitting achieved between experimental and control data sets by the automated FAST algorithm. In its current implementation, FAST is integrated into RNAstructure, which requires MFC (Microsoft Foundation Classes). RNA structures were drawn and colored using RNAViz 2 (De Rijk et al., 2003) and finalized in Adobe Illustrator.

Construct design, RNA synthesis and chemical modification for mutate-and-map experiments: Double-stranded DNA templates were prepared by PCR assembly of DNA oligomers designed by an automated MATLAB script as previously described (NA_Thermo, available at "https:" followed by "//github." Followed by "com/DasLab/NA_thermo") (Kladwang and Cordero et al., 2011). Constructs for mutate-and-map ($M^2$) includes all single mutants to Watson-Crick counterpart. Compensatory mutants for mutation/rescue were designed based on base-pairing in the proposed secondary structure (Tian et al., 2014). In vitro transcription reactions, RNA purification and quantification steps were as described previously (Kladwang and Cordero et al., 2011). One-dimensional chemical mapping, mutate-and-map ($M^2$), and mutation/rescue were carried out in 96-well format as described previously (Kladwang and VanLang et al., 2011; Kladwang and Cordero et al., 2011; Cordero et al., 2013). Briefly, RNA was heated up and cooled to remove secondary structure heterogeneity; then folded properly and incubated with SHAPE reagent (5 mg/mL 1-methyl-7-nitroisatoic anhydride (1M7)) (Mortimer and Weeks, 2007); modification reaction was quenched and RNA are recovered by poly(dT) magnetic beads (Ambion) and FAM-labeled Tail2-A20 primer; RNA was washed by 70% ethanol (EtOH) twice and resuspended in ddH$_2$O; followed by reverse transcription to cDNA and heated NaOH treatment to remove RNA. Final cDNA library was recovered by magnetic bead separation, rinsed, eluted in Hi-Di formamide (Applied Biosystems) with ROX-350 ladder, loaded to capillary electrophoresis sequencer (ABI3100). Data processing, structural modeling, and data deposition: The HiTRACE software package version 2.0 was used to analyze CE data (both MATLAB toolbox and web server available (Yoon et al., 2011; Kim et al., 2013)). Trace alignment, baseline subtraction, sequence assignment, profile fitting, attenuation correction and normalization were accomplished as previously described (Kim et al., 2009; Kladwang et al., 2014). Sequence assignment was accomplished manually with verification from sequencing ladders. Data-driven secondary structure models were obtained using the Fold program of the RNAstructure package version 5.4 (Mathews et al., 2004) with pseudo-energy slope and intercept parameters of 2.6 kcal/mol and −0.8 kcal/mol. 2-dimensional Z score matrices for M$^2$ datasets, and helix-wise bootstrapping confidence values were calculated as described previously (Tian et al., 2014; Kladwang and VanLang et al., 2011). Z score matrices were used as base-pair-wise pseudofree energies with a slope and intercept of 1.0 kcal/mol and 0 kcal/mol. Secondary structure images were generated by VARNA (Darty et al., 2009). All chemical mapping datasets, including one-dimensional mapping, mutate-and-map, and mutation/rescue, have been deposited at the RNA Mapping Database ("http:" followed by "//rmdb.stanford." followed by "edu") (Cordero et al., 2012).

SHAPE analysis of LNA-targeted vRNA: DNA template of PR8 segment PB2 was prepared by PCR assembly of DNA oligomers, and in vitro transcription reactions, RNA purification and quantification steps were as described previously (Kladwang and VanLang et al., 2011). One-dimensional SHAPE chemical mapping was performed in 96-well plate format as described above with the following exception: once RNA was denatured and refolded as described, 100 nM of each prepared LNA was added to the folded RNA and incubated with 5 mg/mL of SHAPE reagent 1M7 (1-methyl-7-nitroisatoic anhydride). Modification quenching, RNA recovery, re-suspension, reverse transcription, cDNA sequencing and data processing was performed as described, see, Kladwang and VanLang et al., 2011.

Example 1

Figure 1C:
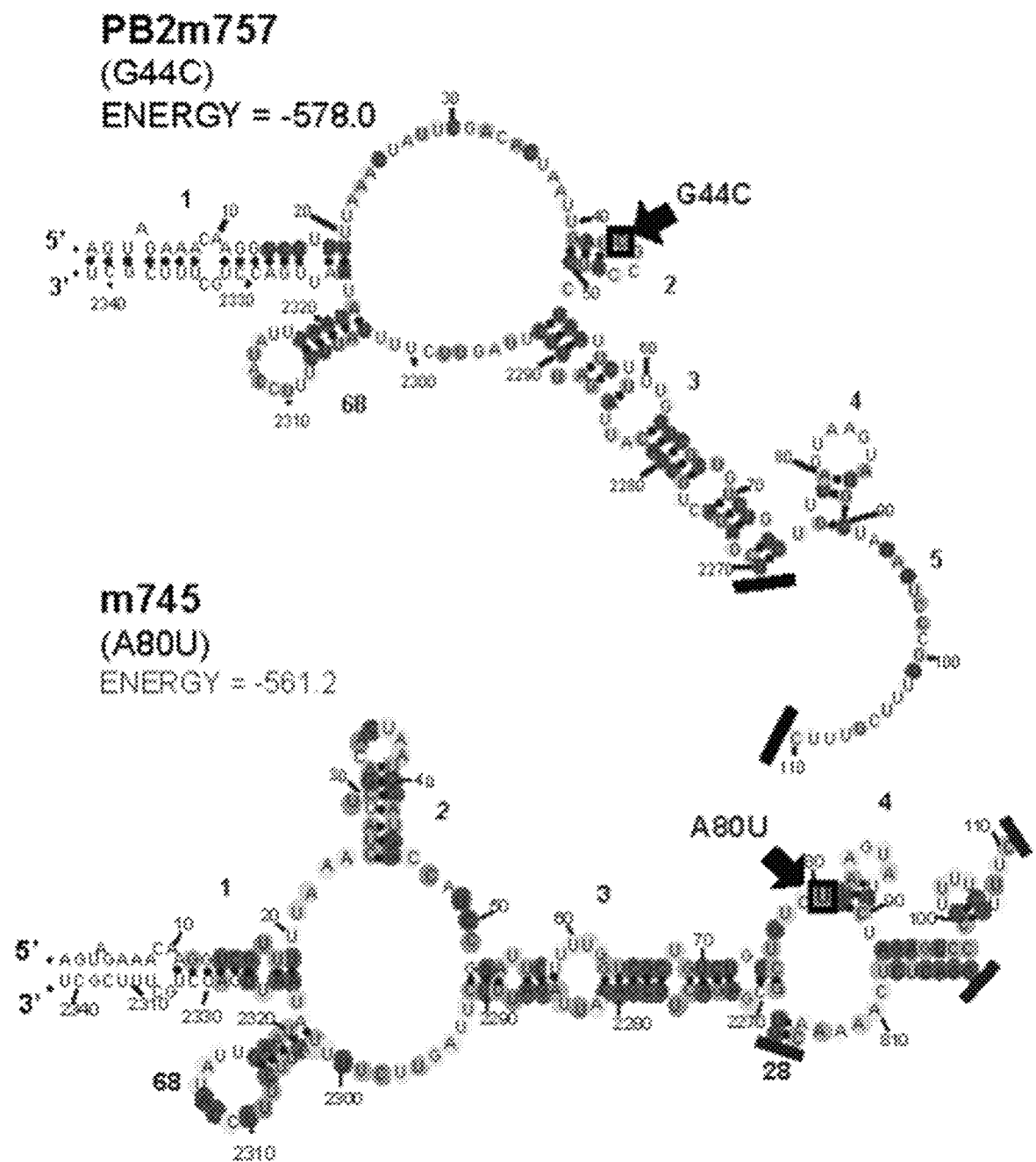

SHAPE-Characterization of IAV Segment PB2 Packaging Signal Identifies Conserved Structure Selective 2'-hydroxyl acylation analyzed by primer extension (SHAPE) and computational modeling was applied to IAV segment PB2 genomic vRNA to search for structured RNA domains. In vitro transcribed full-length (−)-sense PB2 vRNA from strain A/Puerto Rico/8/1934 (H1N1) "PR8" was folded in solution (Pang et al., 2011) and interrogated using an electrophilic SHAPE reagent that preferentially reacts with nucleotides existing in flexible, single-stranded states (Wilkinson et al., 2006) (FIG. 1). This analysis revealed that much of the 2341-nt vRNA is largely unstructured (FIG. 2), consistent with recent bioinformatics studies that found higher potential for RNA secondary structure conservation in the (+)-sense over the (−)-sense RNA for all segments, including PB2 (Priore et al., 2012; Moss et al., 2011). These previous studies did not analyze the terminal coding regions (TCR), and instead stopped 80 nucleotides short of the PB2 5' TCR's end. SHAPE-guided modeling suggested several areas in this region which contain stable RNA secondary structures, most notably a stem-loop motif, named herein as the Packaging Stem-Loop 2 (PSL2) (FIG. 1A), comprising nucleotides 34-87 ((−)-sense notation). This segment included a set of nucleotides that were previously implicated in PB2 packaging through mutational analysis via an unidentified mechanism (FIG. 1A-1B, see circled nucleotides) (Gao et al., 2012; Marsh et al., 2008; Liang et al., 2008; Gog et al., 2007). Supporting the hypothesis that these prior mutations act through disruption of PSL2 structure, SHAPE analysis of the mutants yielded different conformations that all abrogated the wild-type PSL2 structure (FIG. 1C. FIG. 3). The 60-nucleotide region encompassing PSL2 displays near 100% sequence conservation at the single nucleotide level between seasonal as well as pandemic strains of different subtypes and species origins (FIG. 4), suggesting the existence of a strict biologic requirement to maintain an intact PSL2 structure. Because differing downstream sequences within PB2 vRNA could alter the secondary structure of PSL2, PSL2's structural conservancy was explored by performing SHAPE analysis on full-length wild-type PB2 vRNAs isolated from a variety of IAV strains and subtypes, including the highly pathogenic avian H5N1 and pandemic 1918 H1N1 strains. Despite the presence of two diverging nucleotides within the stem-loop and significant divergence in flanking sequences, the PSL2 stem-loop structure was recovered in SHAPE-guided modeling of PB2 RNA across these diverse species and subtypes (FIG. 1D-1F).

FIG. 1A-FIG. 1F shows SHAPE-chemical mapping performed on full-length (−)-sense wild-type PB2 vRNAs. Colors denote SHAPE reactivity, which is proportional to the probability that a nucleotide is single-stranded. All structures are truncated to highlight the 5' termini sequence structure. Energy=ΔG free energy value of determined structures generated by the RNA structure modeling algorithm using SHAPE pseudofree energy parameters. (FIG. 1A) Wild-type PB2 RNA secondary structure from strain A/Puerto Rico/8/1934 "PR8" (H1N1). Color-coded circles correspond to nucleotides sites where synonymous mutations were reported to affect PB2 packaging (Gao et al., 2012; Marsh et al., 2011). (FIG. 1B) Packaging efficiency of synonymous mutants in (FIG. 1a), determined by qPCR. Results performed in triplicate. Error bars=±SD. Box below indicates mutant name and corresponding mutational change. Nucleotide numbering shown in the genomic (−)-sense orientation. (FIG. 1C) SHAPE-determined structures of PB2 packaging-defective mutant vRNAs, m757 (G44C) and m745 (A80U). Black boxes=site(s) of synonymous mutation, (FIG. 1D-FIG. 1F) SHAPE-determined structures of wild-type PB2 from pandemic and highly pathogenic strains, including different subtypes: (FIG. 1D) 1918 pandemic (A/Brevig Mission/1/1918 (H1N1)), (FIG. 1E) Highly-pathogenic avian (A/Vietnam/1203/2004 (H5N1)), (FIG. 1F) 2009 pandemic 'swine' (A/California/04/2009 (H1N1)).

FIG. 2, panels A-B, shows SHAPE reactivity of full-length PB2 vRNA. (FIG. 2, panel A) Average SHAPE reactivity (window bin size=100 nt) as a function of nucleotide position for the full-length (−)-sense PB2 vRNA from IAV strain A/Puerto Rico/8/1934 (H1N1). The PSL2 region (highlighted in blue, nts 34-86) encompassess the 5' packaging signal domain, which possesses a high density of codons whose third position is conserved, and has one of the lowest SHAPE reactivities within the vRNA. The region after PSL2 is relatively unstructured yet contains another potential site for the presence of RNA structure between nucleotides 1400 and 1500. Interestingly, this second internal region was also predicted to contain structural elements by a 2011 bioinformatics study (ref. 19). (FIG. 2, panel B) Zoomed in view of PSL2 region from (FIG. 2a). Window bin size=10 nt.

FIG. 3A-FIG. 3E shows packaging-defective mutations disrupt wild-type SHAPE reactivity. Left: Mutant SHAPE reactivity plotted as change over WT. Nucleotide numbering starts from 5' end of (−)-sense vRNA. Orange bars indicate site of mutation. Energy values represent ΔG free energy of the predicted structure generated by the RNAstructure modeling algorithm using SHAPE pseudofree energy parameters. Right: SHAPE-determined structures of full-length (−)-sense mutant PB2 vRNA from PR8 strain (H1N1). Images are truncated to highlight 5' terminal region. (FIG. 3A) Wild-type. Packaging-defective mutants: (FIG. 3B) m744b (AG83, 85UA). (FIG. 3C) m745 (A80U). (FIG. 3D) m55c (CU35, 36UC). (FIG. 3E) m757 (G44C).

FIG. 4 shows conservancy of nucleotide sequence containing the PSL2 structure. Graphical representation of nucleic acid sequence alignments across diverse influenza A viral subtypes and strains ("weblogo." followed by "berkeley" followed by ".edu"). The overall height represents sequence conservation at that nucleotide position, while the height of symbols within each position indicates the relative frequency of each nucleotide at that site. Black box=PSL2 region. Sequences included in the alignment: highly pathogenic A/Brevig Mission/1/1918 (H1N1), pandemic "swine flu" A/California/04/2009 (H1N1), modern human A/New York/470/2004 (H3N2), human A/Puerto Rico/8/1934 (H1N1), high pathogenic avian A/Vietnam/03/2004 (H5N1), human A/Hong Kong/8/1968 (H3N2), and human A/New York/312/2001 (H1N1). RNA nucleotides numbered in (−)-sense orientation. Sequence alignment of the terminal 5' region of PB2 corresponding to the above sequences. Shaded blue box encompasses the PSL2 RNA secondary structural element. Black dots designate divergent nucleotide sites.

Figure 5A:
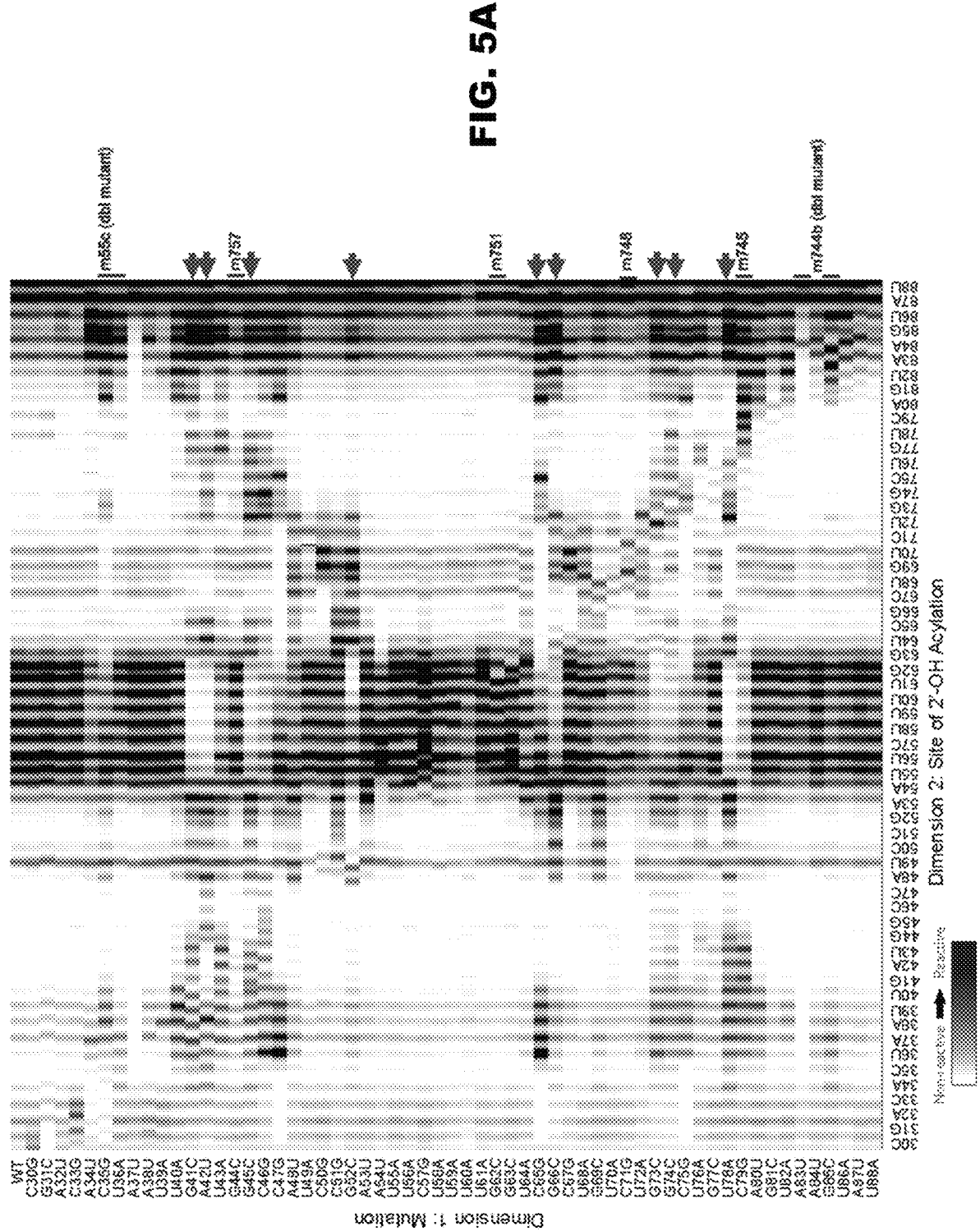
Figure 5B:
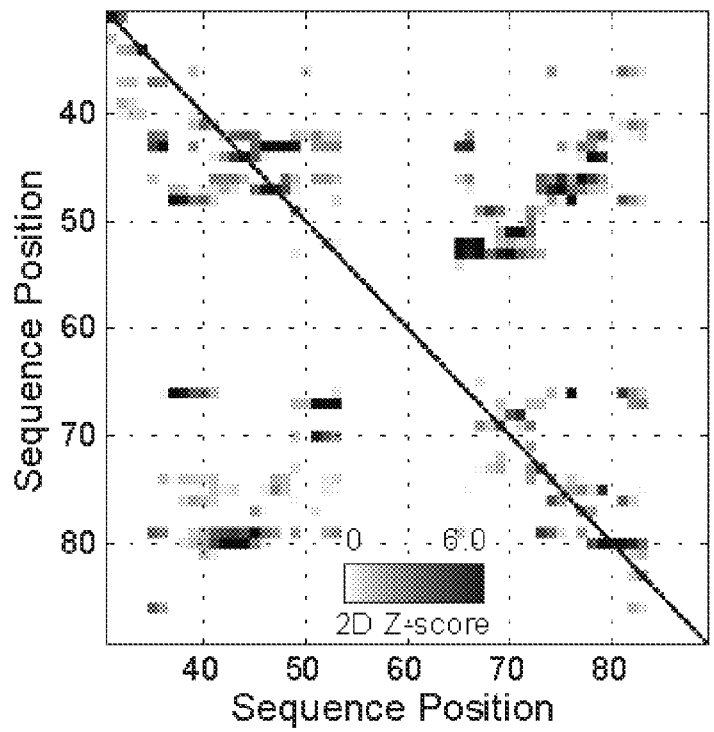
Figure 5C:
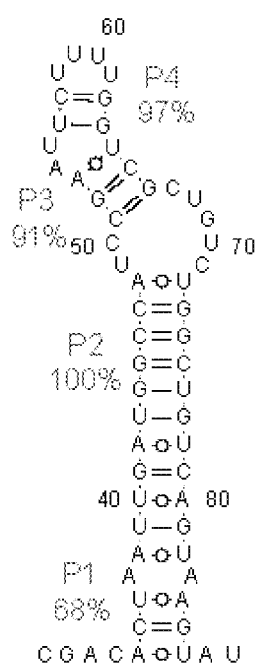
Figure 5D:
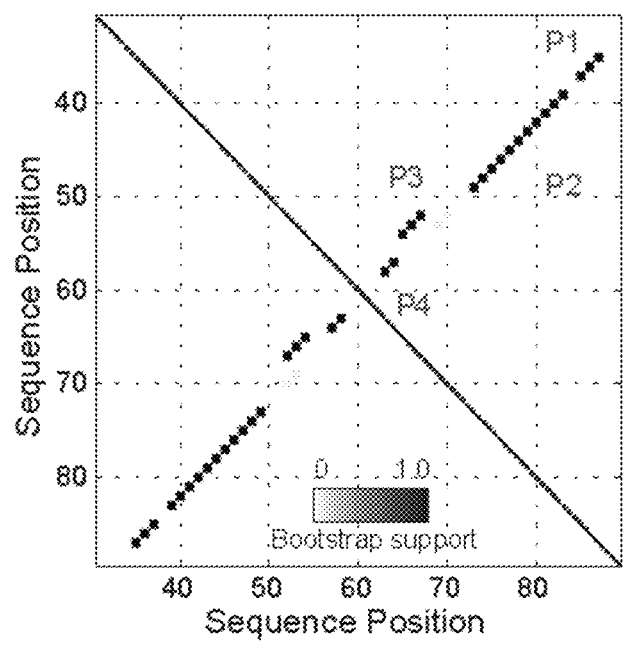

Mutate-and-Map Strategy Validates PSL2 Structure and Predicts Novel Packaging Mutants To further test the SHAPE analysis of the PSL2 RNA structure and to uncover additional informative mutations needed for in vivo tests, multidimensional chemical mapping (Kladwang and Das, 2010) methods were applied to the PSL2 segment. First, mutate-and-map ($M^2$) measurements confirmed disruption of the chemical reactivity pattern upon systematic mutation of each stem residue, including changes at nucleotides previously found to be critical for PB2 packaging (FIG. 5A, see noted fields) (Marsh et al., 2008; Gog et al., 2007). Automated computational analysis based on these $M^2$ data recovered the SHAPE-guided PSL2 structure with high confidence (FIG. 1C, FIG. 3, FIG. 5B-FIG. 5D), further validating the structural model. Second, as predictive tests, compensatory mutations were designed to restore the base pairs in the wild-type stem-loop structure that were disrupted by the initial packaging-defective mutations (FIG. 6, panels A-B). These mutation-rescue variants indeed restored the PSL2 SHAPE pattern, providing base-pair resolution in vitro validation of the modeled structure and suggesting sequence variants to test the role of PSL2 structure in vivo.

FIG. 5A-FIG. 5D shows 2-Dimensional Mutate-and-Map (M2) analysis of PSL2 RNA secondary structure. (FIG. 5A) Systematic single nucleotide mutation and mapping of resulting chemical accessibility reveals interactions in the three-dimensional structure of the RNA. Chemical accessibilities, plotted in grey scale (black=highest SHAPE reactivity), across 88 single mutations at single-nucleotide resolutions of PSL2 element from PR8 strain PB2. Reactivity peaks (left to right) correspond to nucleotides from the 5' to 3' end of the PB2 RNA. Nucleotide sites corresponding to known packaging mutations (as reported by Marsh et al., 2008) are indicated on right in blue. Red arrows denote prominent packaging-defective mutant sites predicted by M2 analysis. (FIG. 5B) Strong features of mutate-and-map data isolated by Z-score analysis (number of standard deviations from mean at each residue). Z-scores were calculated for each nucleotide reactivity by subtracting the average reactivity of this nucleotide across all mutants and dividing by standard deviation (output_Zscore_from_rdat in HiTRACE). Squares show secondary structure model guided by mutate-and-map data. Dark signals highlight evidence of structured nucleotide pairing. (FIG. 5C) RNA secondary structure for 5' packaging signal region (nts 30-93) derived from incorporating Z-scores into the RNA-structure modelling algorithm: bootstrap confidence estimates given as green percentage values. Bootstrap values provide numerically accurate indicators of structural confidence. Low bootstrap confidence values suggest existence of alternative structural models. (FIG. 5D) Bootstrap support values for each base-pair shown as grayscale shading.

FIG. 6 shows Design of compensatory mutations to previously described PR8 PB2 mutants. (FIG. 6, panel A) Previously described synonymous mutants (m757, m745, m55c) are mapped onto PSL2 structure. (FIG. 6, panel B) Compensatory mutations (m55c-comp, m745-comp, and m757-comp) were designed at sites predicted to restore wild-type PSL2 structure based on SHAPE and mutate-and-map chemical analyses. Black boxed nucleotides denote site of compensatory mutation. (−)-sense vRNA orientation is shown. For mutations where a non-synonymous change was required to restore the structure, the alteration in encoded protein sequence is indicated.

To test whether the PSL2 stem-loop structure observed in solution was relevant to virus packaging in the cellular milieu, the same nine synonymous mutations reported by Gog et al., 2007 and Marsh et al., 2008 (FIG. 1A-FIG. 1B, FIG. 7 panel A) as well as four new synonymous mutations characterized by $M^2$ analysis (FIG. 7, panel B) were cloned into pDZ plasmids containing the PR8 PB2 gene (Marsh et al., 2008; Liang et al., 2008; Gog et al., 2007) (FIG. 8). The packaging efficiencies of the 9 previously known mutants now in the PR8 background were comparable to those originally described in the WSN33 virus[15] (FIG. 7, panel C). Of these, mutants m55c, m757, m745, and m744b, were predicted to show the most significant impairment based on their location within PSL2's stem regions (FIG. 1C, FIG. 3A-FIG. 3F, FIG. 7). In contrast, published mutations that have no effect on PB2 packaging (e.g. m731) mapped to the unstructured apical loop or fell outside of PSL2 and did not alter its structural integrity (FIG. 9A) (Marsh et al., 2008). The three novel synonymous mutants (m74-1, m74-2, and m68) identified by $M^2$-analysis as having a significant effect on in vitro PSL2 structure (FIG. 5A) showed significant loss in PB2 packaging, whereas mutation sites that resulted in negligible change in SHAPE reactivity compared to the wild-type PSL2 structure, gave wild-type-like packaging efficiency levels (e.g., m56) (FIG. 7, panel D).

FIG. 7 shows synonymous mutation of single highly conserved codons of the PR8 PB2 vRNA. (FIG. 7, panel A)

Previously published synonymous mutations implicated in PB2 packaging. Upper line is the parental PR8 vRNA sequence ((+)-sense orientation), and the mutated single nucleotides are bolded in red on the line below. Numbering and nomenclature of introduced mutations are based on the reports by Marsh et al., 2008 and Gog et al., 2007. Yellow highlighted region indicates sequence containing PSL2 structure. (FIG. 7, panel B) Design of primer sequences for cloning of synonymous mutations identified from M2-analysis (see Supplemental FIG. 4a) into pDZ plasmids. Sequences are in (+)-sense orientation. Highlighted nucleotides=mutation site. (FIG. 7, panels C-D) Packaging efficiencies representing the percentage of mutant PB2 packaging relative to parental wild-type PB2 for (FIG. 7, panel C) Previously published synonymous mutants, and (FIG. 7, panel D) M2-analysis identified synonymous mutants. Results from two independent experiments, assays performed in triplicate (n=6). Error bars represent±SD.

FIG. 8 shows PB2 Packaging mutant nomenclature and corresponding sites of mutation. Mutation nomenclature chart indicating names and site(s) of mutation from: 1) Previously published synonymous mutations implicated in PB2 packaging (shown in blue), based on the reports by Marsh et al., 2008 and Gog et al., 2007; and 2) PSL2 structure designed single mutants (shown in black) and double-compensatory mutants (shown in red). Numbering and nomenclature of introduced mutations are based on the genomic, (−)-sense vRNA. Instances where mutation results in change in protein coding are indicated by synonymous (SYN) or non-synonymous (Non-SYN) fields.

Figure 9C:
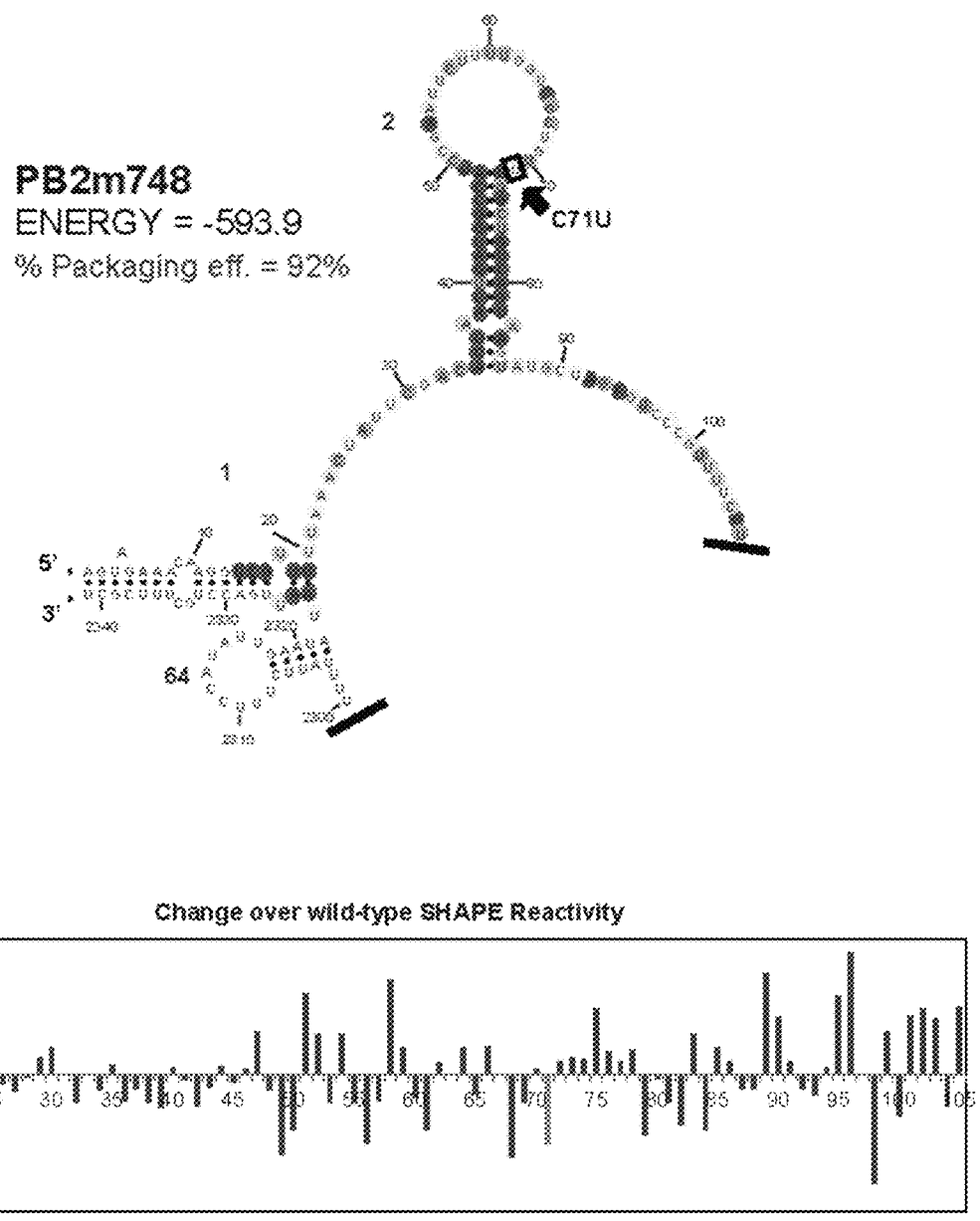

FIG. 9A-FIG. 9C shows effect of synonymous mutation on PSL2 structure. Left: Predicted RNA secondary structure of PB2 packaging mutants determined by sf-SHAPE analysis on full-length (−)-sense PB2 vRNA from PR8 strain. For clarity only, the wild-type structure is shown in upper righthand corner box. Right: SHAPE reactivity graph shown as change of mutant reactivity over wild-type. Energy values and percent packaging efficiencies indicated below figure headings. Mutants: (FIG. 9A) m731. (FIG. 9B) m751. (FIG. 9C) m748. Percent packaging efficiencies of PB2 incorporation for each of the previously described mutants are highlighted in blue.

Figure 10:
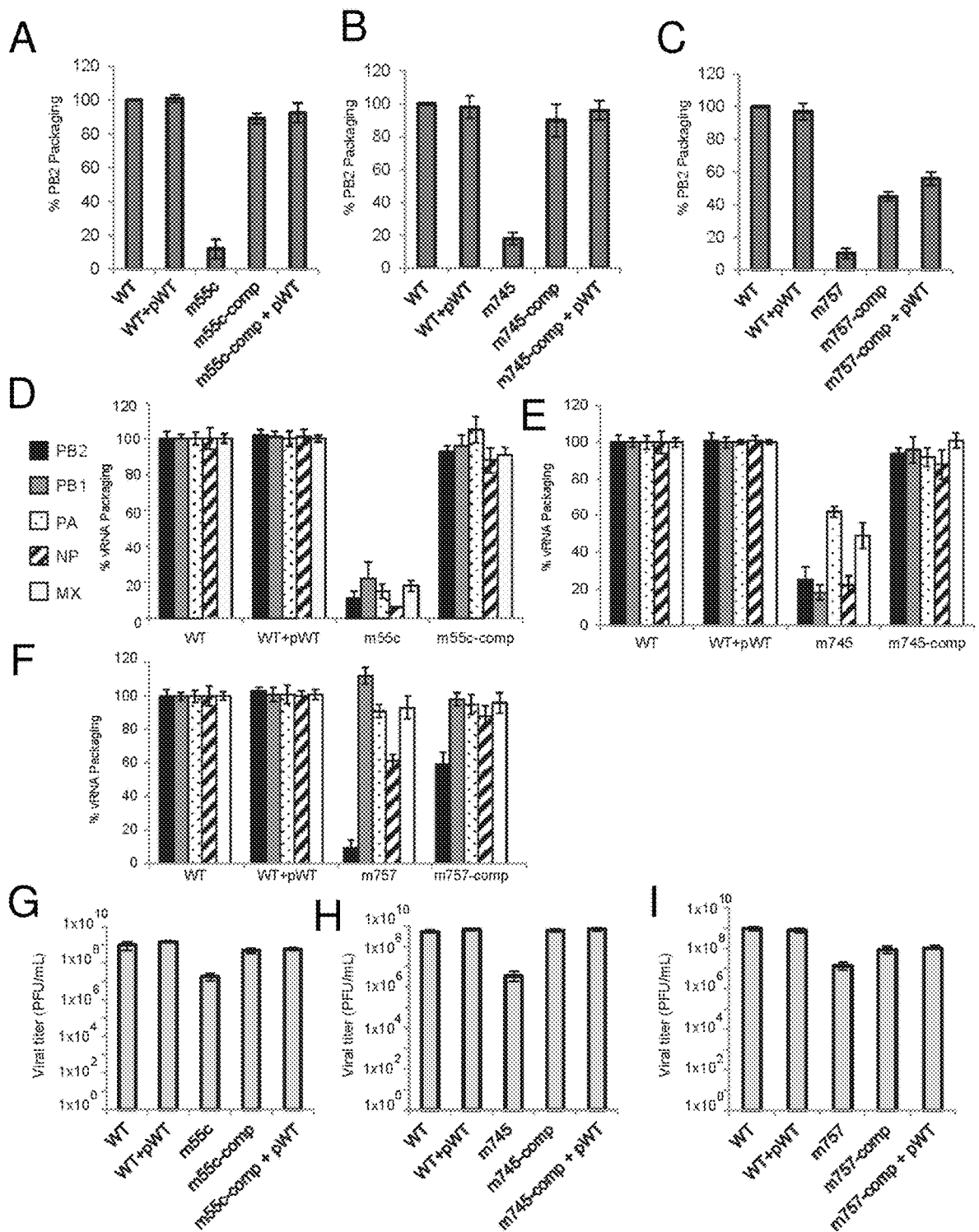
Figure 11:
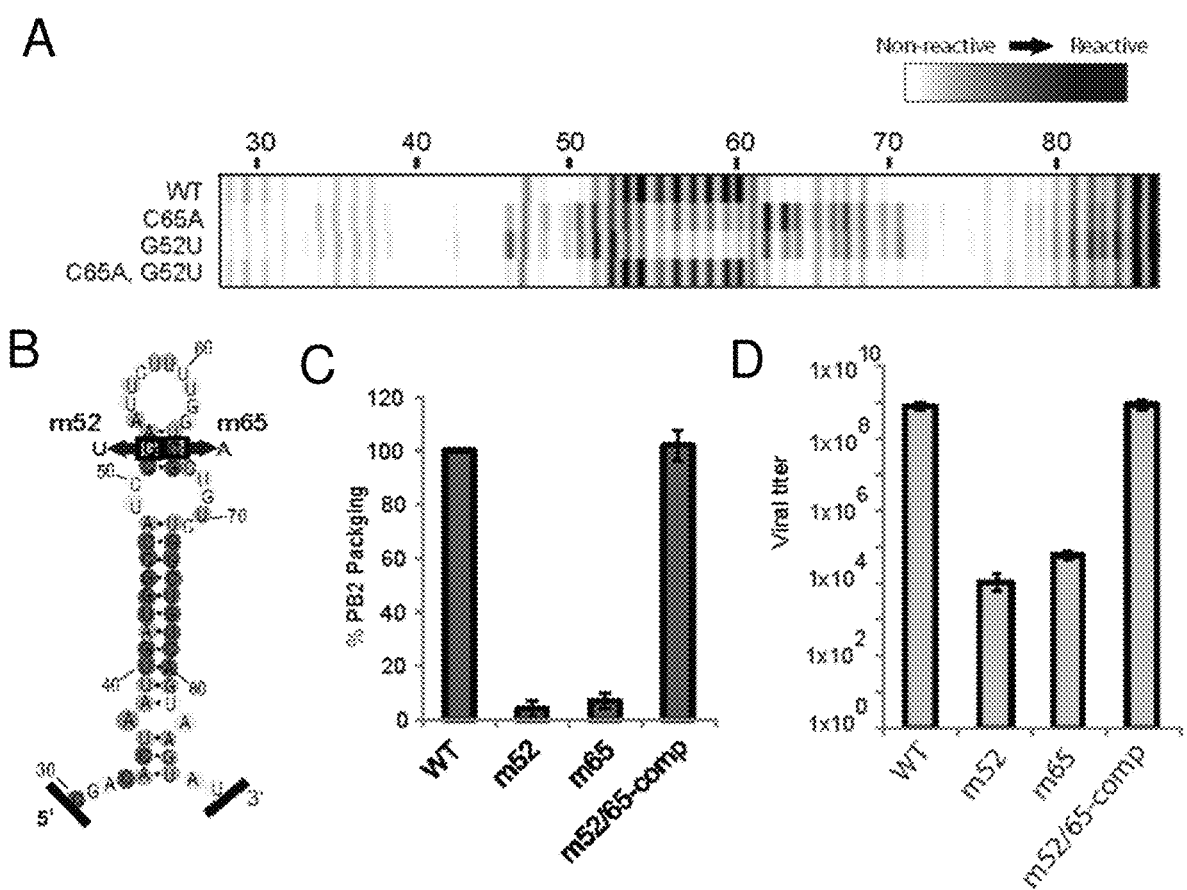
Figure 12:
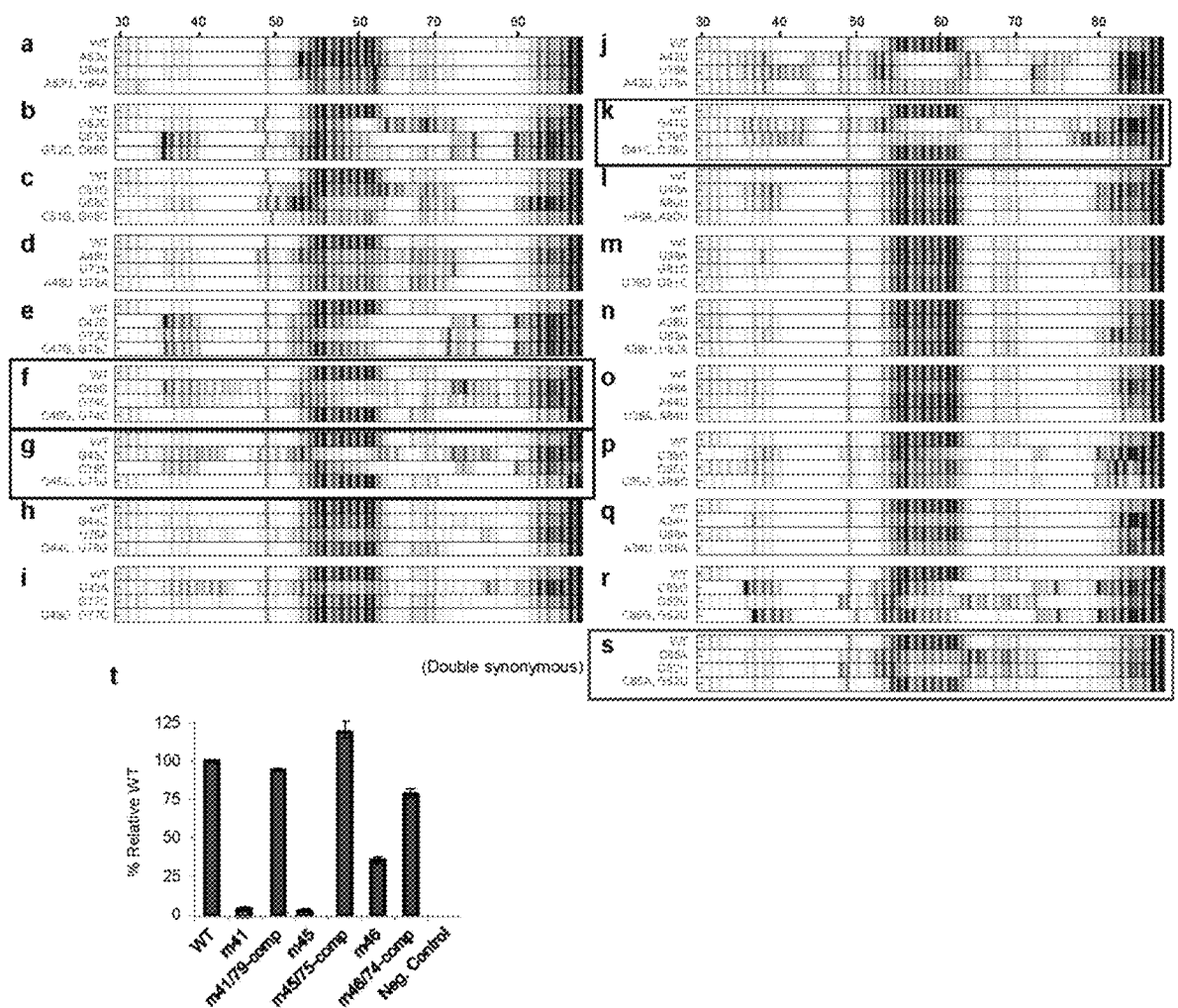

The compensatory mutations rescued not only the viral packaging for segment PB2 (FIG. 10, panels A-C, FIG. 6, panels A-B), but also other segments previously reported to be affected by the deleterious mutations, consistent with the proposed hierarchal role of PB2 in IAV packaging (Muramoto et al., 2006; Gao et al., 2012; Marsh et al., 2008) (FIG. 10, panels D-F). In addition to recovering PB2 packaging, the compensatory mutations gave complete or near-complete rescue of the viral titer loss caused by the defective mutations (FIG. 10, panels G-I). Some non-synonymous compensatory mutations were able to restore PB2 packaging better than others (m745-comp and m55c-comp, compared to m757-comp) (FIG. 10, panels A-C), possibly reflecting incomplete restoration of PB2 protein function through exogenous addition. Such exogenous addition was necessitated because some non-synonymous mutations affected both PSL2 structure and protein sequence. The most incisive test of PSL2 structure came from packaging experiments that did not require supplemental wild-type PB2 protein addition. Based on computational enumeration and multidimensional mutation-rescue experiments (Tian et al., 2014), a single mutation-rescue pair of substitutions was discovered that were both synonymous, obviating wild-type PB2 protein addition (m52/m65, FIG. 11, panels A-B, FIG. 12, panel s, FIG. 13). Making each mutation alone (m52 and m65) resulted in packaging efficiencies below 4% PB2 incorporation and titer loss exceeding 4 login—an extreme impairment beyond what has been previously reported (i.e. 2 login) for packaging-defective viruses (FIG. 11, panel C-D, FIG. 7, panel c, FIG. 10). When introduced together into a doubly mutated m52/65-comp strain that restored PSL2 structure, albeit with an altered sequence, the compensatory mutations restored both packaging efficiency and viral titer to wild-type levels.

FIG. 10, panels A-I, shows effect of compensatory mutations in PR8 PB2 packaging-defective mutants on viral packaging and titer. (FIG. 10, panels A-C) Packaging efficiencies of packaging-defective and compensatory mutant PB2 vRNAs. For compensatory mutations where a non-synonymous change was required, a wild-type PB2 protein expression plasmid was co-transfected during virus rescue. pWT=expression plasmid encoding for wild-type PR8 PB2 protein. Values given as percentage of PB2 vRNA packaging in comparison to wt parental PR8 virus. Results from two independent experiments, assays performed in triplicate (n=6). (FIG. panels D-F) Packaging efficiencies of packaging-defective and compensatory mutant viruses and their effect on the packaging of other interacting segments, PB1, PA, NP, and MX. Assays performed in triplicate (n=6). (FIG. 10, panels G-I) Viral titer by plaque assay. Results in PFU/mL, assays performed in triplicate.

FIG. 11 shows multidimensional chemical mapping reveals novel PB2 packaging-defective and compensatory mutant partners. (FIG. 11, panel A) Electropherogram result from systematic single nucleotide mutation mapping with rescue (Mutate-Map-Rescue) analysis of individual and compensatory double mutations to test base-pairings from 1-D-data-guided models and to identify predicted successful synonymous PSL2-defective and compensatory mutant pairs. Chemical accessibilities, plotted in grey scale (black=highest SHAPE reactivity), across 88 single mutations at single-nucleotide resolutions of PSL2 element from PR8 strain PB2. Reactivity peaks (left to right) correspond to nucleotides from the 5' to 3' end of the PB2 RNA. See FIG. 12 for complete list of Mutate-Rescue pairs. (FIG. 11, panel B) Mutational design of single mutants m52 (G52U) and m65 (C65A), and the double m52/65 rescue pair on the PSL2 structure. (FIG. 11, panel C) Packaging efficiency of the synonymous single and double mutant mutate-and-rescue pair. Values given as percentage of PB2 vRNA packaging in comparison to wt parental PR8 virus. Results from two independent experiments, assays performed in triplicate (n=6). (FIG. 11, panel D) Viral titer in PFU/mL, results in triplicate. Error bars represent±SD.

FIG. 12 panels a-t, shows 2-Dimensional Mutate-Map-Rescue (M2R) analysis. Mutation/Rescue results validate PSL2 RNA secondary structure. Electropherograms of SHAPE analysis with compensatory double mutations to test base-pairings from 1-D-data-guided models and to identify successful PSL2-defective and compensatory mutant pairs. Chemical accessibilities, plotted in grey scale (black=highest SHAPE reactivity), across 88 single mutations at single-nucleotide resolutions of PSL2 element from PR8 strain PB2. For each tested pairing, a "quartet" of wild-type, single mutant 1, single mutant 2, and compensatory double mutant are grouped for comparison. (FIG. 12, panels a-r) Non-synonymous mutate-and-rescue pairs. All non-boxed electropherograms are pairings for which disruption and/or rescue were not observed. Blue boxes indicate successful defective and rescue mutations. (FIG. 12, panel s) Double synonymous mutate-and-rescue pair. Green box=successful synonymous defective and rescue pair.

(FIG. 12, panel t) Packaging efficiency for non-synonymous mutate-and-rescue pairs. Values given as percentage of PB2 vRNA packaging in comparison to wt parental PR8 virus. Results from two independent experiments, assays performed in triplicate (n=6). Error bars represent±S.D.

FIG. 13 shows design of primer sequences for 2-Dimensional Mutate-Map-Rescue (M2R) mutants. SEQ ID NOs: (28-43) top to bottom. Primer sequences used for Quick-Change mutational cloning of M2R mutants into pDZ plasmids. Sequences are in (+)-sense orientation. Left field denotes synonymous (Syn.) or non-synonymous (Non-syn.) change. Highlighted nucleotides=mutation site. Boxed mutant primer set indicates double synonymous mutant partners, m52 and m65.

To test the relevance of the PSL2 structure in an in vivo model, 6-8 week old BALB/C mice were intranasally inoculated with 1000 PFU of wild-type PR8 viruses or of strains harboring mutations predicted to disrupt or restore PSL2 structure. Mice infected with the PSL2-disrupting mutations—m745 mutant strain (20% packaging efficiency) or the severely packaging-defective single mutant virus, m52 (<4% packaging efficiency)—showed reduced or no clinical signs of illness, respectively, either in weight loss or survival as compared to the PBS control (FIG. 14, panels A-B). Remarkably, inclusion of compensatory mutations that restore PSL2 structure rescued viral pathogenicity: animals infected with m52/65-comp and m745-comp, displayed comparable mortality profiles and survival curves as mice infected with wild-type PR8 (FIG. 14, panels A-B). Consistent with APLAC guidelines, all mice were humanely sacrificed upon reaching greater than 20% weight loss.

FIG. 14 panels A-B shows packaging-defective viruses are attenuated in vivo. Percent weight loss and survival of mice infected with single PSL2-disrupting and compensatory, PSL2-restoring double-mutant viruses. 6-8 week old BALB/C female mice were intranasally infected with 1000 PFU of PR8 wild-type (wt) virus, packaging defective single mutant viruses, m52 and m745, compensatory double mutant viruses, m52/65 and m745-comp, or PBS control. Mice were monitored daily for percent day 0 weight loss and percent survival. Results as an average of two independent experiments, 6 mice per condition. (FIG. 14, panel A) Percent weight loss. (FIG. 14, panel B) Kaplan-Meir survival plot of the individual cohorts depicted in (FIG. 14, panel A).

Example 2

Therapeutic Design and Targeting of PSL2 Structure Inhibits IAV Infection In Vitro and In Vivo To explore the therapeutic potential of targeting PSL2-mediated viral packaging, nine locked nucleic acids (LNAs) containing phosphorothioate internucleoside linkages (Vester and Wengel, 2004) were designed against key residues predicted to disrupt the overall RNA secondary structure of the element and thereby inhibit viral production (FIG. 15, panel A). Two of the designed LNAs, LNA8a and LNA9, are identical in sequence to LNA6 and LNA7, respectively, but possess 6-7 unmodified (non-locked) DNA nucleotides optimized for RNase-H activation (see, e.g., LNA 6/8-RNaseH; and LNA 7/9-RNaseH respectively). First, to assess the impact that LNA binding has on PSL2 RNA secondary structure, toeprinting and SHAPE chemical mapping were performed on PB2 vRNA in the presence of the LNAs. In corroboration with the antiviral assay results, sequences encoded in LNAs 6-9 exhibited the greatest ability to bind and disrupt the wild-type PSL2 structure (FIG. 16).

FIG. 15, panels A-D shows Locked Nucleic Acids targeting PSL2 RNA structure display potent antiviral activity in vitro and in vivo. (FIG. 15, panel A) Location of complementary Locked Nucleic Acids (LNAs) designed against different regions of the PSL2 structure. (FIG. 15, panel B) To screen the LNAs for antiviral activity, MDCK cells were pretreated with 100 nM of each designated LNA by Lipofectamine transfection for 1 hr prior to infection with 0.01 MOI of either PR8 (H1N1) virus or A/Hong Kong/8/68 (H3N2) virus. 48 hours post-infection, supernatant was collected and viral titers determined by plaque assay. Results from 2 independent experiments, assays performed in triplicate (n=6). (FIG. 15, panel C) Time course of pre-treatment (RX) versus post-infection treatment with LNA9 at titrating concentrations (100 nM, 10 nM, 1 nM). WT+Lipo=infection with Lipofectamine control. Pretreatment: confluent MDCK cells in 6-well plates were treated with LNA9 either 2 hours or 4 hours prior to infection. Treated supernatant was removed at the indicated time point and cells were infected with 0.01 MOI of wt PR8 virus for one hour. For post-infection treatment: MDCK cells were infected with 0.01 MOI of PR8 virus for one hour, after which the supernatant was replaced and the cells were treated with LNA9 at either 2 or 4 hours post-infection. Supernatant was collected 48 hrs later, and viral titers determined by plaque assay in triplicate. FIG. 15, panel d shows the effects of intranasal LNA treatment on survival of virus-infected mice. Mice were intranasally administered 20 ug of LNA9, scrambled LNA, or PBS (uninfected control) at 12 hours prior to infection with PR8 virus. All mice received two additional treatments at 8 hpi and 36 hpi (n=7 mice per condition).

As depicted herein in FIG. 15, panels A-D, sequence label "LNA8" refers to sequence LNA8a (SEQ ID NO:188), e.g., as described herein. Further, in FIG. 15, panels A-D, FIG. 16A, and FIG. 16B, LNA 6/8 refers to sequences LNA6 (SEQ ID NO:72) and LNA8a (SEQ ID NO:155), e.g., as described herein.

FIG. 16A-FIG. 16B shows SHAPE analysis on LNA-RNA binding. (FIG. 16A) Electrophoretic profile of SHAPE analysis performed on LNAs 1, 2, 4, 5, 6/8a, and 7/9 (100 nM) in the presence of PR8 PB2 vRNA. 51, a small molecule that interacts with the Hepatitis C virus IRES RNA was added as a control for RNA binding. Columns on the left, unlabeled reaction without SHAPE reagent, 1M7. Right: with labeling reagent. (FIG. 16B) Electrophoretic profile of SHAPE performed on LNA-vRNA combination in titrating concentrations of LNA. For each LNA, the left set of columns is without labeling reagent.

Then, in a first pilot experiment to determine the antiviral potential of LNA-mediated targeting of PSL2 across two different IAV subtypes, MDCK cells were pre-treated with 100 nM of each LNA and delivered by Lipofectamine™ transfection for 1 hour prior to infection with 0.01 MOI of either the wild-type PR8 (H1N1) virus or tissue-culture adapted A/Hong Kong/8/68 (HK68) (H3N2) virus. Forty-eight hours post-infection, the supernatants were collected and viral production was measured by plaque assay (FIG. 15, panel B). LNAs directed against only the top loop of PSL2 (LNA1, LNA4) had little to no effect on viral titer. Similarly, LNAs 3 and 5, which target the 3' base of PSL2, also failed to inhibit viral production. In contrast, nucleotide coverage of both the top loop and middle bulge by LNA6 resulted in greater than 2 $\log_{10}$ titer deficits for PR8 (FIG. 15, panels A-B). LNA8a, the RNase-H activated copy of LNA6, produced even greater antiviral activity against both viruses of up to 3 logs. Most strikingly, LNA9, the RNase-H activated copy of LNA7, possessed the strongest antiviral capacity, dropping viral production by nearly 5 logs and 4 logs against PR8 and HK68, respectively.

Figure 15:
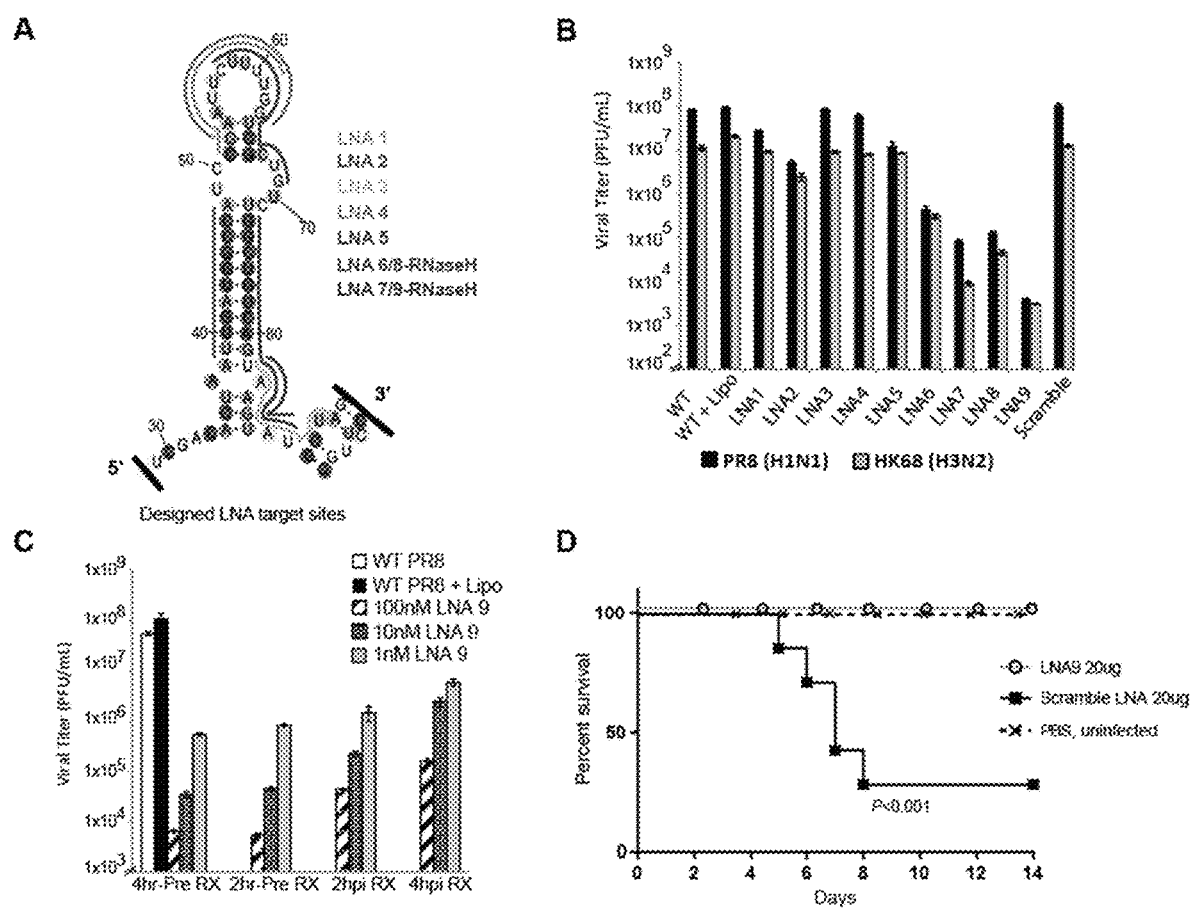
Figure 16A:
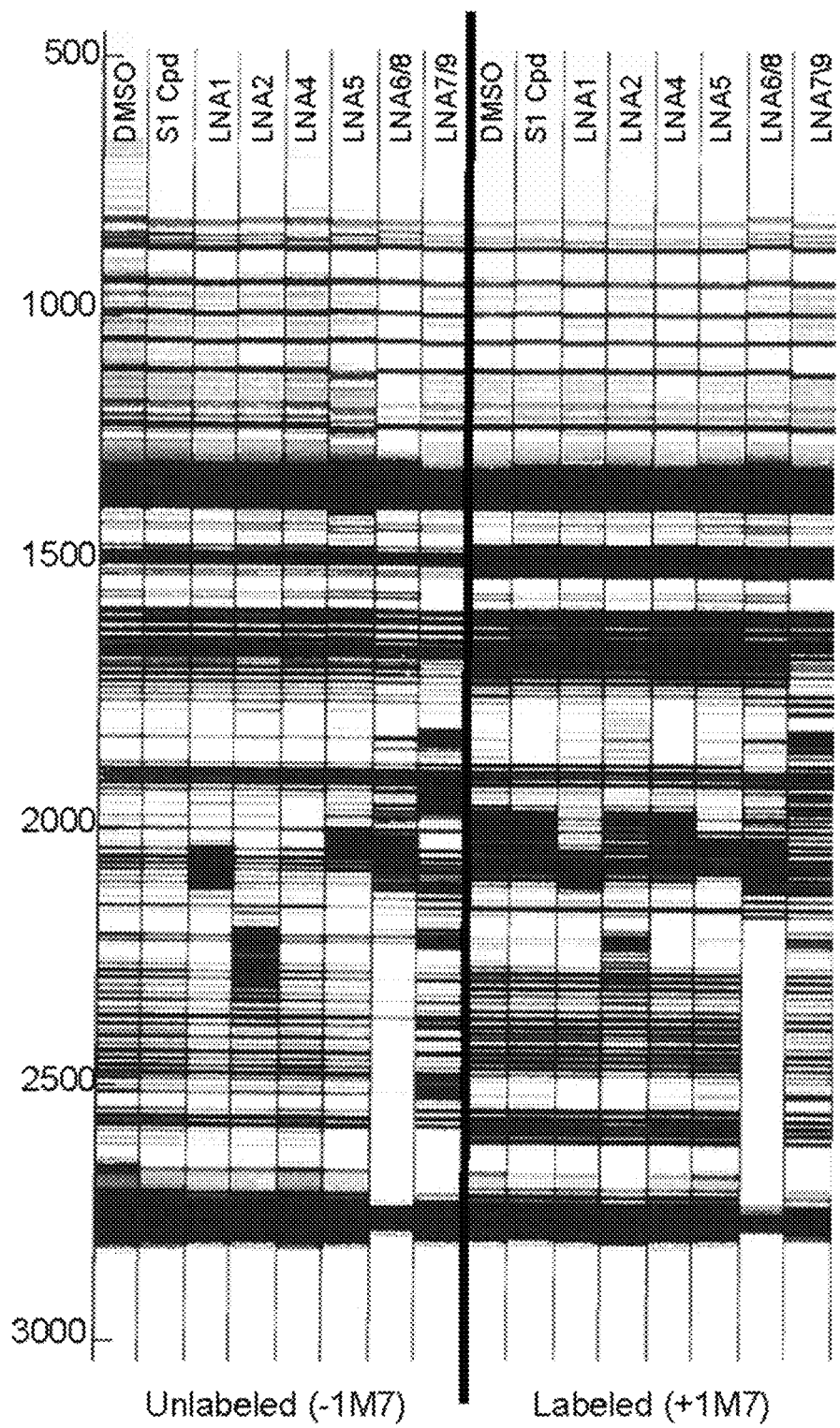
Figure 16B:
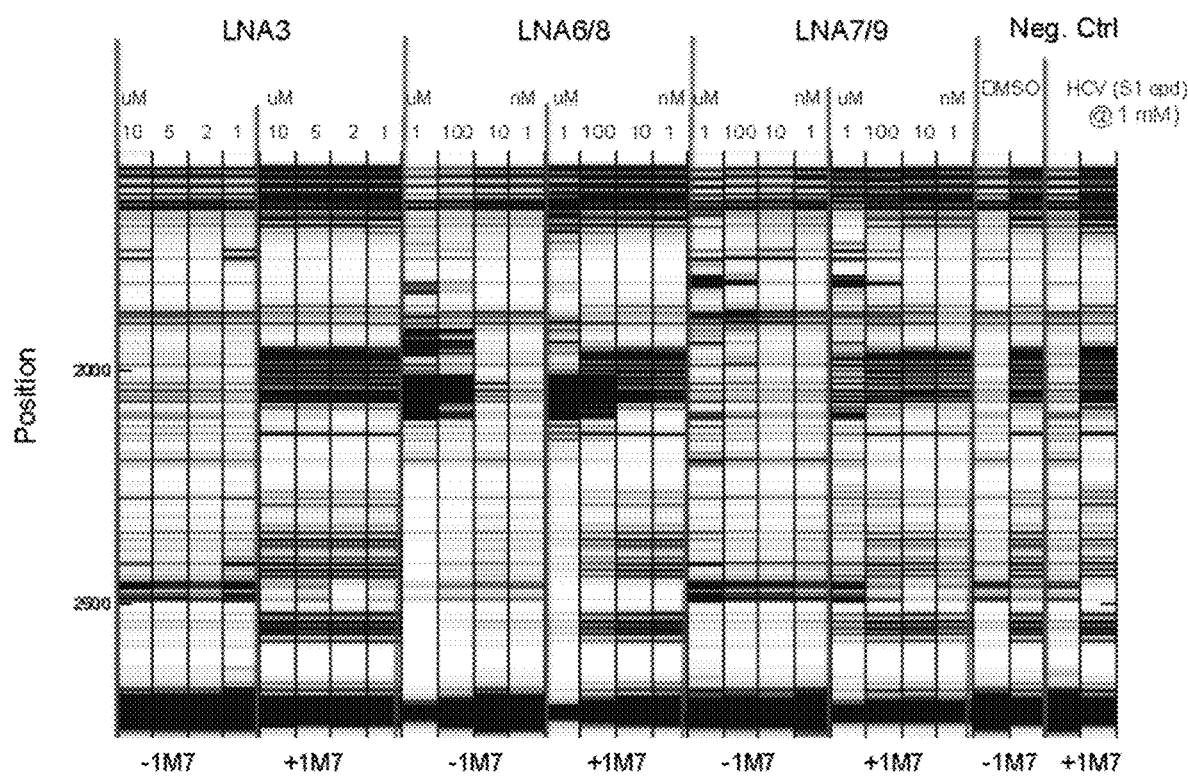

Having identified the optimal candidate LNAs, the treatment time-course and concentration parameters of LNA9's antiviral activity were further investigated. MDCK cells were treated with one dose of 10-fold dilutions of LNA9 at either 2 or 4 hours pre-infection or, alternatively, 2 or 4 hours post-infection with 0.01 MOI of wild-type PR8 virus. Cells pre-treated with the LNA had the most potent antiviral response (greater than 4 logs), and displayed strong viral inhibition (greater than 2 logs) even at the lowest dilution (1 nM) (FIG. 15, panel C). There was a trend towards decreasing antiviral activity as the time post-infection treatment increased, but even at the latest tested time point of addition, greater than 3 logs suppression of viral titer was achieved.

Example 3

In Vivo Efficacy Experiment: Extended Single-Dose Prophylaxis

Balb/C female mice (5 mice/group) were pre-treated intranasally with a single dose of 20 ug LNA9 either 3 days before infection (Day −3) or 1 day before infection (Day −1) with a lethal dose of wild-type PR8 virus. Mice were monitored daily for weight loss, clinical score, and survival. FIG. 17, panel A shows the percent survival of mice over time. FIG. 17, panel B shoes the percent weight loss over time after administration.

A single administration of 20 ug LNA9 three days prior to infection completely protected mice from fatal influenza disease. Non-treated control mice were humanely sacrificed when they lost greater than 25% weight loss, at an average of 5.5 days. In contrast, the pretreatment group showed minimal weight loss, little-to-no clinical signs of disease, and fully recovered to pre-infection weight.

This result demonstrates that a single, inhalable dose of LNA9 administered days before infection can provide lasting protection against fatal disease, and suggests the subject compounds can find use in prophylaxis treatment during influenza outbreaks and pandemics.

Example 4

Susceptibility of Influenza Viruses to Oseltamivir and LNA9, After Serial Passaging in the Presence of Drug: Drug Selection Experiment Oseltamivir (Tamiflu) is the most widely used and stockpiled neuraminidase inhibitor (NAI) on the market. Like all NAIs, oseltamivir requires a conformational rearrangement in the viral neuraminidase (NA) protein to accommodate the drug. Any mutations in the NA protein that affect this rearrangement reduce the binding affinity of oseltamivir, thus reducing drug efficacy. Notably, the H274Y mutant (also known as the H275Y mutation depending on nomenclature) is most commonly associated with oseltamivir resistance. The rapid selection of the H274Y mutation in an immunocompromised patient can lead to clinical failure of the last-resort NAI drug, peramivir, suggesting that the selection for multi-drug resistant viruses in immunocompromised hosts may be more common than previously believed. This, together with the recent spread of oseltamivir-resistant and NAI-resistant viruses in circulation, indicates the need to reevaluate usage of NAIs in general. The development of new classes of antivirals is imperative in order to reduce the adverse impact current and future influenza pandemics can have on human health.

The sequence region in segment PB2 that contains the PSL2 stemloop is highly conserved across IAV subtypes, strains and isolates from a wide range of host-species, and likely reflects a strict biologic requirement for its preservation. SHAPE analysis of this region confirmed maintenance of the PSL2 structure between seasonal as well as pandemic viruses of different subtypes and host origins, strongly suggesting that this structural element could be a novel pan-genotypic therapeutic target (and hence LNA9 has broad spectrum potential against IAV isolates). Additionally, since the subject LNAs are directed against a highly conserved viral genomic RNA target that clearly has strong constraints on its ability to mutate, the subject LNAs targeting PSL2 are expected to have a higher barrier to the development of resistance compared to NAIs.

Figure 18:
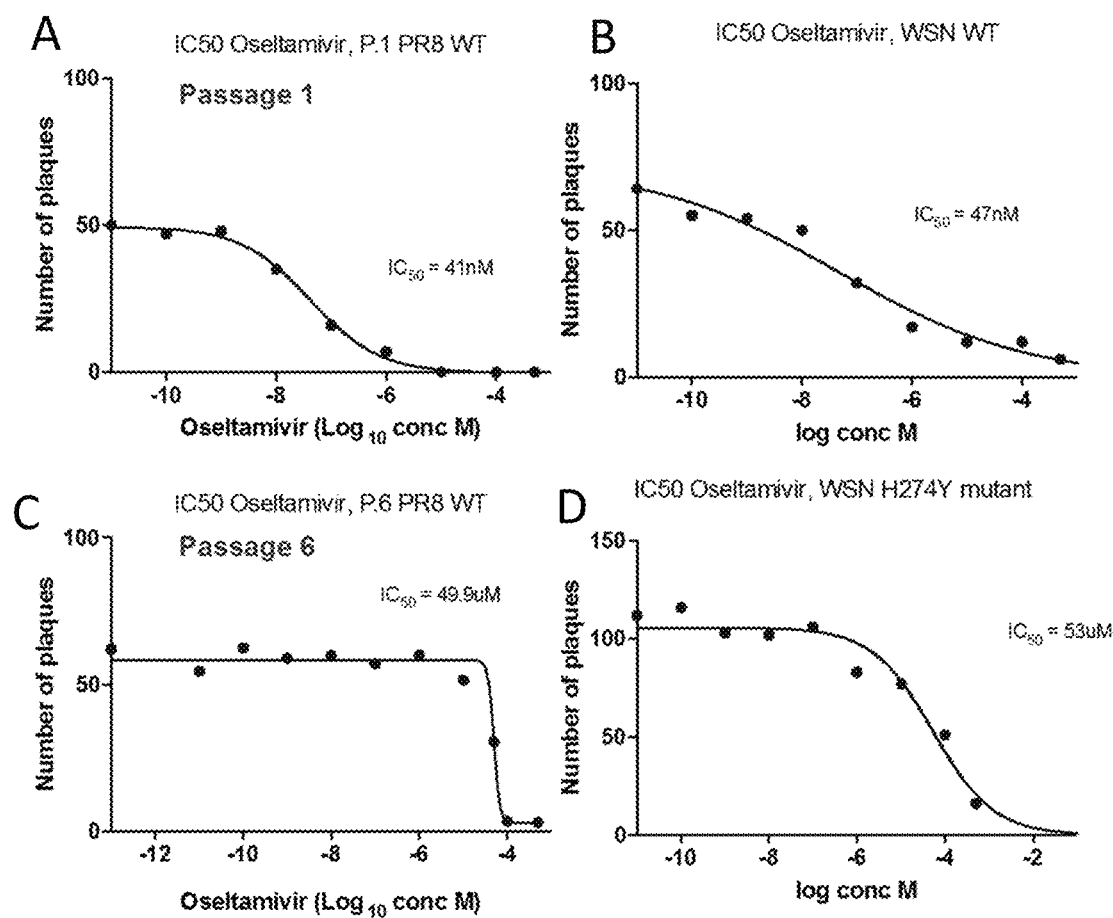

The susceptibility of influenza viruses to LNA9 versus oseltamivir after serial passages under drug pressure was investigated. Oseltamivir had a starting $IC_{50}$ of 41 nM against PR8 at passage 1 of drug treatment, as determined by a plaque reduction assay. After only six virus passages with increasing amounts of drug, the $IC_{50}$ of oseltamivir leapt to 50 uM—a 1000× increase fold. See FIG. 18, panels A-D. In comparison, after 10 passages of virus in the presence of LNA9, the $IC_{50}$ held stable from 18 to 16 pM. FIG. 19, panels A and B.

LNA9 can also be used to treat drug resistant viruses. A drug-resistant mutant of A/WSN/33 (H1N1) virus was generated using a reverse genetic virus rescue system that mutated the NA gene to contain the H274Y resistance mutation. Against this virus, oseltamivir has an $IC_{50}$ of 53 uM. Importantly, LNA9 maintained its potency and efficacy against the WSN H274Y virus with picomolar activity. FIG. 19, panel C. This result is strong evidence for the therapeutic treatment of NAI-resistant viruses with PSL2-targeting LNAs. This result also highlights the activity of LNA9 against different IAV isolates.

REFERENCES

1. M. J. Memoli, R. J. Hrabal, A. Hassantoufighi, M. C. Eichelberger, J. K. Taubenberger, Rapid selection of oseltamivir- and peramivir-resistant pandemic H1N1 virus during therapy in 2 immunocompromised hosts. Clin Infect Dis 50, 1252-1255 2010); published online Epub-May 1 (10.1086/651605).
2. R. Hai, M. Schmolke, V. H. Leyva-Grado, R. R. Thangavel, I. Margine, E. L. Jaffe, F. Krammer, A. Solorzano, A. Garcia-Sastre, P. Palese, N. M. Bouvier, Influenza A(H7N9) virus gains neuraminidase inhibitor resistance without loss of in vivo virulence or transmissibility. Nature communications 4, 2854 (2013)10.1038/ncomms3854).
3. F. G. Hayden, M. D. de Jong, Emerging influenza antiviral resistance threats. J Infect Dis 203, 6-10 (2011); published online EpubJan 1 (10.1093/infdis/jiq012).
4. X. Liu, T. Li, Y. Zheng, K. W. Wong, S. Lu, H. Lu, Poor responses to oseltamivir treatment in a patient with influenza A (H7N9) virus infection. Emerging microbes & infections 2, e27 (2013); published online EpubMay (10.1038/emi.2013.30).
5. J. Parsons, M. P. Castaldi, S. Dutta, S. M. Dibrov, D. L. Wyles, T. Hermann, Conformational inhibition of the hepatitis C virus internal ribosome entry site RNA. Nat Chem Biol 5, 823-825 (2009); published online EpubNov (10.1038/nchembio.217).

6. C. Romero-Lopez, A. Berzal-Herranz, Unmasking the information encoded as structural motifs of viral RNA genomes: a potential antiviral target. Rev Med Virol 23, 340-354 (2013); published online EpubNov (10.1002/rmv.1756).
7. P. S. Palese, M. L., Fields Virology. D. M. e. a. Knipe, Ed., Orthomyxoviridae (Lippincott Williams & Wilkins, ed. 5th, 2007).
8. R. W. Compans, J. Content, P. H. Duesberg, Structure of the ribonucleoprotein of influenza virus. J Virol 10, 795-800 (1972); published online EpubOct (
9. E. C. Hutchinson, J. C. von Kirchbach, J. R. Gog, P. Digard, Genome packaging in influenza A virus. J Gen Virol 91, 313-328 (2010); published online EpubFeb (10.1099/vir.0.017608-0).
10. T. Noda, Y. Kawaoka, Structure of influenza virus ribonucleoprotein complexes and their packaging into virions. Rev Med Virol 20, 380-391 (2010); published online EpubNov (10.1002/rmv.666).
11. Y. Muramoto, A. Takada, K. Fujii, T. Noda, K. Iwatsuki-Horimoto, S. Watanabe, T. Horimoto, H. Kida, Y. Kawaoka, Hierarchy among viral RNA (vRNA) segments in their role in vRNA incorporation into influenza A virions. J Virol 80, 2318-2325 (2006); published online EpubMar (10.1128/jvi.80.5.2318-2325.2006).
12. Q. Gao, Y. Y. Chou, S. Doganay, R. Vafabakhsh, T. Ha, P. Palese, The influenza A virus PB2, PA, NP, and M segments play a pivotal role during genome packaging. J Virol 86, 7043-7051 (2012); published online EpubJul (10.1128/jvi.00662-12).
13. G. A. Marsh, R. Rabadan, A. J. Levine, P. Palese, Highly conserved regions of influenza a virus polymerase gene segments are critical for efficient viral RNA packaging. J Virol 82, 2295-2304 (2008); published online EpubMar (10.1128/jvi.02267-07).
14. E. Fournier, V. Moules, B. Essere, J. C. Paillart, J. D. Sirbat, C. Isel, A. Cavalier, J. P. Rolland, D. Thomas, B. Lina, R. Marquet, A supramolecular assembly formed by influenza A virus genomic RNA segments. Nucleic Acids Res 40, 2197-2209 (2012); published online EpubMar (10.1093/nar/gkr985).
15. C. Gavazzi, C. Isel, E. Fournier, V. Moules, A. Cavalier, D. Thomas, B. Lina, R. Marquet, An in vitro network of intermolecular interactions between viral RNA segments of an avian H5N2 influenza A virus: comparison with a human H3N2 virus. Nucleic Acids Res 41, 1241-1254 (2013); published online EpubJan (10.1093/nar/gks1181).
16. J. R. Gog, S. Afonso Edos, R. M. Dalton, I. Leclercq, L. Tiley, D. Elton, J. C. von Kirchbach, N. Naffakh, N. Escriou, P. Digard, Codon conservation in the influenza A virus genome defines RNA packaging signals. Nucleic Acids Res 35, 1897-1907 (2007)10.1093/nar/gkm087).
17. W. N. Moss, S. F. Priore, D. H. Turner, Identification of potential conserved RNA secondary structure throughout influenza A coding regions. Rna 17, 991-1011 (2011); published online EpubJun (10.1261/rna.2619511).
18. Y. Liang, T. Huang, H. Ly, T. G. Parslow, Mutational analyses of packaging signals in influenza virus PA, PB1, and PB2 genomic RNA segments. J Virol 82, 229-236 (2008); published online EpubJan (10.1128/JVI.01541-07).
19. K. A. Wilkinson, E. J. Merino, K. M. Weeks, Selective 2'-hydroxyl acylation analyzed by primer extension (SHAPE): quantitative RNA structure analysis at single nucleotide resolution. Nature protocols 1, 1610-1616 (2006)10.1038/nprot.2006.249).
20. P. S. Pang, M. Elazar, E. A. Pham, J. S. Glenn, Simplified RNA secondary structure mapping by automation of SHAPE data analysis. Nucleic Acids Res 39, e151 (2011); published online EpubDec (10.1093/nar/gkr773).
21. S. F. Priore, W. N. Moss, D. H. Turner, Influenza A virus coding regions exhibit host-specific global ordered RNA structure. PLoS One 7, e35989 (2012)10.1371/journal.pone.0035989).
22. W. Kladwang, R. Das, A mutate-and-map strategy for inferring base pairs in structured nucleic acids: proof of concept on a DNA/RNA helix. Biochemistry 49, 7414-7416 (2010); published online EpubSep 7 (10.1021/bi01123g).
23. S. Tian, P. Cordero, W. Kladwang, R. Das, High-throughput mutate-map-rescue evaluates SHAPE-directed RNA structure and uncovers excited states. Rna 20, 1815-1826 (2014); published online EpubNov (10.1261/rna.044321.114).
24. B. Vester, J. Wengel, LNA (locked nucleic acid): high-affinity targeting of complementary RNA and DNA. Biochemistry 43, 13233-13241 (2004); published online EpubOct 26 (10.1021/bi0485732).
25. K. Klumpp, R. W. Ruigrok, F. Baudin, Roles of the influenza virus polymerase and nucleoprotein in forming a functional RNP structure. Embo J 16, 1248-1257 (1997); published online EpubMar 17 (10.1093/emboj/16.6.1248).
26. R. Coloma, J. M. Valpuesta, R. Arranz, J. L. Carrascosa, J. Ortin, J. Martin-Benito, The structure of a biologically active influenza virus ribonucleoprotein complex. PLoS Pathog 5, e1000491 (2009); published online EpubJun (10.1371/journal.ppat.1000491).
27. F. Baudin, C. Bach, S. Cusack, R. W. Ruigrok, Structure of influenza virus RNP. I. Influenza virus nucleoprotein melts secondary structure in panhandle RNA and exposes the bases to the solvent. Embo J 13, 3158-3165 (1994); published online EpubJul 1 (
28. T. Coelho, D. Adams, A. Silva, P. Lozeron, P. N. Hawkins, T. Mant, J. Perez, J. Chiesa, S. Warrington, E. Tranter, M. Munisamy, R. Falzone, J. Harrop, J. Cehelsky, B. R. Bettencourt, M. Geissler, J. S. Butler, A. Sehgal, R. E. Meyers, Q. Chen, T. Borland, R. M. Hutabarat, V. A. Clausen, R. Alvarez, K. Fitzgerald, C. Gamba-Vitalo, S. V. Nochur, A. K. Vaishnaw, D. W. Sah, J. A. Gollob, O. B. Suhr, Safety and efficacy of RNAi therapy for transthyretin amyloidosis. N Engl J Med 369, 819-829 (2013); published online EpubAug 29 (10.1056/NEJMoa1208760).
29. K. Fitzgerald, M. Frank-Kamenetsky, S. Shulga-Morskaya, A. Liebow, B. R. Bettencourt, J. E. Sutherland, R. M. Hutabarat, V. A. Clausen, V. Karsten, J. Cehelsky, S. V. Nochur, V. Kotelianski, J. Horton, T. Mant, J. Chiesa, J. Ritter, M. Munisamy, A. K. Vaishnaw, J. A. Gollob, A. Simon, Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet 383, 60-68 (2014); published online EpubJan 4 (10.1016/S0140-6736(13)61914-5).
30. J. Gottlieb, M. R. Zamora, T. Hodges, A. W. Musk, U. Sommerwerk, D. Dilling, S. Arcasoy, J. DeVincenzo, V. Karsten, S. Shah, B. R. Bettencourt, J. Cehelsky, S. Nochur, J. Gollob, A. Vaishnaw, A. R. Simon, A. R. Glanville, ALN-RSV01 for prevention of bronchiolitis obliterans syndrome after respiratory syncytial virus infection in lung transplant recipients. J Heart Lung Transplant 35, 213-221 (2016); published online EpubFeb (10.1016/j.healun.2015.08.012).
31. E. Hoffmann, G. Neumann, Y. Kawaoka, G. Hobom, R. G. Webster, A DNA transfection system for generation of influenza A virus from eight plasmids. Proc Natl Acad Sci USA 97, 6108-6113 (2000); published online EpubMay 23 (10.1073/pnas.100133697).
32. K. J. Szretter, A. L. Balish, J. M. Katz, Influenza: propagation, quantification, and storage. Current protocols in microbiology Chapter 15, Unit 15G 11 (2006); published online EpubDec (10.1002/0471729256.mc15g01s3).
33. G. A. Marsh, R. Hatami, P. Palese, Specific residues of the influenza A virus hemagglutinin viral RNA are important for efficient packaging into budding virions. J Virol 81, 9727-9736 (2007); published online EpubSep (10.1128/jvi.01144-07).
34. S. A. Mortimer, K. M. Weeks, Time-resolved RNA SHAPE chemistry: quantitative RNA structure analysis in one-second snapshots and at single-nucleotide resolution. Nature protocols 4, 1413-1421 (2009)10.1038/nprot.2009.126).
35. A. Akbari, G. Marthinsen, J. T. Lifjeld, F. Albregtsen, L. Wennerberg, N. C. Stenseth, K. S. Jakobsen, Improved DNA fragment length estimation in capillary electrophoresis. Electrophoresis 29, 1273-1285 (2008); published online EpubMar (10.1002/elps.200700523).
36. P. S. Pang, E. A. Pham, M. Elazar, S. G. Patel, M. R. Eckart, J. S. Glenn, Structural map of a microRNA-122: hepatitis C virus complex. J Virol 86, 1250-1254 (2012); published online EpubJan (10.1128/JVI.06367-11).
37. K. E. Deigan, T. W. Li, D. H. Mathews, K. M. Weeks, Accurate SHAPE-directed RNA structure determination. Proc Natl Acad Sci USA 106, 97-102 (2009); published online EpubJan 6 (10.1073/pnas.0806929106).
38. P. De Rijk, J. Wuyts, R. De Wachter, RnaViz 2: an improved representation of RNA secondary structure. Bioinformatics 19, 299-300 (2003); published online EpubJan 22.
39. W. Kladwang, C. C. VanLang, P. Cordero, R. Das, A two-dimensional mutate-and-map strategy for non-coding RNA structure. Nature chemistry 3, 954-962 (2011); published online EpubDec (10.1038/nchem.1176).
40. W. Kladwang, P. Cordero, R. Das, A mutate-and-map strategy accurately infers the base pairs of a 35-nucleotide model RNA. Rna 17, 522-534 (2011); published online EpubMar (10.1261/rna.2516311).
41. P. Cordero, W. Kladwang, C. C. VanLang, R. Das, in RNA Folding (Methods in Molecular Biology), C. Waldsich, Ed. (2013), pp. in press.
42. S. A. Mortimer, K. M. Weeks, A fast-acting reagent for accurate analysis of RNA secondary and tertiary structure by SHAPE chemistry. J Am Chem Soc 129, 4144-4145 (2007); published online EpubApr 11 (10.1021/ja0704028).
43. S. Yoon, J. Kim, J. Hum, H. Kim, S. Park, W. Kladwang, R. Das, HiTRACE: high-throughput robust analysis for capillary electrophoresis. Bioinformatics 27, 1798-1805 (2011); published online EpubJul 1 (10.1093/bioinformatics/btr277).
44. H. Kim, P. Cordero, R. Das, S. Yoon, HiTRACE-Web: an online tool for robust analysis of high-throughput capillary electrophoresis. Nucleic Acids Research 41, W492-W498 (2013); published online EpubJuly 1, 2013 (10.1093/nar/gkt501).
45. J. Kim, S. Yu, B. Shim, H. Kim, H. Min, E.-Y. Chung, R. Das, S. Yoon, A robust peak detection method for RNA structure inference by high-throughput contact mapping. Bioinformatics 25, 1137-1144 (2009); published online EpubMay 1, 2009 (10.1093/bioinformatics/btp110).
46. W. Kladwang, T. H. Mann, A. Becka, S. Tian, H. Kim, S. Yoon, R. Das, Standardization of RNA chemical mapping experiments. Biochemistry 53, 3063-3065 (2014); published online EpubMay 20 (10.1021/bi5003426).
47. D. H. Mathews, M. D. Disney, J. L. Childs, S. J. Schroeder, M. Zuker, D. H. Turner, Incorporating chemical modification constraints into a dynamic programming algorithm for prediction of RNA secondary structure. Proc Natl Acad Sci USA 101, 7287-7292 (2004); published online EpubMay 11 (10.1073/pnas.0401799101).
48. K. Darty, A. Denise, Y. Ponty, VARNA: Interactive drawing and editing of the RNA secondary structure. Bioinformatics 25, 1974-1975 (2009); published online EpubAug 1 (10.1093/bioinformatics/btp250).
49. P. Cordero, J. B. Lucks, R. Das, An RNA Mapping DataBase for curating RNA structure mapping experiments. Bioinformatics 28, 3006-3008 (2012); published online EpubNov 15 (10.1093/bioinformatics/bts554).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

Notwithstanding the appended claims, the disclosure set forth herein is also described by the following clauses:

Clause 1. An oligonucleotide compound, comprising an oligonucleotide sequence complementary to a PB2 vRNA region, wherein the region comprises nucleotides 34-87 in the (−)-sense notation of the 5′ terminal coding region of the PB2 vRNA, or a salt thereof.

Clause 2. The compound of clause 1, comprising an oligonucleotide sequence comprising at least 8 nucleoside subunits complementary to the region of PB2 vRNA.

Clause 3. The compound of any one of clauses 1-2, wherein the oligonucleotide is complementary to a region of the Packaging Stem-Loop 2 (PSL2) motif of the region of PB2 vRNA.

Clause 4. The compound of any one of clauses 1-3, wherein the oligonucleotide comprises an internucleoside linkage selected from: phosphorothioate, phosphorodithioate, phosphoramidate and thiophosphoramidate linkages.

Clause 5. The compound of any one of clauses 1-4, wherein all of the internucleoside linkages of the oligonucleotide are selected from: phosphorothioate, phosphorodithioate, phosphoramidate, thiophosphoramidate and phosphodiester linkages.

Clause 6. The compound of any one of clause 4 or 5, wherein the oligonucleotide internucleoside linkage is chiral.

Clause 7. The compound on any one of clauses 1-5, wherein the oligonucleotide comprises a bridged nucleic acid (BNA) nucleotide.

Clause 8. The compound of any one of clauses 1-5, wherein the oligonucleotide comprises a locked nucleic acid (LNA) nucleotide.

Clause 9. The compound of any one of clauses 1-5, wherein the oligonucleotide comprises a ethylene-bridged nucleic acid (ENA) nucleotide.

Clause 10. The compound of any one of clauses 1-5, wherein the oligonucleotide comprises a constrained ethyl nucleic acid (cEt) nucleotide.

Clause 11. The compound of any one of clauses 1-5, wherein the oligonucleotide comprises a 2'-modified nucleotide.

Clause 12. The compound of any one of clauses 1-11, wherein the oligonucleotide comprises a sequence selected from:

```
                                       (SEQ ID NO: 45)
    5' ACCAAAAGAAT 3';

(SEQ ID NO: 46)
    5' TGGCCATCAAT 3';

(SEQ ID NO: 47)
    5' TAGCATACTTA 3';

(SEQ ID NO: 48)
    5' CCAAAAGA 3';

(SEQ ID NO: 49)
    5' CATACTTA 3';

(SEQ ID NO: 50)
    5' CAGACACGACCAAAA 3';

(SEQ ID NO: 51)
    5' TACTTACTGACAGCC 3';

(SEQ ID NO: 52)
    5' AGACACGACCAAAAG 3';

(SEQ ID NO: 53)
    5' ACCAAAAGAAT 3';

(SEQ ID NO: 54)
    5' TGGCCATCAAT 3';

(SEQ ID NO: 55)
    5' TAGCATACTTA 3';

(SEQ ID NO: 56)
    5' CGACCAAAAGAATTC 3';

(SEQ ID NO: 57)
    5' CGACCAAAAGAATTC 3';

(SEQ ID NO: 58)
    5' GATGGCCATCAATTA 3';

(SEQ ID NO: 59)
    5' GATGGCCATCAATTA 3';

(SEQ ID NO: 60)
    5' TCTAGCATACTTACT 3';

(SEQ ID NO: 61)
    5' TCTAGCATACTTACT 3';

(SEQ ID NO: 62)
    5' GAATTCGGATGGCCA 3';

(SEQ ID NO: 63)
    5' GGCCATCAATTAGTG 3';

(SEQ ID NO: 64)
    5' TTCGGATGGCCATCA 3';

(SEQ ID NO: 65)
    5' AGCCAGACAGCGA 3';

(SEQ ID NO: 66)
    5' GACAGCCAGACAGCA 3';

(SEQ ID NO: 98)
    5' CGACCAAAAGAATT 3';

(SEQ ID NO: 99)
    5' GACCAAAAGAATTCGG 3';

(SEQ ID NO: 100)
    5' AGCATACTTACTGACA 3';

(SEQ ID NO: 101)
    5' CATACTTACTGACA 3';

(SEQ ID NO: 102)
    5' ATACTTACTGACAG 3';

(SEQ ID NO: 103)
    5' CATACTTACTGACAGC 3';

(SEQ ID NO: 104)
    5' AGACAGCGACCAAAAG 3';

(SEQ ID NO: 105)
    5' ACAGCGACCAAAAG;

(SEQ ID NO: 106)
    5' CAGCCAGACAGCGAC 3';

(SEQ ID NO: 107)
    5' CAGCCAGACAGCGA 3';

(SEQ ID NO: 108)
    5' ACAGCCAGACAGCGA 3';

(SEQ ID NO: 109)
    5' GACAGCCAGACAGCG 3';

(SEQ ID NO: 110)
    5' CATCAATTAGTGTCG 3';

(SEQ ID NO: 111)
    5' CCATCAATTAGTGTCG 3';

(SEQ ID NO: 112)
    5' GCCATCAATTAGTGTG 3';

(SEQ ID NO: 113)
    5' AAGAATTCGGATGGC 3';

(SEQ ID NO: 114)
    5' CAGACAGCGACCAA 3';

(SEQ ID NO: 115)
    5' TGACAGCCAGACAGC 3';
```

Clause 13. The compound of clause 12, wherein the oligonucleotide comprises a sequence selected from:

```
                                       (SEQ ID NO: 62)
    5' GAATTCGGATGGCCA 3';
```

```
                                   (SEQ ID NO: 65)
5' AGCCAGACAGCGA 3';

(SEQ ID NO: 98)
5'CGACCAAAAGAATT 3';

(SEQ ID NO: 99)
5'GACCAAAAGAATTCGG 3';

(SEQ ID NO: 100)
5' AGCATACTTACTGACA 3';

(SEQ ID NO: 101)
5' CATACTTACTGACA 3';

(SEQ ID NO: 102)
5' ATACTTACTGACAG 3'';

(SEQ ID NO: 103)
5' CATACTTACTGACAGC 3';

(SEQ ID NO: 104)
5' AGACAGCGACCAAAAG 3';

(SEQ ID NO: 105)
5' ACAGCGACCAAAAG;

(SEQ ID NO: 106)
5'CAGCCAGACAGCGAC 3';

(SEQ ID NO: 107)
5'CAGCCAGACAGCGA 3';

(SEQ ID NO: 108)
5'ACAGCCAGACAGCGA 3';

(SEQ ID NO: 109)
5'GACAGCCAGACAGCG 3';

(SEQ ID NO: 110)
5' CATCAATTAGTGTCG 3';

(SEQ ID NO: 111)
5' CCATCAATTAGTGTCG 3';

(SEQ ID NO: 112)
5' GCCATCAATTAGTGTG 3';

(SEQ ID NO: 113)
5' AAGAATTCGGATGGC 3';

(SEQ ID NO: 114)
5' CAGACAGCGACCAA 3';
and
                                   (SEQ ID NO: 115)
5' TGACAGCCAGACAGC 3'.
```

Clause 14. The compound of clause 12, comprising an oligonucleotide having at least 70% sequence identity with a sequence selected from (SEQ ID Nos 45-66), and (SEQ ID Nos 98-115).

Clause 15. The compound of clause 14, comprising an oligonucleotide having at least 80% sequence identity with a sequence selected from (SEQ ID Nos 45-66), and (SEQ ID Nos 98-115).

Clause 16. The compound of clause 15, comprising an oligonucleotide having at least 90% sequence identity with a sequence selected from (SEQ ID Nos 45-66), and (SEQ ID Nos 98-115).

Clause 17. The compound of clause 12, wherein one or more of the nucleotides of the oligonucleotide are modified nucleotides (e.g., as described herein).

Clause 18. The compound of clause 12, wherein one or more of the nucleotides of the oligonucleotide are bridged nucleic acid (BNA) nucleotides.

Clause 19. The compound of clause 12, wherein all the nucleotides of the oligonucleotide are locked nucleic acid (LNA) nucleotides.

Clause 20. The compound of clause 12, wherein one or more of the nucleotides of the oligonucleotide are ethylene-bridged nucleic acid (ENA) nucleotides.

Clause 21. The compound of clause 12, wherein one or more of the nucleotides of the oligonucleotide are constrained ethyl nucleic acid (cEt) nucleotides.

Clause 22. The compound clause 12, wherein one or more of the nucleotides of the oligonucleotide comprise 2'-modified nucleotides.

Clause 23. The compound of clause 12, wherein the oligonucleotide comprises a sequence selected from:

```
LNA 1:
                                   (SEQ ID NO: 67)
5' AccAaaAGaaT 3';

LNA 2:
                                   (SEQ ID NO: 68)
5' TggCcATcaaT 3';

LNA 3:
                                   (SEQ ID NO: 69)
5' TagCAtActtA 3';

LNA 4:
                                   (SEQ ID NO: 70)
5' CCAAAAGA 3';

LNA 5:
                                   (SEQ ID NO: 71)
5' CATACTTA 3';

LNA 6:
                                   (SEQ ID NO: 72)
5' CagaCaCGaCCaaAA 3';

LNA 7:
                                   (SEQ ID NO: 73)
5' TAcTtaCTgaCagCC 3';

LNA 8:
                                   (SEQ ID NO: 74)
5' AGACacgaccaAAAG 3';

LNA 9:
                                   (SEQ ID NO: 75)
5' TACTtactgacaGCC 3';

LNA 9.2:
                                   (SEQ ID NO: 76)
5' TACttactgacAGCC 3';

LNA10:
                                   (SEQ ID NO: 77)
5'ACCaaaagAAT 3';

LNA11:
                                   (SEQ ID NO: 78)
5' TGGccatcAAT 3';

LNA12:
                                   (SEQ ID NO: 79)
5'TAGcatacTTA 3';

LNA13:
                                   (SEQ ID NO: 80)
5'CgacCAaaAGaattC 3';

LNA14:
                                   (SEQ ID NO: 81)
5'CGACcaaaagaATTC 3';
```

LNA15:
    (SEQ ID NO: 82)
5'GaTGgCcATcaAttA 3';

LNA16:
    (SEQ ID NO: 83)
5'GATGgccatcaATTA 3';

LNA17:
    (SEQ ID NO: 84)
5'TcTAgCaTActTacT 3';

LNA18:
    (SEQ ID NO: 85)
5'TCTAgcatactTACT 3';

LNA19:
    (SEQ ID NO: 86)
5'GAAttcggatgGCCA 3';

LNA20:
    (SEQ ID NO: 87)
5'GGCCatcaattaGTG 3';

LNA21:
    (SEQ ID NO: 88)
5'TTCGgatggccaTCA 3';

LNA22:
    (SEQ ID NO: 89)
5'AGCCagacagCGA 3';

LNA23:
    (SEQ ID NO: 90)
5'GACAgccagacaGCA 3';

LNA9.G74C:
    (SEQ ID NO: 91)
5'TACTtactgacaGTC 3';
and

LNA9.T80C:
    (SEQ ID NO: 92)
5'TACTtaccgacaGCC 3';

wherein capitalized letters denote LNA nucleotides and lowercase letters denote DNA nucleotides.

Clause 24. The compound of clause 12, wherein the oligonucleotide comprises a sequence selected from:

LNA19:
    (SEQ ID NO: 86)
5'GAAttcggatgGCCA 3';

LNA22:
    (SEQ ID NO: 89)
5'AGCCagacagCGA 3';

LNA22.2:
    (SEQ ID NO: 116)
5'CAGCcagacagCGAC 3';

LNA22.3:
    (SEQ ID NO: 117)
5'CAGccagacagCGAC 3';

LNA22.5:
    (SEQ ID NO: 118)
5'CAGccagacaGCGA 3';

LNA22.6:
    (SEQ ID NO: 119)
5'CAGccagacagCGA 3';

LNA22.7:
    (SEQ ID NO: 120)
5'CAGCcagacagCGA 3';

LNA22.8:
    (SEQ ID NO: 121)
5'ACAgccagacagCGA 3';

LNA22.9:
    (SEQ ID NO: 122)
5'ACAGccagacaGCGA 3';

LNA22.10:
    (SEQ ID NO: 123)
5'ACAgccagacaGCGA 3';

LNA22.11:
    (SEQ ID NO: 124)
5'GACAgccagacaGCG 3';

LNA22.13:
    (SEQ ID NO: 125)
5'GACagccagacaGCG 3';
and

LNA22.14:
    (SEQ ID NO: 126)
5'GACAgccagacAGCG.

Clause 25. The compound of clause 12, wherein the oligonucleotide comprises a sequence selected from:

LNA24:
    (SEQ ID NO: 127)
5'CATcaattagtgTCG 3';

LNA25:
    (SEQ ID NO: 128)
5'CCAtcaattagtgTCG 3';

LNA26:
    (SEQ ID NO: 129)
5VGCCatcaattagtGTG 3';

LNA27:
    (SEQ ID NO: 130)
5'AAGAattcggaTGGC 3';

LNA28:
    (SEQ ID NO: 131)
5' CAGacagcgacCAA 3V;
and

LNA29:
    (SEQ ID NO: 132)
5' TGAcagccagacAGC 3'.

Clause 26. The compound of clause 12, wherein the oligonucleotide comprises a sequence selected from:

LNA14:
    (SEQ ID NO: 81)
5'CGACcaaaagaATTC 3';

LNA14.5:
    (SEQ ID NO: 135)
5'CGACcaaaagaATT 3';

LNA14.8:
    (SEQ ID NO: 137)
5'CGACcaaaagaaTTC 3';

LNA14.28:
    (SEQ ID NO: 148)
5'GACcaaaagaatTCGG 3';

LNA14.30:
    (SEQ ID NO: 149)
5'GACCaaaagaattCGG 3';

-continued

```
LNA 9:
                                    (SEQ ID NO: 75)
5' TACTtactgacaGCC 3';

LNA9.1:
                                    (SEQ ID NO: 159)
5' AGCAtacttactGACA 3';

LNA9.2a:
                                    (SEQ ID NO: 160)
5' CATacttactgACA 3';

LNA9.8:
                                    (SEQ ID NO: 164)
5' ATActtactgACAG;

LNA9.12:
                                    (SEQ ID NO: 167)
5' CATActtactgacAGC;

LNA8a:
                                    (SEQ ID NO: 188)
5' AGAcagcgaccaaAAG;

LNA8a.1:
                                    (SEQ ID NO: 189)
5' AGACagcgaccaAAAG;
and LNA8a.2:
                                    (SEQ ID NO: 190)
5' ACAGcgaccaAAAG.
```

Clause 27. The compound of any one of clauses 23-26, comprising an oligonucleotide having at least 70% sequence identity with a sequence selected from (SEQ ID Nos 67-92), and (SEQ ID Nos: 116-191).

Clause 28. The compound of clause 27, comprising an oligonucleotide having at least 80% sequence identity with a sequence selected from (SEQ ID Nos 67-92), and (SEQ ID Nos: 116-191).

Clause 29. The compound of clause 28, comprising an oligonucleotide having at least 90% sequence identity with a sequence selected from (SEQ ID Nos 67-92), and (SEQ ID Nos: 116-191).

Clause 30. The compound of any one of clauses 1-29, wherein the oligonucleotide comprises at least 5 deoxyribonucleotide units and is capable of recruiting an RNase.

Clause 31. The compound of any one of clauses 1-30, wherein binding of the compound to the region of PB2 vRNA disrupts the overall secondary RNA structure of the PB2 vRNA.

Clause 32. The compound of any one of clauses 1-30, wherein binding of the compound to the region of PB2 vRNA inhibits the packaging ability of the PB2 vRNA.

Clause 33. The compound of any one of clauses 1-32, wherein the compound is an oligonucleotide conjugate having enhanced cellular uptake.

Clause 34. The compound of clause 33, wherein the compound is an oligonucleotide-lipid conjugate.

Clause 35. The compound of any one of clauses 1-33, wherein the compound is an oligonucleotide conjugate with a cell-specific protein.

Clause 36. A method of inhibiting influenza A virus in a cell, the method comprising: contacting a sample comprising viral RNA (vRNA) having a PSL2 motif with an effective amount of an agent that specifically binds the PSL2 motif to inhibit the influenza A virus.

Clause 37. The method of clause 36, wherein the agent is an oligonucleotide compound comprising at least 8 nucleoside subunits complementary to a PSL2 motif of the vRNA, or a salt thereof.

Clause 38. The method of clause 36 or 37, wherein the agent is an oligonucleotide compound according to one of clauses 1-35.

Clause 39. The method of any one of clauses 36-38, wherein the vRNA in the sample is a PB2 vRNA.

Clause 40. The method of any one of clauses 36-39, wherein contacting the sample with an agent results in at least 1 $\log_{10}$ titer deficits of the virus.

Clause 41. The method of any one of clauses 36-39, wherein contacting the sample with an agent results in at least 2 $\log_{10}$ titer deficits of the virus.

Clause 42. The method of any one of clauses 36-41, wherein the agent disrupts the overall structure of the PSL2 motif of the vRNA.

Clause 43. The method of any one of clauses 36-41, wherein the agent inhibits the packaging ability of the PSL2 motif of the vRNA.

Clause 44. The method of any one of clauses 36-41, wherein the vRNA is isolated from a virion or a cell.

Clause 45. The method of any one of clauses 36-41, wherein the vRNA is comprised in a virion or an infected cell.

Clause 46. The method of any one of clauses 36-45, wherein the sample is in vitro.

Clause 47. The method of any one of clauses 36-41 or 45, wherein the sample is in vivo.

Clause 48. A method of treating or preventing influenza A virus infection in a subject, the method comprising: administering to a subject in need thereof a pharmaceutical composition comprising an effective amount of an active agent that specifically binds to a PSL2 motif of a viral RNA (vRNA).

Clause 49. The method of clause 48, wherein the vRNA is a PB2 vRNA.

Clause 50. The method of any one of clauses 48-49, wherein the active agent is a compound comprising an oligonucleotide sequence comprising at least 8 nucleoside subunits complementary to the region of PB2 vRNA.

Clause 51. The method of any one of clauses 48-50, wherein the agent is an oligonucleotide compound according to one of clauses 1-35.

Clause 52. The method of any one of clauses 48-51, wherein the subject is at risk of influenza A virus infection and the administering of the oligonucleotide compound protects the subject against infection for 1 week or more (e.g., 2 weeks or more, 3 weeks or more, 1 month or more, 2 months or more, 3 months or more, etc).

Clause 53 The method of clause 52, wherein the administering comprises weekly, biweekly, or monthly administration of an effective dose of the oligonucleotide compound.

Clause 54. The method of any one of clauses 48-53, wherein the administering results in at least 1 $\log_{10}$ titer deficits of the virus in a sample of the subject.

Clause 55. The method of any one of clauses 48-53, wherein the administering results in at least 2 $\log_{10}$ titer deficits of the virus in a sample of the subject.

Clause 56. The method of any one of clauses 48-53, wherein the active agent is an oligonucleotide conjugate having enhanced cellular uptake.

Clause 57. The method of any one of clauses 48-55, wherein the active agent is an oligonucleotide conjugate with a cell-specific protein.

Clause 58. The method of any one of clauses 48-55, wherein the pharmaceutical composition comprises an enhancer of cellular uptake.

Clause 59. The method of any one of clauses 48-55, wherein the pharmaceutical composition further comprises an additional active agent selected from a second oligonucleotide active agent and an antiviral drug.

Clause 60. The method of any one of clauses 48-55, wherein the active agent is an siRNA, an shRNA, an antisense RNA, or an antisense DNA.

Clause 61. The method of any one of clauses 48-55, wherein the subject is at risk of influenza A virus infection, and the method prevents infection.

Clause 62. The method of any one of clauses 48-55, wherein the subject is diagnosed with or suspect of having an influenza A virus infection, and the method treats infection.

Clause 63. A method for screening a candidate agent for the ability to inhibit influenza A virus in a cell, the method comprising:

contacting a sample comprising viral RNA (vRNA) comprising a PSL2 motif with a candidate agent; and determining whether the candidate agent specifically binds to the PSL2 motif;

wherein an agent that specifically binds to the PSL2 motif will inhibit influenza A virus in a cell.

Clause 64. The method of clause 63, wherein the candidate agent is selected from: a small molecule, a nucleic acid and a polypeptide.

Clause 65. The method of clause 64, wherein the determining step comprises detecting a cellular parameter, wherein a change in the parameter in the cell as compared to in a cell not contacted with candidate agent indicates that the candidate agent specifically binds the PSL2 motif.

Clause 66. The method of any one of clauses 63-65, wherein an agent that specifically binds to the PSL2 motif will treat the subject having the influenza A virus infection.

What is claimed is:

1. An oligonucleotide compound or salt thereof, comprising an oligonucleotide sequence comprising one or more modified ribose moieties and at least 8 nucleoside subunits complementary to a region of a Packaging Stem-Loop 2 (PSL2) motif of a PB2 viral RNA (vRNA) or mutant thereof, wherein said region includes nucleotides on both strands of the upper stem of the PSL2 motif, and wherein the oligonucleotide compound inhibits virus production.

2. The compound of claim 1, wherein the oligonucleotide comprises an internucleoside linkage selected from: phosphorothioate, phosphorodithioate, phosphoramidate and thiophosphoramidate linkages.

3. The compound of claim 2, wherein the oligonucleotide comprises one or more chiral internucleoside linkages.

4. The compound of claim 1, wherein the oligonucleotide comprises a bridged nucleic acid (BNA) nucleotide.

5. The compound of claim 4, wherein the BNA nucleotide is selected from the group consisting of, locked nucleic acid (LNA) nucleotides, ethylene-bridged nucleic acid (ENA) nucleotides, and constrained ethyl (cEt) nucleotides.

6. The compound of claim 1, wherein the oligonucleotide comprises one or more 2'-modified nucleotides.

7. The compound of claim 1, wherein the oligonucleotide comprises the sequence.

(SEQ ID NO: 56)

5' CGACCAAAAGAATTC 3';

8. The compound of claim 1, wherein the oligonucleotide comprises a sequence selected from:

```
                                             (SEQ ID NO: 98)
    5'CGACCAAAAGAATT 3'; and (SEQ ID NO: 99)
    5'GACCAAAAGAATTCGG 3'.
```

9. The compound of claim 1, comprising an oligonucleotide sequence having at least 70% sequence identity with a sequence selected from SEQ ID NOs. 56 and 98-99.

10. The compound of claim 8, wherein the oligonucleotide comprises at least 5 deoxyribonucleotide units and is capable of recruiting an RNase.

11. The compound of claim 1, wherein the oligonucleotide comprises a sequence selected from:

```
LNA14.1:                                     (SEQ ID NO: 133)
5' GCGAccaaaagaATT 3';

LNA14.2:                                     (SEQ ID NO: 134)
5' GCGAccaaaagAATT 3';

LNA14.5:                                     (SEQ ID NO: 135)
5' CGACcaaaagaATT3';

LNA14.7:                                     (SEQ ID NO: 136)
5' CGAccaaaagaATTC 3';

LNA14.8:                                     (SEQ ID NO: 137)
5' CGACcaaaagaTTC 3';

LNA14.9:                                     (SEQ ID NO: 138)
5' CGAccaaaagaTTC 3';

LNA14.10:                                    (SEQ ID NO: 139)
5' GACcaaaagaTTC 3';

LNA14.14:                                    (SEQ ID NO: 140)
5' GCGAccaaaagaATTC 3';

LNA14.15:                                    (SEQ ID NO: 141)
5' GCGaccaaaagaATTC 3';

LNA14.16:                                    (SEQ ID NO: 142)
5' GCGaccaaaagaaTTC 3';

LNA14.17:                                    (SEQ ID NO: 143)
5' CGAccaaaagaaTTCG 3';

LNA14.19:                                    (SEQ ID NO: 144)
5' CGACcaaaagaaTTCG 3';

LNA14.22:                                    (SEQ ID NO: 145)
5' GACcaaaagaaTTC 3';

LNA14.24:                                    (SEQ ID NO: 146)
5' ACCAaaagaaTTC 3';

LNA14.27:                                    (SEQ ID NO: 147)
5' CGAccaaaagaatTCGG 3';

LNA14.28:                                    (SEQ ID NO: 148)
5' GACcaaaagaatTCGG 3';

LNA14.30:                                    (SEQ ID NO: 149)
5' GACCaaaagaattCGG 3';

LNA14.31:                                    (SEQ ID NO: 150)
5' GACcaaaagaattCGG 3';
and LNA14.32:                                    (SEQ ID NO: 151)
5' ACCAaaagaattCGGA 3',
``` wherein capitalized letters denote LNA nucleotides and lowercase letters denote DNA nucleotides.

12. The compound of claim 1, comprising an oligonucleotide sequence having at least 70% sequence identity with a sequence selected from SEQ ID NOs. 133-151.

13. A method of inhibiting influenza A virus in a cell, the method comprising:
    contacting a sample comprising viral RNA (vRNA) having a PSL2 motif with an effective amount of the oligonucleotide compound according to claim 1.

14. The method of claim 13, wherein contacting the sample with an agent results in at least 1 $\log_{10}$ titer deficits of the virus or the agent disrupts the overall structure of the PSL2 motif of the vRNA.

15. The method of claim 13, wherein the vRNA is isolated from a virion or a cell.

16. A method of treating or preventing influenza A virus infection in a subject, the method comprising:
    administering to a subject in need thereof a pharmaceutical composition comprising an effective amount of the oligonucleotide compound according to claim 1.

17. The method of claim 16, wherein the subject is at risk of influenza A virus infection and the administering of the oligonucleotide compound protects the subject against infection for 1 week or more.

18. The method of claim 17, wherein the administering comprises weekly, biweekly, or monthly administration of an effective dose of the oligonucleotide compound.

19. The method of claim 16, wherein the pharmaceutical composition further comprises an additional active agent selected from a second oligonucleotide active agent and an antiviral drug.

20. The method of claim 16, wherein the subject has been diagnosed with or suspect of having an influenza A virus infection.

21. The compound of claim 7, wherein the oligonucleotide comprises a bridged nucleic acid (BNA) nucleotide.

22. The compound of claim 21, wherein the BNA nucleotide is selected from the group consisting of, locked nucleic acid (LNA) nucleotides, ethylene-bridged nucleic acid (ENA) nucleotides, and constrained ethyl (cEt) nucleotides.

23. The compound of claim 8, wherein the oligonucleotide comprises a bridged nucleic acid (BNA) nucleotide.

24. The compound of claim 23, wherein the BNA nucleotide is selected from the group consisting of, locked nucleic acid (LNA) nucleotides, ethylene-bridged nucleic acid (ENA) nucleotides, and constrained ethyl (cEt) nucleotides.

25. The compound of claim 1, wherein said region includes nucleotides of the upper stem region of the PSL2 motif corresponding to positions 52 and 65 of the wild type PB2 sequence set forth as SEQ ID NO: 1.

26. An oligonucleotide compound or salt thereof, comprising an oligonucleotide sequence comprising one or more modified ribose moieties and at least 8 nucleoside subunits complementary to a region of a Packaging Stem-Loop 2 (PSL2) motif of a PB2 viral RNA (vRNA) or mutant thereof, wherein the oligonucleotide compound has a length of 15 nucleotides or less, comprises the sequence 5' AGCCA-GACAGCGA 3' (SEQ ID NO: 65), and inhibits virus production.

27. The compound of claim 26, wherein the oligonucleotide comprises:
    an internucleoside linkage selected from: phosphorothioate, phosphorodithioate, phosphoramidate and thiophosphoramidate linkages, and/or
    a bridged nucleic acid (BNA) selected from the group consisting of, locked nucleic acid (LNA) nucleotides, ethylene-bridged nucleic acid (ENA) nucleotides, and constrained ethyl (cEt) nucleotides.

28. The compound of claim 26, wherein the oligonucleotide comprises a sequence selected from:

```
5' CAGCCAGACAGCGAC 3';                    (SEQ ID NO: 106)

5' CAGCCAGACAGCGA 3';                     (SEQ ID NO: 107)
and

5' ACAGCCAGACAGCGA 3'.                    (SEQ ID NO: 108)
```

29. The compound of claim 28, wherein the oligonucleotide comprises:

an internucleoside linkage selected from: phosphorothioate, phosphorodithioate, phosphoramidate and thiophosphoramidate linkages, and/or a bridged nucleic acid (BNA) selected from the group consisting of, locked nucleic acid (LNA) nucleotides, ethylene-bridged nucleic acid (ENA) nucleotides, and constrained ethyl (cEt) nucleotides.

30. The compound of claim 26, wherein the oligonucleotide comprises a sequence selected from:

```
LNA22:                                    (SEQ ID NO: 89)
5' AGCCagacagCGA 3';

LNA22.2:                                  (SEQ ID NO: 116)
5' CAGCcagacagCGAC 3';

LNA22.3:                                  (SEQ ID NO: 117)
5' CAGccagacagCGAC 3';

LNA22.5:                                  (SEQ ID NO: 118)
5' CAGccagacaGCGA 3';

LNA22.6:                                  (SEQ ID NO: 119)
5' CAGccagacagCGA 3';

LNA22.7:                                  (SEQ ID NO: 120)
5' CAGCcagacagCGA 3';

LNA22.8:                                  (SEQ ID NO: 121)
5' ACAgccagacagCGA 3';

LNA22.9:                                  (SEQ ID NO: 122)
5' ACAGccagacaGCGA 3';
and LNA22.10:                                 (SEQ ID NO: 123)
5' ACAgccagacaGCGA 3',
``` wherein capitalized letters denote LNA nucleotides and lowercase letters denote DNA nucleotides.

31. An oligonucleotide compound or salt thereof, comprising an oligonucleotide sequence comprising one or more modified ribose moieties and at least 8 nucleoside subunits complementary to a region of a Packaging Stem-Loop 2 (PSL2) motif of a PB2 viral RNA (vRNA) or mutant thereof, wherein the oligonucleotide compound inhibits virus production and comprises the sequence ACAGCCAGACAGCGA (SEQ ID NO: 108) or GACAGCCAGACAGCG (SEQ ID NO: 109).

32. The compound of claim 31, wherein the oligonucleotide comprises:

an internucleoside linkage selected from: phosphorothioate, phosphorodithioate, phosphoramidate and thiophosphoramidate linkages, and/or a bridged nucleic acid (BNA) selected from the group consisting of, locked nucleic acid (LNA) nucleotides, ethylene-bridged nucleic acid (ENA) nucleotides, and constrained ethyl (cEt) nucleotides.

33. The compound of claim 31, wherein the oligonucleotide comprises a sequence selected from:

```
LNA22.8:                                  (SEQ ID NO: 121)
5' ACAgccagacagCGA 3';

LNA22.9:                                  (SEQ ID NO: 122)
5' ACAGccagacaGCGA 3';

LNA22.10:                                 (SEQ ID NO: 123)
5' ACAgccagacaGCGA 3';

LNA22.11:                                 (SEQ ID NO: 124)
5' GACAgccagacaGCG 3';

LNA22.13:                                 (SEQ ID NO: 125)
5' GACagccagacaGCG 3';
and LNA22.14:                                 (SEQ ID NO: 126)
5' GACAgccagacAGCG,
``` wherein capitalized letters denote LNA nucleotides and lowercase letters denote DNA nucleotides.

* * * * *

SEQUENCE LISTING

```
<160> NUMBER OF SEQ ID NOS: 191

<210> SEQ ID NO 1
<211> LENGTH: 196
<212> TYPE: RNA
<213> ORGANISM: Artificial Sequence
<220> FEATURE:
<223> OTHER INFORMATION: Synthetic polynucleotide

<400> SEQUENCE: 1
aguagaaaca ggucguuuu uaaacuauuc gacacuaauu gauggccauc cgaauucuuu      60
uggucgcugu cuggcuguca guaaguaugc uagagucccg uuuucguuuc auuaccaaca    120
ccacgucucc uugcccaauu agcacauuag ccuuuuuuau ucuuuccaua uugaauauaa    180
uugaccugcu uucgcu                                                   196

<210> SEQ ID NO 2
<211> LENGTH: 182
<212> TYPE: RNA
<213> ORGANISM: Artificial Sequence
<220> FEATURE:
<223> OTHER INFORMATION: Synthetic polynucleotide

<400> SEQUENCE: 2
aguagaaaca ggucguuuu uaaacuauuc gacacuaauu gaucgccauc cgaauucuuu      60
uggucgcugu cuggcuguca guaaguaugc uagagucccg uuuucguuuc gcgagacugc    120
gacauuagau uucuuaguuc uuuuauucuu uccauauuga auauaauuga ccugcuuucg    180
cu                                                                  182

<210> SEQ ID NO 3
<211> LENGTH: 197
<212> TYPE: RNA
<213> ORGANISM: Artificial Sequence
<220> FEATURE:
<223> OTHER INFORMATION: Synthetic polynucleotide

<400> SEQUENCE: 3
aguagaaaca ggucguuuuu aaacuauucg acacuaauug auggccaucc gaauucuuuu      60
ggucgcuguc uggcugucug uaaguaugcu agagucccgu uucguuucg gacucucaaa    120 aacgugcgag acugcgacau uagauuucuu aguucuuuua uucuuuccau auugaauaua    180
auugaccugc uuucgcu                                                  197

<210> SEQ ID NO 4
```

```
<211> LENGTH: 158
<212> TYPE: RNA
<213> ORGANISM: Artificial Sequence
<220> FEATURE:
<223> OTHER INFORMATION: Synthetic polynucleotide

<400> SEQUENCE: 4
aguagaaaca aggucguuuu uaaacuauuc gacacuaauu gaugauggcc auccgaauuc      60
uuuuggucgc ugucuggcug ucaguaagua ugcuagaguc ccguuuccgu uucauuacca    120
acaccacguc ucuugaauau aauugaccug cuuucgcu                             158

<210> SEQ ID NO 5
<211> LENGTH: 178
<212> TYPE: RNA
<213> ORGANISM: Artificial Sequence
<220> FEATURE:
<223> OTHER INFORMATION: Synthetic polynucleotide

<400> SEQUENCE: 5
aguagaaaca aggucguuuu uaaauaauuc gacacuaauu gauggccauc cgaauucuuu     60
uggucgcugu cuggcuguca guaaguaugc uagagucccg uuucguuuc auuaccaaca     120 ccacgcucuc cuugcccuuuu auucucucca uauugaauau auuugaccug cuuucgcu    178

<210> SEQ ID NO 6
<211> LENGTH: 289
<212> TYPE: RNA
<213> ORGANISM: Artificial Sequence
<220> FEATURE:
<223> OTHER INFORMATION: Synthetic polynucleotide

<400> SEQUENCE: 6
aguagaaaca aggucguuuu uaaacuauuc gacacuaauu gauggccauc cgaauucuuu     60
uggucgcugu cuggcuguca guaaguaugc uagagucccg uuucguuuc auuaccaaca     120 cuacgucccc uugcccaauu agcacauuag ccuucucucc uuuugcaaga ugcucaguu    180 cauugaugcu aaugcugggc cauaucucuu gucuucuuug cccaaaauga gaaauccucu    240
caggacagca uauucucucc auauugaaua uaauugaccu gcuuucgcu                289

<210> SEQ ID NO 7
<211> LENGTH: 177
<212> TYPE: RNA
<213> ORGANISM: Artificial Sequence
<220> FEATURE:
<223> OTHER INFORMATION: Synthetic polynucleotide

<400> SEQUENCE: 7
aguagaaaca aggucguuuu uaaacuauuc gacacuaauu gauggccauc cgaauucuuu     60
uggucgcugu cuggcuguca guaaguaugc uagagucccg uuucguuuca uuaccaacac    120
cacgucuccu ugcccuuuua uucuuuccau auugaauaua auugaccugc uuucgcu      177

<210> SEQ ID NO 8
<211> LENGTH: 197
<212> TYPE: RNA
<213> ORGANISM: Artificial Sequence
<220> FEATURE:
<223> OTHER INFORMATION: Synthetic polynucleotide

<400> SEQUENCE: 8
aguagaaaca aggucguuuu uaaacuauuc gacacuaauu gauggccauc cgaauucuuu     60
uggucgcugu cuggcuguca guuaauaugc uagagucccg uuucguuuc auuaccaaca     120
```

```
ccacgucucc uugcccaauu agcacgucga uagguuuuuu auucuuucca uauugaauau    180
aaugaccugc uuucgcu                                                  197
```

<210> SEQ ID NO 9
<211> LENGTH: 198
<212> TYPE: RNA
<213> ORGANISM: Artificial Sequence
<220> FEATURE:
<223> OTHER INFORMATION: Synthetic polynucleotide

<400> SEQUENCE: 9

```
aguagaaaca aggucguuuu uaaacuauuc gacacuaauu gauggccauc cgaauucuuu    60
uggucgcugu cuggcugucu guaaguaugc uagaguCCCg uuucguuuc ggacucucaa    120 aaacgugcga gacugcgaca uuagauuucu aguucuuuu auucuuucca uauugaauau    180 aaugaccug cuuucgcu                                                  198
```

<210> SEQ ID NO 10
<211> LENGTH: 178
<212> TYPE: RNA
<213> ORGANISM: Artificial Sequence
<220> FEATURE:
<223> OTHER INFORMATION: Synthetic polynucleotide

<400> SEQUENCE: 10

```
aguagaaaca aggucguuuu uaaacuauuc gacaucuaau ugauggccau ccgaauucuu    60
uuggucgcug ucuggcuguc aguaaguaug cuagagucCC guuucguuu gacugcgaca    120 uuagauuucu aguucuuuu auucuuucca uauugaauau aauugaccug cuuucgcu     178
```

<210> SEQ ID NO 11
<211> LENGTH: 182
<212> TYPE: RNA
<213> ORGANISM: Artificial Sequence
<220> FEATURE:
<223> OTHER INFORMATION: Synthetic polynucleotide

<400> SEQUENCE: 11

```
aguagaaaca aggucguuuu uaaacuauuc gacacuaauu gaucgccauc cgaauucuuu    60
uggucgcugu cuggcuguca guaaguaugc uagaguCCCg uuucguuuc gcgagacugc    120 gacauuagau uucuuaguuc uuuuauucuu uccauauuga auauaauuga ccugcuuucg    180
cu                                                                 182
```

<210> SEQ ID NO 12
<211> LENGTH: 59
<212> TYPE: RNA
<213> ORGANISM: Artificial Sequence
<220> FEATURE:
<223> OTHER INFORMATION: Synthetic polynucleotide

<400> SEQUENCE: 12

```
cgacacuaau ugauggccau ccgaauucuu uuggucgcug ucuggcuguc aguaaguau     59
```

<210> SEQ ID NO 13
<211> LENGTH: 59
<212> TYPE: RNA
<213> ORGANISM: Artificial Sequence
<220> FEATURE:
<223> OTHER INFORMATION: Synthetic polynucleotide

<400> SEQUENCE: 13
cgacacuaau ugauggccau ccgaauucuu uuggucgcug ucuggcuguc aguaaguau        59

<210> SEQ ID NO 14
<211> LENGTH: 108
<212> TYPE: DNA
<213> ORGANISM: Artificial Sequence
<220> FEATURE:
<223> OTHER INFORMATION: Synthetic polynucleotide

<400> SEQUENCE: 14
attgggcaag gagacgtggt gttggtaatg aaacggaaac ggaactctag catacttact        60
gacagccaga cagcgaccaa aagaattcgg atggccatca attagtgt                    108

<210> SEQ ID NO 15
<211> LENGTH: 108
<212> TYPE: DNA
<213> ORGANISM: Artificial Sequence
<220> FEATURE:
<223> OTHER INFORMATION: Synthetic polynucleotide

<400> SEQUENCE: 15
attgggcaag gagacgtcgt gttggtaatg aaacggaaac ggaactctag catattaaca        60
gacagccaaa cagcgacgaa aagaattcgg atggcgatca attgatgt                    108

<210> SEQ ID NO 16
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 16
tacttactga cagtcagaca gcg                                                23

<210> SEQ ID NO 17
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 17
cgctgtctga ctgtcagtaa gta                                                23

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 18
tacttactga ctcgcagaca gcg                                                23

<210> SEQ ID NO 19
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 19
cgctgtctgc gagtcagtaa gta                                                23

```
<210> SEQ ID NO 20
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 20
tgacagccag actgcgacca aaagaattcg                                        30

<210> SEQ ID NO 21
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 21
cgaattcttt tggtcgcagt ctggctgtca                                        30

<210> SEQ ID NO 22
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 22
agcgaccaaa agcattcgga tggc                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 23
gccatccgaa tgcttttggt cgct                                              24

<210> SEQ ID NO 24
<211> LENGTH: 175
<212> TYPE: RNA
<213> ORGANISM: Artificial Sequence
<220> FEATURE:
<223> OTHER INFORMATION: Synthetic polynucleotide

<400> SEQUENCE: 24
aguagaaaca aggucguuuu uaaacuauuc gacacuaauu gauggccauc cgaauucuuu        60
uggucgcugu cggcugucag uaaguaugcu agagucccgu uuucguuuca uuaccaacac       120
gacgucuccu ugcuuuuauu cuuuccauau ugaauauaau ugaccugcuu ucgcu            175

<210> SEQ ID NO 25
<211> LENGTH: 151
<212> TYPE: RNA
<213> ORGANISM: Artificial Sequence
<220> FEATURE:
<223> OTHER INFORMATION: Synthetic polynucleotide

<400> SEQUENCE: 25
aguagaaaca aggucguuuu uaaacuauuc gacacuaauu gauggccauc cgaauucuuu        60
ucgucgcugu cuggcuguca guaaguaugc uagagucccg uuuucguuuc uuuauucuuu       120
ccauauugaa uauaauugac cugcuuucgc u                                     151
```

<210> SEQ ID NO 26
<211> LENGTH: 148
<212> TYPE: RNA
<213> ORGANISM: Artificial Sequence
<220> FEATURE:
<223> OTHER INFORMATION: Synthetic polynucleotide

<400> SEQUENCE: 26
agugaaacaa ggucguuuuu aaacuauucg acacuaauug auggccaucc gaauucuuuu    60
ggucgcuguu uggcugucag uaaguaugcu agagucccgu uuuaguuuuu auucuuucca   120
uauugaauau aauugaccug cuuucgcu                                      148

<210> SEQ ID NO 27
<211> LENGTH: 59
<212> TYPE: RNA
<213> ORGANISM: Artificial Sequence
<220> FEATURE:
<223> OTHER INFORMATION: Synthetic polynucleotide

<400> SEQUENCE: 27
cgacacuaau ugauggccau ccgaauucuu uuggucgcug ucuggcuguc aguaaguau     59

<210> SEQ ID NO 28
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 28
agaattcgga tgcccatcaa ttagtgtcg                                     29

<210> SEQ ID NO 29
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 29
cgacactaat tgatgggcat ccgaattct                                     29

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 30
tacttactga caggcagaca gcg                                           23

<210> SEQ ID NO 31
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 31
cgctgtctgc ctgtcagtaa gta                                           23

<210> SEQ ID NO 32
<211> LENGTH: 25

<212> TYPE: DNA
<213> ORGANISM: Artificial Sequence
<220> FEATURE:
<223> OTHER INFORMATION: Synthetic polynucleotide

<400> SEQUENCE: 32
ttcggatggg catcaattag tgtcg                                           25

<210> SEQ ID NO 33
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 33
cgacactaat tgatgcccat ccgaa                                           25

<210> SEQ ID NO 34
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 34
atacttactg acacccagac agcg                                            24

<210> SEQ ID NO 35
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 35
cgctgtctgg gtgtcagtaa gtat                                            24

<210> SEQ ID NO 36
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 36
tcggatggcc atgaattagt gtcg                                            24

<210> SEQ ID NO 37
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 37
cgacactaat tcatggccat ccga                                            24

<210> SEQ ID NO 38
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 38
agcatactta ctcacagcca gacagc    26

<210> SEQ ID NO 39
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 39
gctgtctggc tgtgagtaag tatgct    26

<210> SEQ ID NO 40
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 40
ccaaaagaat taggatggcc atcaattagt gtcg    34

<210> SEQ ID NO 41
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 41
cgacactaat tgatggccat cctaattctt ttgg    34

<210> SEQ ID NO 42
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 42
gacagccaga cagctaccaa aagaattcg    29

<210> SEQ ID NO 43
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 43
cgaattcttt tggtagctgt ctggctgtc    29

<210> SEQ ID NO 44
<211> LENGTH: 71
<212> TYPE: RNA
<213> ORGANISM: Artificial Sequence
<220> FEATURE:
<223> OTHER INFORMATION: Synthetic polynucleotide

<400> SEQUENCE: 44
ucgacacuaa uugauggcca uccgaauucu uuggucgcu gucuggcugu caguaaguau    60
gcuagccuug c    71

<210> SEQ ID NO 45
<211> LENGTH: 11

<210> SEQ ID NO 45
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 45
accaaaagaa t                                                                11

<210> SEQ ID NO 46
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 46
tggccatcaa t                                                                11

<210> SEQ ID NO 47
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 47
tagcatactt a                                                                11

<210> SEQ ID NO 48
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 48 ccaaaaga                                                                     8

<210> SEQ ID NO 49
<211> LENGTH: 8
<212> TYPE: DNA
<213> ORGANISM: Artificial Sequence
<220> FEATURE:
<223> OTHER INFORMATION: Synthetic polynucleotide

<400> SEQUENCE: 49 catactta                                                                     8

<210> SEQ ID NO 50
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 50
cagacacgac caaaa                                                            15

<210> SEQ ID NO 51
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 51

-continued

```
tacttactga cagcc                                                        15

<210> SEQ ID NO 52
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 52
agacacgacc aaaag                                                        15

<210> SEQ ID NO 53
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 53
accaaaagaa t                                                            11

<210> SEQ ID NO 54
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 54
tggccatcaa t                                                            11

<210> SEQ ID NO 55
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 55
tagcatactt a                                                            11

<210> SEQ ID NO 56
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 56
cgaccaaaag aattc                                                        15

<210> SEQ ID NO 57
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 57
cgaccaaaag aattc                                                        15

<210> SEQ ID NO 58
<211> LENGTH: 15
<212> TYPE: DNA
<213> ORGANISM: Artificial Sequence
```

```
<220> FEATURE:
<223> OTHER INFORMATION: Synthetic polynucleotide

<400> SEQUENCE: 58
gatggccatc aatta                                                      15

<210> SEQ ID NO 59
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 59
gatggccatc aatta                                                      15

<210> SEQ ID NO 60
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 60
tctagcatac ttact                                                      15

<210> SEQ ID NO 61
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 61
tctagcatac ttact                                                      15

<210> SEQ ID NO 62
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 62
gaattcggat ggcca                                                      15

<210> SEQ ID NO 63
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 63
ggccatcaat tagtg                                                      15

<210> SEQ ID NO 64
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 64
ttcggatggc catca                                                      15
```

<210> SEQ ID NO 65
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 65
agccagacag cga                                                          13

<210> SEQ ID NO 66
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 66
gacagccaga cagca                                                        15

<210> SEQ ID NO 67
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (7)..(8)
<223> OTHER INFORMATION: LNA
<220> FEATURE:
<221> NAME/KEY: misc_feature
<222> LOCATION: (11)..(11)
<223> OTHER INFORMATION: LNA

<400> SEQUENCE: 67
accaaaagaa t                                                            11

<210> SEQ ID NO 68
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (11)..(11)
<223> OTHER INFORMATION: LNA

<400> SEQUENCE: 68
tggccatcaa t                                                            11

```
<210> SEQ ID NO 69
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (4)..(5)
<223> OTHER INFORMATION: LNA
<220> FEATURE:
<221> NAME/KEY: misc_feature
<222> LOCATION: (7)..(7)
<223> OTHER INFORMATION: LNA
<220> FEATURE:
<221> NAME/KEY: misc_feature
<222> LOCATION: (11)..(11)
<223> OTHER INFORMATION: LNA

<400> SEQUENCE: 69
tagcatactt a                                                          11

<210> SEQ ID NO 70
<211> LENGTH: 8
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(8)
<223> OTHER INFORMATION: LNA

<400> SEQUENCE: 70 ccaaaaga                                                               8

<210> SEQ ID NO 71
<211> LENGTH: 8
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(8)
<223> OTHER INFORMATION: LNA

<400> SEQUENCE: 71 catactta                                                               8

<210> SEQ ID NO 72
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (5)..(5)
<223> OTHER INFORMATION: LNA
<220> FEATURE:
<221> NAME/KEY: misc_feature
<222> LOCATION: (7)..(8)
```

```
<223> OTHER INFORMATION: LNA
<220> FEATURE:
<221> NAME/KEY: misc_feature
<222> LOCATION: (10)..(11)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 72
cagacacgac caaaa                                                          15

<210> SEQ ID NO 73
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (7)..(8)
<223> OTHER INFORMATION: LNA
<220> FEATURE:
<221> NAME/KEY: misc_feature
<222> LOCATION: (11)..(11)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 73
tacttactga cagcc                                                          15

<210> SEQ ID NO 74
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 74
agacacgacc aaaag                                                          15

<210> SEQ ID NO 75
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
```

<222> LOCATION: (13)..(15)
<223> OTHER INFORMATION: LNA

<400> SEQUENCE: 75
tacttactga cagcc                                                        15

<210> SEQ ID NO 76
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 76
tacttactga cagcc                                                        15

<210> SEQ ID NO 77
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (9)..(11)
<223> OTHER INFORMATION: LNA

<400> SEQUENCE: 77
accaaaagaa t                                                            11

<210> SEQ ID NO 78
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (9)..(11)
<223> OTHER INFORMATION: LNA

<400> SEQUENCE: 78
tggccatcaa t                                                            11

<210> SEQ ID NO 79
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: LNA
<220> FEATURE:

```
<221> NAME/KEY: misc_feature
<222> LOCATION: (9)..(11)
<223> OTHER INFORMATION: LNA

<400> SEQUENCE: 79
tagcatactt a                                                            11

<210> SEQ ID NO 80
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (5)..(6)
<223> OTHER INFORMATION: LNA
<220> FEATURE:
<221> NAME/KEY: misc_feature
<222> LOCATION: (9)..(10)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 80
cgaccaaaag aattc                                                        15

<210> SEQ ID NO 81
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 81
cgaccaaaag aattc                                                        15

<210> SEQ ID NO 82
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(9)
<223> OTHER INFORMATION: LNA
```

```
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 82
gatggccatc aatta                                                          15

<210> SEQ ID NO 83
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 83
gatggccatc aatta                                                          15

<210> SEQ ID NO 84
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(9)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (15)..(15)
<223> OTHER INFORMATION: LNA

<400> SEQUENCE: 84
tctagcatac ttact                                                          15

<210> SEQ ID NO 85
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
```

```
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 85
tctagcatac ttact                                                     15

<210> SEQ ID NO 86
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 86
gaattcggat ggcca                                                     15

<210> SEQ ID NO 87
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 87
ggccatcaat tagtg                                                     15

<210> SEQ ID NO 88
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 88
ttcggatggc catca                                                     15

<210> SEQ ID NO 89
<211> LENGTH: 13
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (1)..(4)
<223> OTHER INFORMATION: LNA
<220> FEATURE:
<221> NAME/KEY: misc_feature
<222> LOCATION: (13)..(5)
<223> OTHER INFORMATION: LNA

<400> SEQUENCE: 89
agccagacag cga                                                        13

<210> SEQ ID NO 90
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 90
gacagccaga cagca                                                      15

<210> SEQ ID NO 91
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 91
tacttactga cagtc                                                      15

<210> SEQ ID NO 92
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 92
tacttaccga cagcc                                                      15

<210> SEQ ID NO 93
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 93
ggatttcgga tggcca                                                     16

<210> SEQ ID NO 94
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
```

```
<221> NAME/KEY: misc_feature
<222> LOCATION: (13)..(15)
<223> OTHER INFORMATION: LNA

<400> SEQUENCE: 94
tacttactga cagtc                                                15

<210> SEQ ID NO 95
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 95
tacttaccga cagcc                                                15

<210> SEQ ID NO 96
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 96
ggatttcgga tggcca                                               16

<210> SEQ ID NO 97
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 97
agggctcttc ggccagcraa agcagg                                    26

<210> SEQ ID NO 98
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 98
cgaccaaaag aatt                                                 14

<210> SEQ ID NO 99
<211> LENGTH: 16
<212> TYPE: DNA
<213> ORGANISM: Artificial sequence
<220> FEATURE:
<223> OTHER INFORMATION: synthetic polynucleotide
```

<400> SEQUENCE: 99
gaccaaaaga attcgg                                                   16

<210> SEQ ID NO 100
<211> LENGTH: 16
<212> TYPE: DNA
<213> ORGANISM: Artificial sequence
<220> FEATURE:
<223> OTHER INFORMATION: synthetic polynucleotide

<400> SEQUENCE: 100
agcatactta ctgaca                                                   16

<210> SEQ ID NO 101
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 101
catacttact gaca                                                     14

<210> SEQ ID NO 102
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 102
atacttactg acag                                                     14

<210> SEQ ID NO 103
<211> LENGTH: 16
<212> TYPE: DNA
<213> ORGANISM: Artificial sequence
<220> FEATURE:
<223> OTHER INFORMATION: synthetic polynucleotide

<400> SEQUENCE: 103
catacttact gacagc                                                   16

<210> SEQ ID NO 104
<211> LENGTH: 16
<212> TYPE: DNA
<213> ORGANISM: Artificial sequence
<220> FEATURE:
<223> OTHER INFORMATION: synthetic polynucleotide

<400> SEQUENCE: 104
agacagcgac caaaag                                                   16

<210> SEQ ID NO 105
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 105
acagcgacca aaag                                                     14

<210> SEQ ID NO 106

```
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 106
cagccagaca gcgac                                                    15

<210> SEQ ID NO 107
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 107
cagccagaca gcga                                                     14

<210> SEQ ID NO 108
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 108
acagccagac agcga                                                    15

<210> SEQ ID NO 109
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 109
gacagccaga cagcg                                                    15

<210> SEQ ID NO 110
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 110
catcaattag tgtcg                                                    15

<210> SEQ ID NO 111
<211> LENGTH: 16
<212> TYPE: DNA
<213> ORGANISM: Artificial sequence
<220> FEATURE:
<223> OTHER INFORMATION: synthetic polynucleotide

<400> SEQUENCE: 111
ccatcaatta gtgtcg                                                   16

<210> SEQ ID NO 112
<211> LENGTH: 16
<212> TYPE: DNA
<213> ORGANISM: Artificial sequence
<220> FEATURE:
<223> OTHER INFORMATION: synthetic polynucleotide

<400> SEQUENCE: 112
```

-continued gccatcaatt agtgtg                                                      16

<210> SEQ ID NO 113
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 113
aagaattcgg atggc                                                       15

<210> SEQ ID NO 114
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 114
cagacagcga ccaa                                                        14

<210> SEQ ID NO 115
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 115
tgacagccag acagc                                                       15

<210> SEQ ID NO 116
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 116
cagccagaca gcgac                                                       15

<210> SEQ ID NO 117
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 117
cagccagaca gcgac                                                       15

```
<210> SEQ ID NO 118
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (11)..(14)
<223> OTHER INFORMATION: LNA

<400> SEQUENCE: 118
cagccagaca gcga                                                      14

<210> SEQ ID NO 119
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 119
cagccagaca gcga                                                      14

<210> SEQ ID NO 120
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 120
cagccagaca gcga                                                      14

<210> SEQ ID NO 121
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 121
acagccagac agcga                                                     15
```

```
<210> SEQ ID NO 122
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 122
acagccagac agcga                                                    15

<210> SEQ ID NO 123
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 123
acagccagac agcga                                                    15

<210> SEQ ID NO 124
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 124
gacagccaga cagcg                                                    15

<210> SEQ ID NO 125
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 125
```
gacagccaga cagcg                                                         15

<210> SEQ ID NO 126
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 126
gacagccaga cagcg                                                         15

<210> SEQ ID NO 127
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 127
catcaattag tgtcg                                                         15

<210> SEQ ID NO 128
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 128
ccatcaatta gtgtcg                                                        16

<210> SEQ ID NO 129
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 129
gccatcaatt agtgtg                                              16

<210> SEQ ID NO 130
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 130
aagaattcgg atggc                                               15

<210> SEQ ID NO 131
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 131
cagacagcga ccaa                                                14

<210> SEQ ID NO 132
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 132
tgacagccag acagc                                               15

<210> SEQ ID NO 133
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

```
<400> SEQUENCE: 133
gcgaccaaaa gaatt                                                    15

<210> SEQ ID NO 134
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 134
gcgaccaaaa gaatt                                                    15

<210> SEQ ID NO 135
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 135
cgaccaaaag aatt                                                     14

<210> SEQ ID NO 136
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 136
cgaccaaaag aattc                                                    15

<210> SEQ ID NO 137
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA
```

<400> SEQUENCE: 137
cgaccaaaag aattc                                                        15

<210> SEQ ID NO 138
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 138
cgaccaaaag aattc                                                        15

<210> SEQ ID NO 139
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 139
gaccaaaaga attc                                                         14

<210> SEQ ID NO 140
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 140
gcgaccaaaa gaattc                                                       16

<210> SEQ ID NO 141
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(16)

```
<223> OTHER INFORMATION: LNA

<400> SEQUENCE: 141
gcgaccaaaa gaattc                                                    16

<210> SEQ ID NO 142
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 142
gcgaccaaaa gaattc                                                    16

<210> SEQ ID NO 143
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 143
cgaccaaaag aattcg                                                    16

<210> SEQ ID NO 144
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 144
cgaccaaaag aattcg                                                    16

<210> SEQ ID NO 145
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
```

```
<222> LOCATION: (12)..(14)
<223> OTHER INFORMATION: LNA

<400> SEQUENCE: 145
gaccaaaaga attc                                                       14

<210> SEQ ID NO 146
<211> LENGTH: 13
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (11)..(13)
<223> OTHER INFORMATION: LNA

<400> SEQUENCE: 146
accaaaagaa ttc                                                        13

<210> SEQ ID NO 147
<211> LENGTH: 17
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(17)
<223> OTHER INFORMATION: LNA

<400> SEQUENCE: 147
cgaccaaaag aattcgg                                                    17

<210> SEQ ID NO 148
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 148
gaccaaaaga attcgg                                                     16

<210> SEQ ID NO 149
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
```

```
<221> NAME/KEY: misc_feature
<222> LOCATION: (14)..(16)
<223> OTHER INFORMATION: LNA

<400> SEQUENCE: 149
gaccaaaaga attcgg                                                   16

<210> SEQ ID NO 150
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 150
gaccaaaaga attcgg                                                   16

<210> SEQ ID NO 151
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 151
accaaaagaa ttcgga                                                   16

<210> SEQ ID NO 152
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 152
ccaaaagaat tcgga                                                    15

<210> SEQ ID NO 153
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
```

```
<220> FEATURE:
<221> NAME/KEY: misc_feature
<222> LOCATION: (12)..(14)
<223> OTHER INFORMATION: LNA

<400> SEQUENCE: 153
caaaagaatt cgga                                                          14

<210> SEQ ID NO 154
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 154
caaaagaatt cgga                                                          14

<210> SEQ ID NO 155
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 155
ccaaaagaat tcggat                                                        16

<210> SEQ ID NO 156
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 156
ccaaaagaat tcggat                                                        16

<210> SEQ ID NO 157
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
```

```
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 157
caaaagaatt cggat                                                    15

<210> SEQ ID NO 158
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 158
caaaagaatt cggat                                                    15

<210> SEQ ID NO 159
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 159
agcatactta ctgaca                                                   16

<210> SEQ ID NO 160
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 160
catacttact gaca                                                     14

<210> SEQ ID NO 161
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
```

```
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 161
catacttact gacag                                                     15

<210> SEQ ID NO 162
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 162
atacttactg acag                                                      14

<210> SEQ ID NO 163
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (11)..(14)
<223> OTHER INFORMATION: LNA

<400> SEQUENCE: 163
atacttactg acag                                                      14

<210> SEQ ID NO 164
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (11)..(14)
<223> OTHER INFORMATION: LNA

<400> SEQUENCE: 164
atacttactg acag                                                      14

<210> SEQ ID NO 165
<211> LENGTH: 16
<212> TYPE: DNA
<213> ORGANISM: Artificial sequence
<220> FEATURE:
<223> OTHER INFORMATION: synthetic polynucleotide
<220> FEATURE:
```

```
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 165
catacttact gacagc                                                    16

<210> SEQ ID NO 166
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 166
catacttact gacagc                                                    16

<210> SEQ ID NO 167
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 167
catacttact gacagc                                                    16

<210> SEQ ID NO 168
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 168
atacttactg acagc                                                     15

<210> SEQ ID NO 169
<211> LENGTH: 15
<212> TYPE: DNA
<213> ORGANISM: Artificial sequence
<220> FEATURE:
<223> OTHER INFORMATION: synthetic polynucleotide
```

```
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 169
atacttactg acagc                                                    15

<210> SEQ ID NO 170
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 170
atacttactg acagc                                                    15

<210> SEQ ID NO 171
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 171
atacttactg acagc                                                    15

<210> SEQ ID NO 172
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 172
tacttactga cagc                                                     14

<210> SEQ ID NO 173
<211> LENGTH: 14
<212> TYPE: DNA
<213> ORGANISM: Artificial sequence
<220> FEATURE:
```

```
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (11)..(14)
<223> OTHER INFORMATION: LNA

<400> SEQUENCE: 173
tacttactga cagc                                                        14

<210> SEQ ID NO 174
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (11)..(14)
<223> OTHER INFORMATION: LNA

<400> SEQUENCE: 174
tacttactga cagc                                                        14

<210> SEQ ID NO 175
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 175
atacttactg acagcc                                                      16

<210> SEQ ID NO 176
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 176
atacttactg acagcc                                                      16

<210> SEQ ID NO 177
<211> LENGTH: 15
<212> TYPE: DNA
<213> ORGANISM: Artificial sequence
```

```
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 177
tacttactga cagcc                                                    15

<210> SEQ ID NO 178
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 178
tacttactga cagcc                                                    15

<210> SEQ ID NO 179
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 179
tacttactga cagcca                                                   16

<210> SEQ ID NO 180
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 180
tacttactga cagcca                                                   16

<210> SEQ ID NO 181
<211> LENGTH: 16
<212> TYPE: DNA
```

```
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 181
tacttactga cagcca                                                    16

<210> SEQ ID NO 182
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 182
tacttactga cagcca                                                    16

<210> SEQ ID NO 183
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 183
acttactgac agcca                                                     15

<210> SEQ ID NO 184
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 184
acttactgac agcca                                                     15

<210> SEQ ID NO 185
<211> LENGTH: 15
```

```
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 185
acttactgac agcca                                                15

<210> SEQ ID NO 186
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (12)..(15)
<223> OTHER INFORMATION: LNA

<400> SEQUENCE: 186
cttactgaca gccag                                                15

<210> SEQ ID NO 187
<211> LENGTH: 15
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 187
ttactgacag ccaga                                                15

<210> SEQ ID NO 188
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 188
agacagcgac caaaag                                               16

<210> SEQ ID NO 189
```

```
<211> LENGTH: 16
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (13)..(16)
<223> OTHER INFORMATION: LNA

<400> SEQUENCE: 189
agacagcgac caaaag                                                    16

<210> SEQ ID NO 190
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: LNA
<220> FEATURE:
<221> NAME/KEY: misc_feature
<222> LOCATION: (11)..(14)
<223> OTHER INFORMATION: LNA

<400> SEQUENCE: 190
acagcgacca aaag                                                      14

<210> SEQ ID NO 191
<211> LENGTH: 14
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 191
acagcgacca aaag                                                      14
```